(12) United States Patent
Klaenhammer et al.

(10) Patent No.: US 7,981,651 B2
(45) Date of Patent: Jul. 19, 2011

(54) LACTOBACILLUS ACIDOPHILUS NUCLEIC ACIDS AND USES THEREOF

(75) Inventors: Todd R. Klaenhammer, Raleigh, NC (US); Eric Altermann, Palmerston North (NZ); Andrea Azcarate-Peril, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/253,333

(22) Filed: Oct. 17, 2008

(65) Prior Publication Data

US 2009/0155213 A1    Jun. 18, 2009

Related U.S. Application Data

(62) Division of application No. 11/260,843, filed on Oct. 27, 2005, now Pat. No. 7,468,182.

(60) Provisional application No. 60/711,491, filed on Aug. 26, 2005, provisional application No. 60/622,712, filed on Oct. 27, 2004.

(51) Int. Cl.
*C12N 9/02* (2006.01)
*C12N 1/20* (2006.01)
*C07H 21/04* (2006.01)
*C12P 21/06* (2006.01)

(52) U.S. Cl. ............... 435/189; 435/252.9; 435/252.1; 435/69.1; 435/6; 435/320.1; 435/325; 536/23.2

(58) Field of Classification Search .............. None
See application file for complete search history.

(56) References Cited

U.S. PATENT DOCUMENTS

| | | | |
|---|---|---|---|
| 5,837,509 A | 11/1998 | Israelsen et al. | |
| 5,912,125 A * | 6/1999 | Peck et al. | ............ 435/6 |
| 6,451,584 B2 | 9/2002 | Tomita et al. | |
| 6,476,209 B1 | 11/2002 | Glenn et al. | |
| 6,544,772 B1 | 4/2003 | Glenn et al. | |
| 6,635,460 B1 | 10/2003 | Van Hijum et al. | |
| 6,713,617 B2 * | 3/2004 | Minoprio et al. | ........... 536/23.2 |
| 2002/0061292 A1 | 5/2002 | DeSimone | |
| 2002/0159976 A1 | 10/2002 | Glenn et al. | |
| 2003/0138822 A1 | 7/2003 | Glenn et al. | |
| 2004/0009490 A1 | 1/2004 | Glenn et al. | |
| 2004/0208863 A1 | 10/2004 | Versalovic et al. | |
| 2005/0003510 A1 | 1/2005 | Chang et al. | |
| 2005/0112612 A1 | 5/2005 | Klaenhammer et al. | |
| 2005/0123941 A1 | 6/2005 | Klaenhammer et al. | |
| 2005/0250135 A1 | 11/2005 | Klaenhammer et al. | |

FOREIGN PATENT DOCUMENTS

| | | |
|---|---|---|
| EP | 0 888 118 B1 | 1/1999 |
| WO | WO 98/52586 | 11/1998 |
| WO | WO 02/12506 A1 | 2/2002 |
| WO | WO 02/074798 A2 | 9/2002 |
| WO | WO 03/084989 A2 | 10/2003 |
| WO | WO 2004/020467 A2 | 3/2004 |
| WO | WO 2004/031389 A1 | 4/2004 |
| WO | WO 2004/069178 A2 | 8/2004 |
| WO | WO 2004/096992 A2 | 11/2004 |
| WO | WO 2005/001057 A2 | 1/2005 |
| WO | WO 2005/012491 A2 | 2/2005 |
| WO | WO 2005/081959 A2 | 9/2005 |
| WO | WO 2005/084411 | 9/2005 |
| WO | WO 2005/086794 A2 | 9/2005 |

OTHER PUBLICATIONS

Peck et al. Genbank Accession No. AAV34839, Apr. 23, 1998.*
Klaenhammer et al (Appld Environ Microbiol. 1980, pp. 671-674).*
Abee et al. (1994) "Kinetic studies of the action of lactacin F, a bacteriocin produced by *Lactobacillus johnsonii* that forms poration complexes in the cytoplasmic membrane" *Appl. Environ. Microbiol.* 60:1006-10013.
Allison and Klaenhammer (1996) "Functional analysis of the gene encoding immunity to lactacin F, *lafI*, and its use as a *Lactobacillus*-specific, food-grade genetic marker" *Appl. Environ. Microbial.* 62:4450-4460.
Allison and Klaenhammer (1999) "Genetics of bacteriocins produced by lactic acid bacteria and their use in novel industrial applications" in *Manual of Industrial Microbiology and Biotechnology*. DeMain and Davies (eds.), ASM Press, Washington, D.C., pp. 789-808.
Allison et al. (1994) "Expansion of bacteriocin activity and host range upon complementation of two peptides encoded with the lactacin F operon" *J. Bacteriol.* 176:2235-2241.
Altermann et al. (2004) "Identification and phenotypic characterization of the cell-division protein CdpA" *Gene* 342:189-197.
Altermann et al. (2005) "Complete genome sequence of the probiotic lactic acid bacterium *Lactobacillus acidophilus* NCFM" *Proc. Natl. Acad. Sci. U.S.A.* Early Edition 10.1073/pnas.0409188102, online publication date Jan. 25, 2005.
Azcarate-Peril et al. (2004) "Identification and inactivation of genetic loci involved with *Lactobacillus acidophilus* acid tolerance" *Appl. Environ. Microbiol.* 70:5315-5322.
Azacarate-Peril, M., et al., "Transcriptional and Functional Analysis of Oxalyl-Coenzyme A (CoA) Decarboxylase and Formyl-CoA Transferese Genes from *Lactobacillus acidophilus*," *Applied and Environmental Microbiology*, 2006, pp. 1891-1899, vol. 72 (3).
Barefoot and Klaenhammer (1983) "Detection and activity of lactacin B, a bacteriocin produced by *Lactobacillus acidophilus*" *Appl. Environ. Microbiol.* 45:1808-1815.

(Continued)

*Primary Examiner* — Delia M Ramirez
*Assistant Examiner* — Younus Meah
(74) *Attorney, Agent, or Firm* — Alston & Bird LLP

(57) ABSTRACT

*Lactobacillus acidophilus* NCFM nucleic acid molecules, polypeptides, fragments and variants thereof are provided in the current invention. In addition, fusion proteins, antigenic peptides, and antibodies are encompassed. The invention also provides recombinant expression vectors containing a nucleic acid molecule of the invention and cells comprising the expression vectors. Methods for producing the polypeptides of the invention and methods for their use are further provided.

37 Claims, 6 Drawing Sheets

OTHER PUBLICATIONS

Barefoot and Klaenhammer (1984) "Purification and characterization of the *Lactobacillus acidophilus* bacteriocin lactacin B" *Antimicrob. Agents Chemother.* 26:328-334.

Barefoot et al. (1994) "Identification and purification of a protein that induces production of the *Lactobacillus acidophilus* bacteriocin lactacin B" *Appl. Environ. Microbiol.* 60:3522-3528.

Barrangou et al. (2003) "Functional and comparative genomic analyses of an operon involved in fructooligosaccharide utilization by *Lactobacillus acidophilus*" *Proc. Natl. Acad. Sci. U.S.A.* 100:8957-8962.

Boels et al. (2001) "Functional analysis of the *Lactococcus lactis* galU and galE genes and their impact on sugar nucleotide and exopolysaccharide biosynthesis" *Appl. Environ. Microbiol.* 67:3033-3040.

Bruno-Barcena et al. (2004) "Expression of heterologous manganese superoxide dismutase gene in intestinal lactobacilli provides protection against hydrogen peroxide toxicity" *Appl. Environ. Microbiol.* 70:4702-4710.

Campieri, C., et al., "Reduction of Oxaluria After an Oral Course of Lactid Acid Bacteria at High Concentration," *Kidney International*, 2001, pp. 1097-1105, vol. 60.

Christensen et al. (1999) "Peptidases and Amino Acid Catabolism in Lactic Acid Bacteria" *Antonie van Leeuwenhoek* 76: 217-246.

Coconnier et al. (1992) "Protein-mediated adhesion of *Lactobacillus acidophilus* BG2FO4 on human enterocyte and mucus-secreting cell lines in culture" *Appl. Environ. Microbiol.* 58:2034-2039.

Contreras et al. (1997) "Isolation, purification and amino acid sequence of lactobin A, one of the two bacteriocins produced by *Lactobacillus amylovorus* LMG P-13139" *Appl. Environ. Microbiol.* 63:13-20.

De Vuyst and Degeest (1998) "Heteropolysaccharides from lactic acid bacteria" *FEMS Microbiol. Rev.* 23:153-177.

Dodd and Gasson (1994) "Bacteriocins of lactic acid bacteria" *in Genetics and Biotechnology of Lactic Acid Bacteria.* Gasson and de Vos (eds.), Blackie Academic and Professional, London, pp. 211-251.

Federici, F., et al., "Characterization and Heterologous Expression of the Oxalyl Coenzyme A Decarboxylase Gene from Bifidobacterium Lactis," *Applied and Environmental Microbiology*, 2004, pp. 5066-5073, vol. 70 (9).

Fremaux et al. (1993) "Molecular analysis of the lactacin F operon" *Appl. Environ. Microbiol.* 59:3906-3915.

Girgis et al. (2002) "Stress adaptations of lactic acid bacteria" *in Microbial adaptation to stress and safety of new-generation foods.* Yousef and Juneja (eds.) CRC Press, NY, pp. 159-212.

Greene and Klaenhammer (1994) "Factors involved in adherence of lactobacilli to human Caco-2 cells" *Appl. Environ. Microbiol.* 60:4487-4494.

Heider, J., "A New Family of CoA-transferases," *FEBS Letters*, 2001, vol. 509, pp. 345-349.

Holzapfel et al. (2001) "Taxonomy and Important Features of Probiotic Microorganisms in Food and Nutrition" *Am J of Clil Nutr* 73 Suppl: 365S-373S.

Hugenholtz (1999) "Metabolic Engineeing of Lactic Acid Bacteria: Overview of the Approaches and Results of Pathway Rerouting Involved in Food Fermentations" *Current Opinion in Biotechnology* 10:492-497.

Joerger and Klaenhammer (1986) "Characterization and purification of helveticin J and evidence for a chromosomally determined bacteriocin produced by *Lactobacillus helveticus*" *J. Bacteriol.* 167:439-446.

Joerger et al. (1990) "Cloning, expression, and nucleotide sequence of the *Lactobacillus helveticus* 481 gene encoding the bactericin helveticin J" *J. Bacteriol.* 172:6339-6347.

Jolly et al. (2002) "Exploiting exopolysaccharides from lactic acid bacteria" *Antonie van Leeuwenhoek* 82:367-374.

Klaenhammer (1988) "Bacteriocins of lactic acid bacteria" *Biochimie* 70:337-349.

Klaenhammer (1993) "Genetics of bacteriocins produced by lactic acid bacteria" *FEMS Microbiol. Rev.* 12:39-85.

Klaenhammer (2000) "Probiotic bacterica: today and tomorrow" *J. Nutr.* 130(2S Suppl.):415S-416S.

Klaenhammer and Kullen (1999) "Selection and design of probiotics" *Int. J. Food Microbiol.* 50:45-57.

Klaenhammer and Sutherland (1980) "Detection of plasmid deoxyribonucleic acid in an isolate of *Lactobacillus acidophilus*" *Appl. Environ. Microbiol.* 39:671-674.

Klaenhammer et al. (2002) "Discovering lactic acid bacteria by genomics" *Antonie van Leeuwenhoek* 82:29-58.

Klaenhammer et al. (2005) "*Lactobacillus acidophilus* Nucleic Acid Sequences Encoding Protease Homologues and Uses Therefore" U.S. Appl. No. 11/062,665, filed Feb. 22, 2005.

Klaenhammer et al. (2005) "*Lactobacillus acidophilus* Nucleic Acid Sequences Encoding Carbohydrate Utilization-Related Proteins and Uses Therefor" U.S. Appl. No. 11/074,226, filed Mar. 7, 2005.

Kleeman and Klaenhammer (1982) "Adherence of *Lactobacillus* species to human fetal intestinal cells" *J. Dairy Sci.* 65:2063-2069.

Kleerebezem et al. (1999) "Exopolysaccharides produced by *Lactococcus lactis*: from genetic engineering to improved rheological properties?" *Antonie van Leeuwenhoek* 76:357-365.

Kleerebezem et al. (2003) "Complete genome sequence of *Lactobacillus plantarum* WCFS1" *Proc. Natl. Acad. Sci. U.S.A.* 100:1990-1995.

Kok et al. (1994) "The Proteolytic System of Lactic Acid Bacteria" *Genetics and Biotechnology of Lactic Acid Bacteria* pp. 169-210.

Konigs et al. (1997) "The role of transport processes in survival of lactic acid bacteria" *Antonie van Leeuwenhoek* 71:117-128.

Konigs et al. (2000) "Lactic acid bacteria: the bugs of a new millennium" *Curr. Opin. Microbiol.* 3:276-282.

Kuipers et al. (2000) "Current Strategies for Improving Food Bacteria" *Res Microbiol* 151: 815-822.

Kullen and Klaenhammer (1999) Identification of the pH-inducible, proton-translocating $F_1F_0$-ATPase (atpBEFHAGDC) operon of *Lactobacillus acidophilus* by differential display: gene structure, cloning and characterization *Mol. Microbiol.* 33:1152-1161.

Kullen and Klaenhammer (2000) "Genetic modification of intestinal lactobacilli and bifidobacteria" *Curr. Issues Mol. Biol.* 2:41-50.

Kullen et al. (2000) "Use of the DNA sequence of variable regions of the 16S rRNA gene for rapid and accurate identification of bacteria in the *Lactobacillus acidophilus* complex" *J. Appl. Microbiol.* 89:511-516.

Law et al. (1997) "Proteolytic Enzymes of Lactic Acid Bacteria" *Int Dairy Journal* 7: 1-11.

Luchansky et al. (1988) "Application of electroporation for transfer of plasmid DNA to *Lactobacillus, Lactococcus, Leuconostoc, Listeria, Pediococcus, Bacillus, Staphylococcus, Enterococcus* and *Propionobacterium*" *Mol. Microbiol.* 2:637-646.

Luchansky et al. (1989) "Genetic transfer systems for delivery of plasmid deoxyribonucleic acid to *Lactobacillus acidophilus* ADH: conjugation, electroporation, and transduction" *J. Dairy Sci.* 72:1408-1417.

Luchansky et al. (1991) "Molecular cloning and deoxyribonucleic acid polymorphisms in *Lactobacillus acidophilus* and *Lactobacillus gasseri*" *J. Dairy Sci.* 74:3293-3302.

Majhenic et al. (2004) "DNA analysis of the genes encoding acidocin LF221 A and acidocin LF221 B, two bacteriocins produced by *Lactobacillus gasseri* LF221" *Appl. Microbiol. Biotechnol.* 63:705-714.

Mohamadzadeh et al. (2005) "Lactobacilli activate human dendritic cells that skew T cells toward T helper 1 polarization" *Proc. Nat. Acad. Sci. USA* 102:2880-2885.

Muriana and Klaenhammer (1991) "Cloning, phenotypic expression, and DNA sequence of the gene for lactacin F, an antimicrobial peptide produced by *Lactobacillus spp.*" *J. Bacteriol.* 173:1779-1788.

Muriana and Klaenhammer (1991) "Purification and partial characterization of lactacin F, a bacteriocin produced by *Lactobacillus acidophilus* 11088" *Appl. Environ. Microbiol.* 57:114-121.

Pao et al. (1998) "Major Facilitator Superfamily" *Microbiol. Mol. Biol. Rev.* 62:1-34.

Poolman (2002) "Transporters and their roles in LAB cell physiology" *Antonie van Leeuwenhoek* 82:147-164.

Pridmore et al. (2004) "The genome sequence of the probiotic intestinal bacterium *Lactobacillus johnsonii* NCC 533" *Proc. Natl. Acad. Sci. U.S.A.* 101:2512-2517.
Putman et al. (2000) "Molecular properties of bacterial multidrug transporters" *Microbiol. Mol. Biol. Rev.* 64:672-693.
Rastall et al. (2005). Modulation of the microbial ecology of the human colon by probiotics, prebiotics and synbiotics to enhance human health: An overview of enabling science and potential applications. *FEMS Microbiol. Ecol.* 52:145-152.
Roy et al. (1993) "Cloning and expression of the manganese superoxide dismutase gene of *Escherichia coli* in *Lactococcus lactis* and *Lactobacillus gasseri*" *Mol. Gen. Genet.* 239:33-40.
Russell and Klaenhammer (2001) "Efficient system for directed integration into the *Lactobacillus acidophilus* and *Lactobacillus gasseri* chromosomes via homologous recombination" *Appl. Environ. Microbiol.* 67:4361-4364.
Russell and Klaenhammer (2001) "Identification and cloning of *gus*A, encoding a new β-glucuronidase from *Lactobacillus gasseri* ADH" *Appl. Environ. Microbiol.* 67:1253-1261.
Sablon et al. (2000) "Antimicrobiol peptides of lactic acid bacteria: mode of action, genetics and biosynthesis"*in Advances in Biochemical Engineering/Biotechnology*. vol. 68. Schleper (ed.), Springer-Verlag, Berlin, pp. 21-60.
Sanders and Klaenhammer (2001) "Invited review: the scientific basis of *Lactobacillus acidophilus* NCFM functionality as a probiotic" *J. Dairy Sci.* 84:319-331.
Sanders et al. (1996) "Performance of commercial cultures in fluid milk applications" *J. Dairy Sci.* 79:943-955.
Steidler et al. (1998) "Functional display of a heterologous protein on the surface of Lactococcus lactis by means of the cell wall anchor of *Staphylococcus aureus* protein A" *Appl. Environ. Microbiol.* 64:342-345.
Sturino and Klaenhammer (2004) "Bacteriophage defense systems for lactic acid bacteria" *Adv. Appl. Microbiol.* 56:331-378.
Ventura et al. (2003) "Analysis, characterization, and loci of *tuf* genes in *Lactobacillus* and *Bifidobacterium* species and their direct application for species identification" *Appl. Environ. Microbiol.* 69:6908-6922.
Walker et al. (1999) "The groESL chaperone operon of *Lactobacillus johnsonii*" *Appl. Environ. Microbiol.* 65:3033-3041.
Yother et al. (2002) Genetics of streptococci, lactococci, and enterococci: review of the sixth international conference *J. Bacteriol.* 184:6085-6092.
GenBank Accession No. AAA19050, filed Jun. 1, 1994; Prolinase; Source: *Lactobacillus helveticus*.
GenBank Accession No. AAA25250, filed Jan. 13, 1994; Aminopeptidase C.; Source: *Lactobacillus helveticus*.
GenBank Accession No. AAB52540, filed Apr. 18, 1998; Endopeptidase; Source: *Lactobacillus helveticus*.
GenBank Accession No. AAB66326, filed Aug. 7, 1997; GroEL; Source: *Lactobacillus zeae*.
GenBank Accession No. AAC29003; filed Aug. 7, 1998; cochaperonin GroES; Source: *Lactobacillus helveticus*.
GenBank Accession No. AAC99363, filed Sep. 10, 1999; D-lactate dehydrogenase; Source: *Lactobacillus johnsonii*.
GenBank Accession No. AAF22492, filed Aug. 30, 2001; F1F0-ATPase subunit a; Source: *Lactobacillus acidophilus*.
GenBank Accession No. AAF22494, filed Aug. 30, 2001; F1F0-ATPase subunit b; Source: *Lactobacillus acidophilus*.
GenBank Accession No. AAF22495, filed Aug. 30, 2001; F1F0-ATPase subunit delta; Source: *Lactobacillus acidophilus*.
GenBank Accession No. AAF22496, filed Aug. 30, 2001; F1F0-ATPase subunit alpha; Source: *Lactobacillus acidophilus*.
GenBank Accession No. AAF22497, filed Aug. 30, 2001; F1F0-ATPase subunit gamma; Source: *Lactobacillus acidophilus*.
GenBank Accession No. AAF22498, filed Aug. 30, 2001; F1F0-ATPase subunit beta; Source: *Lactobacillus acidophilus*.
GenBank Accession No. AAF22499, filed Aug. 30, 2001; F1F0-ATPase subunit epsilon; Source: *Lactobacillus acidophilus*.
GenBank Accession No. AAF75593, filed Jun. 13, 2000; GroEL; Source: *Lactobacillus johnsonii*.
GenBank Accession No. AAK97217, filed Sep. 2, 2001; cochaperonin GroES; Source: *Lactobacillus acidophilus*.
GenBank Accession No. AAK97218, filed Sep. 2, 2001; chaperonin GroEL; Source: *Lactobacillus acidophilus*.
GenBank Accession No. AAK97220, filed Sep. 2, 2001; cochaperonin GrpE; Source: *Lactobacillus acidophilus*.
GenBank Accession No. AAK97221, filed Sep. 2, 2001; heat shock protein DnaK; Source: *Lactobacillus acidophilus*.
GenBank Accession No. AAQ72431, filed Jun. 3, 2005; Endopeptidase E2; Source: *Lactobacillus helveticus*.
GenBank Accession No. AAR25444, filed Dec. 3, 2003; Tuf; *Lactobacillus johnsonii*.
GenBank Accession No. AAT09141, filed Sep. 7, 2004; amino acid permease La995; Source: *Lactobacillus acidophilus*.
GenBank Accession No. AF010281, filed Aug. 9, 1997; Lactobacillus zeae GroES; Source: *Lactobacillus zeae*.
GenBank Accession No. AF031929, filed Aug. 8, 1998; *Lactobacillus helveticus* cochaperonin GroES and chaperonin GroEL genes, complete cds and DNA mismatch repair enzyme (hexA) gene, partial cds; Source: *Lactobacillus helveticus*.
GenBank Accession No. AF071558, filed Sep. 10, 1999; *Lactobacillus johnsonii* D-lactate dehydrogenase (ldhD) gene, complete cds; Source: *Lactobacillus johnsonii*.
GenBank Accession No. AF098522, filed Aug. 30, 2001; *Lactobacillus acidophilus* uracil phosphoribosyltransferase; Source: *LActobacillus acidophilus*.
GenBank Accession No. AF214488, filed Jun. 13, 2000; *Lactobacillus johnsonii* groESL operon, complete sequence and unknown gene; Source: *Lactobacillus johnsonii*.
GenBank Accession No. AF300645, filed Sep. 2, 2001; *Lactobacillus acidophilus* groESL operon, complete sequence; Source: *Lactobacillus acidophilus*.
GenBank Accession No. AF300646, filed Sep. 2, 2001; *Lactobacillus acidophilus* repressor protein HrcA (hrcA) gene, partial cds; cochaperonin GrpE (grpE) and heat shock protein DnaK (dnaK) genes, complete cds, and DnaJ (dnaJ) gene, partical cds; Source: *Lactobacilus acidophilus*.
GenBank Accession No. B59088, filed Jun. 20, 1998; Prolyl Aminopeptidase; Source: *Lactobacillus helveticus*.
GenBank Accession No. CAA42781, filed Nov. 5, 1992; D-lactate dehydrogenase; Source: *Lactobacillus delbrueckii*.
GenBank Accession No. CAA59019, filed Apr. 18, 2005; heat shock induced protein HtpI; Source: *Lactobacillus leichmannii*.
GenBank Accession No. CAA61561, filed Jan. 22, 1996; Sb-protein; *Lactobacillus acidophilus*.
GenBank Accession No. CAA86210, filed Oct. 17, 1996; Dipeptidase; Source: *Lactobacillus helveticus*.
GenBank Accession No. CAB72938, filed Apr. 15, 2005; Tripeptidase Enzyme; Source: *Lactobacillus helveticus*.
GenBank Accession No. NP_964658, filed Jan. 26, 2007; probable xylulose-5-phosphate/fructose-6-phosphate phosphoketolase; Source: *Lactobacillus johnsonii* NCC 533.
GenBank Accession No. NP_964694, filed Jan. 26, 2007; RecA protein; Source: *Lactobacillus johnsonii* NCC 533.
GenBank Accession No. NP_964728, filed Jan. 26, 2007; phosphoglycerate kinase; Source: *Lactobacillus johnsonii* NCC 533.
GenBank Accession No. NP_964948, filed Jan. 26, 2007; DNA-binding protein HU; Source: *Lactobacillus johsonii* NCC 533.
GenBank Accession No. NP_965314, filed Jan. 26, 2007; 50S ribosomal protein L19; Source: *Lactobacillus johnsonii* NCC 533.
GenBank Accession No. NP_965472, filed Jan. 26, 2007; thioredoxin; Source: *Lactobacillus johnsonii* NCC 533.
GenBank Accession No. NP_966600, filed Dec. 2, 2005; hypothetica protein LJ1693; Source: *Lactobacillus johnsonii* NC 533.
GenBank Accession No. 007684, filed Oct. 17, 2006; Beta-galactosidase large subunit; Source: *Lactobacillus acidophilus*.
GenBank Accession No. O07685, filed Nov. 28, 2006; Beta-galactosidase small subunit; Source: *Lactobacillus acidophilus*.
GenBank Accession No. O32755, filed Oct. 17, 2006; Glyceraldehyde-3-phosphate dehydrogenase; Source: *Lactobacillus delbrueckii subsp. Bulgaricus*.
GenBank Accession No. 032756, filed Apr. 18, 2006; Phosphoglycerate kinase; Source: *Lactobacillus delbrueckii subsp. Bulgaricus*.

GenBank Accession No. O32765, filed Nov. 28, 2006; L-lactate dehydrogenase; Source: *Lactobacillus helveticus*.

GenBank Accession No. O68324, filed Mar. 21, 2006; 60 kDa chaperonin; Source: *Lactobacillus helveticus*.

GenBank Accession No. O84913, filed Nov. 28, 2006; Xaa-Pro dipeptidase; Source: *Lactobacillus helveticus*.

GenBank Accession No. P26297, filed Jan. 23, 2007; D-lactate dehydrogenase; Source: *Lactobacillus delbrueckii subsp. Bulgaricus*.

GenBank Accession No. P30901, filed Jan. 23, 2007; D-lactate dehydrogenase; Source: *Lactobacillus helveticus*.

GenBank Accession No. P34038, filed Nov. 28, 2006; Pyruvate kinase; Source: *Lactobacillus delbrueckii subsp. Bulgaricus*.

GenBank Accession No. P35829, filed Jan. 9, 2007; S-layer protein precursor; Source: *Lactobacillus acidophilus*.

GenBank Accession No. P43451, filed Oct. 17, 2006; ATP synthase beta chain; Source: *Enterococcus hirae*.

GenBank Accession No. P94870, filed Feb. 7, 2006; Aminopeptidase E.; Source: *Lactobacillus helveticus*.

GenBank Accession No. Q00052, filed Mar. 21, 2006; Galactokinase; Source: *Lactobacillus helveticus*.

GenBank Accession No. Q10730, filed Feb. 7, 2006; Aminopeptidase N; Source: *Lactobacillus helveticus*.

GenBank Accession No. Q10744, filed Feb. 7, 2006; Aminopeptidase C.; Source: *Lactobacillus helveticus*.

GenBank Accession No. Q48558, filed Nov. 28, 2006; Dipeptidase A.; Source: *Lactobacillus helveticus*.

GenBank Accession No. Q9Z4H7, filed Oct. 17, 2006; Serine protease do-like htrA; Source: *Lactobacillus helveticus*.

GenBank Accession No. S47274, filed Feb. 1, 2002; Membrane Alanyl Aminopeptidase; Source: *Lactobacillus helveticus*.

GenBank Accession No. S47276, filed Jan. 6, 1995; Prolinase; Source: *Lactobacillus helveticus*.

GenBank Accession No. X60220, filed Nov. 5, 1992; L. delbrueckii subsp. Bulgaricus ldhA gene for D-lactate dehydrogenase; Source: *Lactobacillus delbrueckii*.

GenBank Accession No. X84261, filed Apr. 18, 2005; L.Leichmannii xerC, hs1U and hs1V; Source: *Lactobacillus leichmannii*.

GenBank Accession No. X89376, filed Jan. 22, 1996; L. acidophilus DNA for SB-protein gene; Source: *lactobacillus acidophilus*.

GenBank Accession No. ZP_00046537, filed May 25, 2006; COG0124: Histidyl-tRNA sythetase; Source: *Lactobacillus gasseri*.

GenBank Accession No. ZP_00046557, filed May 25, 2006; COG0148: Enolase; Source: *Lactobacillus gasseri*.

GenBank Accession No. ZP_00046583, filed May 25, 2006; COG0195: Transcription elongation factor; Source: *Lactobacillus gasseri*.

GenBank Accession No. ZP_00047305; filed May 25, 2006 COG4690: Dipeptidase; Source: *Lactobacillus gasseri*.

GenBank Accession No. ZP_00341831, filed May 25, 2006; COG0522: Ribosomal protein S4 and related proteins; Source: *Lactobacillus gasseri*.

GenBank Accession no. Q03234, filed Oct. 17, 2006; ATP synthesis beta chain; *Lactobacillus casei*.

Peck, et al, (GenBank Accession No. AAV34838), filed Oct. 30, 2004.

\* cited by examiner

A. Non-adapted cells

B. Oxalate pre-adapted cells

SEQUENCE LISTING

<160> NUMBER OF SEQ ID NOS: 36

<210> SEQ ID NO 1
<211> LENGTH: 1335
<212> TYPE: DNA
<213> ORGANISM: Lactobacillus Acidophilus
<220> FEATURE:
<221> NAME/KEY: CDS
<222> LOCATION: (1)...(1335)

<400> SEQUENCE: 1

```
atg act gaa gaa gaa aat gaa tat gca cct tta aaa ggt att aaa gtc      48
Met Thr Glu Glu Glu Asn Glu Tyr Ala Pro Leu Lys Gly Ile Lys Val
 1               5                  10                  15 gtt gac tgg act caa gta caa tct ggt cca tca tgt act caa att tta      96
Val Asp Trp Thr Gln Val Gln Ser Gly Pro Ser Cys Thr Gln Ile Leu
             20                  25                  30 gct tgg ctt ggt gcc gaa gtt att aaa att gaa cgt act aat act ggt     144
Ala Trp Leu Gly Ala Glu Val Ile Lys Ile Glu Arg Thr Asn Thr Gly
         35                  40                  45 gat cca acc aga aat gaa tta ctt gat att caa gat tca tgg agt ttg     192
Asp Pro Thr Arg Asn Glu Leu Leu Asp Ile Gln Asp Ser Trp Ser Leu
     50                  55                  60 tac tac tta caa tta aat gcc aac aag aag tca tta aca tta aac att     240
Tyr Tyr Leu Gln Leu Asn Ala Asn Lys Lys Ser Leu Thr Leu Asn Ile
 65                  70                  75                  80 aag gct cca gaa ggc aaa aag atc atg tac gac ttg ctt aag aaa gcc     288
Lys Ala Pro Glu Gly Lys Lys Ile Met Tyr Asp Leu Leu Lys Lys Ala
             85                  90                  95 gat atc ttt gtt gaa aat att aaa cct ggt gct gca gaa aaa gct ggc     336
Asp Ile Phe Val Glu Asn Ile Lys Pro Gly Ala Ala Glu Lys Ala Gly
            100                 105                 110 tat ggt tgg gaa act gtt cac aag ctt aat cca cgt ttg att atg gct     384
Tyr Gly Trp Glu Thr Val His Lys Leu Asn Pro Arg Leu Ile Met Ala
        115                 120                 125 tca ctt aaa ggt ttc aac gaa ggc tca cgt ttt gct aac gtt aag gct     432
Ser Leu Lys Gly Phe Asn Glu Gly Ser Arg Phe Ala Asn Val Lys Ala
    130                 135                 140 ttt gaa cca gtt gct caa gct gct ggt ggt gct gca tct gct act ggt     480
Phe Glu Pro Val Ala Gln Ala Ala Gly Gly Ala Ala Ser Ala Thr Gly
```

```
                145                 150                 155                 160
tgg aac aaa ggc gaa ttt aac gtt cct acc caa tca gca gct gct tta        528
Trp Asn Lys Gly Glu Phe Asn Val Pro Thr Gln Ser Ala Ala Ala Leu
                    165                 170                 175 ggt gac tca aac tca ggt atg cac tta act att gct att tta gct gct        576
Gly Asp Ser Asn Ser Gly Met His Leu Thr Ile Ala Ile Leu Ala Ala
            180                 185                 190 tta atg caa cgt gaa cac act ggt gaa ggt act tat gta tac caa tca        624
Leu Met Gln Arg Glu His Thr Gly Glu Gly Thr Tyr Val Tyr Gln Ser
        195                 200                 205 atg caa gat gct gta tta aac ctt tgc cgt att aag tta cgt gac caa        672
Met Gln Asp Ala Val Leu Asn Leu Cys Arg Ile Lys Leu Arg Asp Gln
    210                 215                 220 ctt atg tta gac aac tta ggt gct tta cct cac tat gct gtt tac cct        720
Leu Met Leu Asp Asn Leu Gly Ala Leu Pro His Tyr Ala Val Tyr Pro
225                 230                 235                 240 aac tat aag tgg gga gac gct att cct cgt gct gag aac act gaa ggt        768
Asn Tyr Lys Trp Gly Asp Ala Ile Pro Arg Ala Glu Asn Thr Glu Gly
                245                 250                 255 ggt caa gtt atc ggt tgg act tat aaa gct aaa ggc tgg gaa act gat        816
Gly Gln Val Ile Gly Trp Thr Tyr Lys Ala Lys Gly Trp Glu Thr Asp
            260                 265                 270 cct aat gct tat gtc tac att gtt gtt caa aac agt aac aag agc tgg        864
Pro Asn Ala Tyr Val Tyr Ile Val Val Gln Asn Ser Asn Lys Ser Trp
        275                 280                 285 gaa gct att gca aat acc atg ggt cat cca gaa tgg att act gat gaa        912
Glu Ala Ile Ala Asn Thr Met Gly His Pro Glu Trp Ile Thr Asp Glu
    290                 295                 300 cgt ttc caa gat tgg caa cat cgt caa ttg aat aaa gaa gct ctt tac        960
Arg Phe Gln Asp Trp Gln His Arg Gln Leu Asn Lys Glu Ala Leu Tyr
305                 310                 315                 320 caa tgt att gaa agc tac acc aag aat tat gac aaa ttt gaa tta acc       1008
Gln Cys Ile Glu Ser Tyr Thr Lys Asn Tyr Asp Lys Phe Glu Leu Thr
                325                 330                 335 aaa act tta ggt gaa gct ggt att cca gtt ggt cct gtc ctt gat tgg       1056
Lys Thr Leu Gly Glu Ala Gly Ile Pro Val Gly Pro Val Leu Asp Trp
            340                 345                 350 cat gaa ctt gaa aat gat cca gac ttg aac tca gat ggt aca att gta       1104
His Glu Leu Glu Asn Asp Pro Asp Leu Asn Ser Asp Gly Thr Ile Val
        355                 360                 365 act atc gat caa ggt ggt aat cgt ggt aaa ttc aag act att ggt tta       1152
Thr Ile Asp Gln Gly Gly Asn Arg Gly Lys Phe Lys Thr Ile Gly Leu
    370                 375                 380 cca ttt act ctt gct aac tac aag cct gac tat aag cgt gct cca gac       1200
Pro Phe Thr Leu Ala Asn Tyr Lys Pro Asp Tyr Lys Arg Ala Pro Asp
385                 390                 395                 400 ctt ggt gaa aat aac aaa gaa att ttg tct tca ctt ggt tat gat cca       1248
Leu Gly Glu Asn Asn Lys Glu Ile Leu Ser Ser Leu Gly Tyr Asp Pro
                405                 410                 415 gac caa att gag aaa tta act gaa gaa ggc gta att tct aag gct aaa       1296
Asp Gln Ile Glu Lys Leu Thr Glu Glu Gly Val Ile Ser Lys Ala Lys
            420                 425                 430 ggc cct aag aat cca cgt gtt caa gtt att aaa ggt gaa                   1335
Gly Pro Lys Asn Pro Arg Val Gln Val Ile Lys Gly Glu
        435                 440                 445

<210> SEQ ID NO 2
<211> LENGTH: 445
<212> TYPE: PRT
<213> ORGANISM: Lactobacillus Acidophilus
```

-continued

<400> SEQUENCE: 2

```
Met Thr Glu Glu Glu Asn Glu Tyr Ala Pro Leu Lys Gly Ile Lys Val
1               5                   10                  15

Val Asp Trp Thr Gln Val Gln Ser Gly Pro Ser Cys Thr Gln Ile Leu
            20                  25                  30

Ala Trp Leu Gly Ala Glu Val Ile Lys Ile Glu Arg Thr Asn Thr Gly
        35                  40                  45

Asp Pro Thr Arg Asn Glu Leu Leu Asp Ile Gln Asp Ser Trp Ser Leu
    50                  55                  60

Tyr Tyr Leu Gln Leu Asn Ala Asn Lys Lys Ser Leu Thr Leu Asn Ile
65                  70                  75                  80

Lys Ala Pro Glu Gly Lys Lys Ile Met Tyr Asp Leu Leu Lys Lys Ala
                85                  90                  95

Asp Ile Phe Val Glu Asn Ile Lys Pro Gly Ala Ala Glu Lys Ala Gly
            100                 105                 110

Tyr Gly Trp Glu Thr Val His Lys Leu Asn Pro Arg Leu Ile Met Ala
        115                 120                 125

Ser Leu Lys Gly Phe Asn Glu Gly Ser Arg Phe Ala Asn Val Lys Ala
    130                 135                 140

Phe Glu Pro Val Ala Gln Ala Ala Gly Gly Ala Ala Ser Ala Thr Gly
145                 150                 155                 160

Trp Asn Lys Gly Glu Phe Asn Val Pro Thr Gln Ser Ala Ala Ala Leu
                165                 170                 175

Gly Asp Ser Asn Ser Gly Met His Leu Thr Ile Ala Ile Leu Ala Ala
            180                 185                 190

Leu Met Gln Arg Glu His Thr Gly Glu Gly Thr Tyr Val Tyr Gln Ser
        195                 200                 205

Met Gln Asp Ala Val Leu Asn Leu Cys Arg Ile Lys Leu Arg Asp Gln
    210                 215                 220

Leu Met Leu Asp Asn Leu Gly Ala Leu Pro His Tyr Ala Val Tyr Pro
225                 230                 235                 240

Asn Tyr Lys Trp Gly Asp Ala Ile Pro Arg Ala Glu Asn Thr Glu Gly
                245                 250                 255

Gly Gln Val Ile Gly Trp Thr Tyr Lys Ala Lys Gly Trp Glu Thr Asp
            260                 265                 270

Pro Asn Ala Tyr Val Tyr Ile Val Gln Asn Ser Asn Lys Ser Trp
        275                 280                 285

Glu Ala Ile Ala Asn Thr Met Gly His Pro Glu Trp Ile Thr Asp Glu
    290                 295                 300

Arg Phe Gln Asp Trp Gln His Arg Gln Leu Asn Lys Glu Ala Leu Tyr
305                 310                 315                 320

Gln Cys Ile Glu Ser Tyr Thr Lys Asn Tyr Asp Lys Phe Glu Leu Thr
                325                 330                 335

Lys Thr Leu Gly Glu Ala Gly Ile Pro Val Gly Pro Val Leu Asp Trp
            340                 345                 350

His Glu Leu Glu Asn Asp Pro Asp Leu Asn Ser Asp Gly Thr Ile Val
        355                 360                 365

Thr Ile Asp Gln Gly Gly Asn Arg Gly Lys Phe Lys Thr Ile Gly Leu
    370                 375                 380

Pro Phe Thr Leu Ala Asn Tyr Lys Pro Asp Tyr Lys Arg Ala Pro Asp
385                 390                 395                 400

Leu Gly Glu Asn Asn Lys Glu Ile Leu Ser Ser Leu Gly Tyr Asp Pro
                405                 410                 415
```

```
                Asp Gln Ile Glu Lys Leu Thr Glu Glu Gly Val Ile Ser Lys Ala Lys
                            420                 425                 430

Gly Pro Lys Asn Pro Arg Val Gln Val Ile Lys Gly Glu
                            435                 440                 445

<210> SEQ ID NO 3
<211> LENGTH: 1707
<212> TYPE: DNA
<213> ORGANISM: Lactobacillus Acidophilus
<220> FEATURE:
<221> NAME/KEY: CDS
<222> LOCATION: (1)...(1707)

<400> SEQUENCE: 3 gtg gtt gat aca tca ctc act gga gca gca ctt tta atc gat gct tta          48
Met Val Asp Thr Ser Leu Thr Gly Ala Ala Leu Leu Ile Asp Ala Leu
  1               5                  10                  15 caa gct aac ggt tta aac aat atg tat ggt gtt gta ggt att cca gtt          96
Gln Ala Asn Gly Leu Asn Asn Met Tyr Gly Val Val Gly Ile Pro Val
             20                  25                  30 acc gac ttt gcc cgt tta gct caa cta aag ggt atg aaa tat tat gga         144
Thr Asp Phe Ala Arg Leu Ala Gln Leu Lys Gly Met Lys Tyr Tyr Gly
         35                  40                  45 ttt aga cgt gaa gat tca gct gta gat gca gct gct ggt gca ggc ttt         192
Phe Arg Arg Glu Asp Ser Ala Val Asp Ala Ala Ala Gly Ala Gly Phe
     50                  55                  60 att act ggt aag cct ggc gta gct tta act gta tct gca cct ggt ttc         240
Ile Thr Gly Lys Pro Gly Val Ala Leu Thr Val Ser Ala Pro Gly Phe
 65                  70                  75                  80 tta aat ggt ttg aca gct tta gca caa gct act aag aac tgc ttc cca         288
Leu Asn Gly Leu Thr Ala Leu Ala Gln Ala Thr Lys Asn Cys Phe Pro
                 85                  90                  95 tta att atg att tca ggt tca tca gat cgt cat att att gac ctg gat         336
Leu Ile Met Ile Ser Gly Ser Ser Asp Arg His Ile Ile Asp Leu Asp
            100                 105                 110 cgt gga gat tat gaa ggt ctt gat caa tat aat gtt gct aaa cca ttc         384
Arg Gly Asp Tyr Glu Gly Leu Asp Gln Tyr Asn Val Ala Lys Pro Phe
        115                 120                 125 tgt aaa gca gca tat cgt gtt gat cgc gca gaa gat atg gga cta gct         432
Cys Lys Ala Ala Tyr Arg Val Asp Arg Ala Glu Asp Met Gly Leu Ala
    130                 135                 140 gtt gct cgt gca gtg aga act gct gtt agt ggt cgt cca ggt ggt gtt         480
Val Ala Arg Ala Val Arg Thr Ala Val Ser Gly Arg Pro Gly Gly Val
145                 150                 155                 160 tac ttg gat ctt cct gca gca act gtc act gat aca gtt gca caa aag         528
Tyr Leu Asp Leu Pro Ala Ala Thr Val Thr Asp Thr Val Ala Gln Lys
                165                 170                 175 tca gat gct aat atc tac aaa gtt gta gat cca gct cca aag caa ttg         576
Ser Asp Ala Asn Ile Tyr Lys Val Val Asp Pro Ala Pro Lys Gln Leu
            180                 185                 190 cca tca gat gat gca atc aac cgt gcc gtg gaa tta tta aaa gat gca         624
Pro Ser Asp Asp Ala Ile Asn Arg Ala Val Glu Leu Leu Lys Asp Ala
        195                 200                 205 aaa cat cct gta att ctt ctt ggt aaa ggt tct gct tac gct caa agc         672
Lys His Pro Val Ile Leu Leu Gly Lys Gly Ser Ala Tyr Ala Gln Ser
    210                 215                 220 gaa gac gaa atc aga gaa tta gtt aat aag act aat atc cca ttc ttg         720
Glu Asp Glu Ile Arg Glu Leu Val Asn Lys Thr Asn Ile Pro Phe Leu
225                 230                 235                 240 cca atg tca atg gcc aaa ggt gtt gta cca gat gat tct cca gca tct         768
Pro Met Ser Met Ala Lys Gly Val Val Pro Asp Asp Ser Pro Ala Ser
                245                 250                 255
```

```
                                                                -continued gct gca tca gct cgt tca ttt aca ctt ggt caa gct gat gtt gta ctt      816
Ala Ala Ser Ala Arg Ser Phe Thr Leu Gly Gln Ala Asp Val Val Leu
        260                 265                 270 ttg atc ggt gca cgt ctt aat tgg atg ctt tca aac ggt gaa tct cca      864
Leu Ile Gly Ala Arg Leu Asn Trp Met Leu Ser Asn Gly Glu Ser Pro
            275                 280                 285 tta ttc agt gaa gac gcc aag ttt att caa gtt gat att gat gca act      912
Leu Phe Ser Glu Asp Ala Lys Phe Ile Gln Val Asp Ile Asp Ala Thr
290                 295                 300 gaa ttt gat tca aac aga aag att gat gct cca tta cag ggt gac att      960
Glu Phe Asp Ser Asn Arg Lys Ile Asp Ala Pro Leu Gln Gly Asp Ile
305                 310                 315                 320 aaa tct gta atg caa aaa tta aat tct gcc gct atc aat gct ggt gtt     1008
Lys Ser Val Met Gln Lys Leu Asn Ser Ala Ala Ile Asn Ala Gly Val
                325                 330                 335 aag gca cca aca gat tgg att aat gct att aag acc gaa agc gaa aag     1056
Lys Ala Pro Thr Asp Trp Ile Asn Ala Ile Lys Thr Glu Ser Glu Lys
            340                 345                 350 aac aat act aag ttt gct aaa aga att tca gct tca gaa gct aaa tca     1104
Asn Asn Thr Lys Phe Ala Lys Arg Ile Ser Ala Ser Glu Ala Lys Ser
        355                 360                 365 act tta ggc tac tac agc gca att gaa cca att aat gac tta atg caa     1152
Thr Leu Gly Tyr Tyr Ser Ala Ile Glu Pro Ile Asn Asp Leu Met Gln
370                 375                 380 aag cat cct gat act tat tta gta agt gaa ggt gcc aac act ttg gat     1200
Lys His Pro Asp Thr Tyr Leu Val Ser Glu Gly Ala Asn Thr Leu Asp
385                 390                 395                 400 att ggt cgt gac tta att ggt atg caa aag cct cgt cac cgt ctt gac     1248
Ile Gly Arg Asp Leu Ile Gly Met Gln Lys Pro Arg His Arg Leu Asp
                405                 410                 415 act ggt act tgg ggt gtt atg ggt gtt ggc atg ggt tat gcc att gct     1296
Thr Gly Thr Trp Gly Val Met Gly Val Gly Met Gly Tyr Ala Ile Ala
            420                 425                 430 gca gct att gaa act ggc aaa cca gtt att gcc ctt gaa ggt gac tca     1344
Ala Ala Ile Glu Thr Gly Lys Pro Val Ile Ala Leu Glu Gly Asp Ser
        435                 440                 445 gca ttt ggt ttt gat ggt atg gaa atg gaa act att tgc cgt tac cac     1392
Ala Phe Gly Phe Asp Gly Met Glu Met Glu Thr Ile Cys Arg Tyr His
450                 455                 460 tta cct gtt att gta gtt att att aac aac ggt ggt att tac aac ggt     1440
Leu Pro Val Ile Val Val Ile Ile Asn Asn Gly Gly Ile Tyr Asn Gly
465                 470                 475                 480 gat gtt aac gtt gtt cct gat caa cca ggc cct act gtc ttg gat cac     1488
Asp Val Asn Val Val Pro Asp Gln Pro Gly Pro Thr Val Leu Asp His
                485                 490                 495 aat gcc cac tat ggt gat atc tct aag gca ttc ggc ggt gat agc tac     1536
Asn Ala His Tyr Gly Asp Ile Ser Lys Ala Phe Gly Gly Asp Ser Tyr
            500                 505                 510 cgt gta aat aac tac gaa gaa atg aaa gat gct ctt gaa aaa gcg tat     1584
Arg Val Asn Asn Tyr Glu Glu Met Lys Asp Ala Leu Glu Lys Ala Tyr
        515                 520                 525 gaa tca ggt aac cca aca atc atc gat gct caa att cct gag tca atg     1632
Glu Ser Gly Asn Pro Thr Ile Ile Asp Ala Gln Ile Pro Glu Ser Met
530                 535                 540 ggt aaa gaa tca ggt cat atc ggc aac tta aac cca aag ttg gac tta     1680
Gly Lys Glu Ser Gly His Ile Gly Asn Leu Asn Pro Lys Leu Asp Leu
545                 550                 555                 560 agt tct ctt gaa gca aag gag aat aaa                                 1707
Ser Ser Leu Glu Ala Lys Glu Asn Lys
                565
```

<210> SEQ ID NO 4
<211> LENGTH: 569
<212> TYPE: PRT
<213> ORGANISM: Lactobacillus Acidophilus

<400> SEQUENCE: 4

```
Met Val Asp Thr Ser Leu Thr Gly Ala Ala Leu Leu Ile Asp Ala Leu
1               5                   10                  15

Gln Ala Asn Gly Leu Asn Asn Met Tyr Gly Val Val Gly Ile Pro Val
            20                  25                  30

Thr Asp Phe Ala Arg Leu Ala Gln Leu Lys Gly Met Lys Tyr Tyr Gly
        35                  40                  45

Phe Arg Arg Glu Asp Ser Ala Val Asp Ala Ala Gly Ala Gly Phe
    50                  55                  60

Ile Thr Gly Lys Pro Gly Val Ala Leu Thr Val Ser Ala Pro Gly Phe
65                  70                  75                  80

Leu Asn Gly Leu Thr Ala Leu Ala Gln Ala Thr Lys Asn Cys Phe Pro
                85                  90                  95

Leu Ile Met Ile Ser Gly Ser Ser Asp Arg His Ile Ile Asp Leu Asp
            100                 105                 110

Arg Gly Asp Tyr Glu Gly Leu Asp Gln Tyr Asn Val Ala Lys Pro Phe
        115                 120                 125

Cys Lys Ala Ala Tyr Arg Val Asp Arg Ala Glu Asp Met Gly Leu Ala
    130                 135                 140

Val Ala Arg Ala Val Arg Thr Ala Val Ser Gly Arg Pro Gly Gly Val
145                 150                 155                 160

Tyr Leu Asp Leu Pro Ala Ala Thr Val Thr Asp Thr Val Ala Gln Lys
                165                 170                 175

Ser Asp Ala Asn Ile Tyr Lys Val Val Asp Pro Ala Pro Lys Gln Leu
            180                 185                 190

Pro Ser Asp Asp Ala Ile Asn Arg Ala Val Glu Leu Leu Lys Asp Ala
        195                 200                 205

Lys His Pro Val Ile Leu Leu Gly Lys Gly Ser Ala Tyr Ala Gln Ser
    210                 215                 220

Glu Asp Glu Ile Arg Glu Leu Val Asn Lys Thr Asn Ile Pro Phe Leu
225                 230                 235                 240

Pro Met Ser Met Ala Lys Gly Val Val Pro Asp Asp Ser Pro Ala Ser
                245                 250                 255

Ala Ala Ser Ala Arg Ser Phe Thr Leu Gly Gln Ala Asp Val Val Leu
            260                 265                 270

Leu Ile Gly Ala Arg Leu Asn Trp Met Leu Ser Asn Gly Glu Ser Pro
        275                 280                 285

Leu Phe Ser Glu Asp Ala Lys Phe Ile Gln Val Asp Ile Asp Ala Thr
    290                 295                 300

Glu Phe Asp Ser Asn Arg Lys Ile Asp Ala Pro Leu Gln Gly Asp Ile
305                 310                 315                 320

Lys Ser Val Met Gln Lys Leu Asn Ser Ala Ala Ile Asn Ala Gly Val
                325                 330                 335

Lys Ala Pro Thr Asp Trp Ile Asn Ala Ile Lys Thr Glu Ser Glu Lys
            340                 345                 350

Asn Asn Thr Lys Phe Ala Lys Arg Ile Ser Ala Ser Glu Ala Lys Ser
        355                 360                 365

Thr Leu Gly Tyr Tyr Ser Ala Ile Glu Pro Ile Asn Asp Leu Met Gln
    370                 375                 380
```

```
Lys His Pro Asp Thr Tyr Leu Val Ser Glu Gly Ala Asn Thr Leu Asp
385                 390                 395                 400

Ile Gly Arg Asp Leu Ile Gly Met Gln Lys Pro Arg His Arg Leu Asp
            405                 410                 415

Thr Gly Thr Trp Gly Val Met Gly Val Gly Met Gly Tyr Ala Ile Ala
        420                 425                 430

Ala Ala Ile Glu Thr Gly Lys Pro Val Ile Ala Leu Glu Gly Asp Ser
            435                 440                 445

Ala Phe Gly Phe Asp Gly Met Glu Met Glu Thr Ile Cys Arg Tyr His
        450                 455                 460

Leu Pro Val Ile Val Ile Ile Asn Asn Gly Gly Ile Tyr Asn Gly
465                 470                 475                 480

Asp Val Asn Val Val Pro Asp Gln Pro Gly Pro Thr Val Leu Asp His
                485                 490                 495

Asn Ala His Tyr Gly Asp Ile Ser Lys Ala Phe Gly Gly Asp Ser Tyr
                500                 505                 510

Arg Val Asn Asn Tyr Glu Glu Met Lys Asp Ala Leu Glu Lys Ala Tyr
            515                 520                 525

Glu Ser Gly Asn Pro Thr Ile Ile Asp Ala Gln Ile Pro Glu Ser Met
                530                 535                 540

Gly Lys Glu Ser Gly His Ile Gly Asn Leu Asn Pro Lys Leu Asp Leu
545                 550                 555                 560

Ser Ser Leu Glu Ala Lys Glu Asn Lys
                565

<210> SEQ ID NO 5
<211> LENGTH: 561
<212> TYPE: DNA
<213> ORGANISM: Lactobacillus Acidophilus
<220> FEATURE:
<221> NAME/KEY: CDS
<222> LOCATION: (1)...(561)

<400> SEQUENCE: 5 atg acg att aaa att tat acc aaa gtt ggt gat aaa ggt tta act aag    48
Met Thr Ile Lys Ile Tyr Thr Lys Val Gly Asp Lys Gly Leu Thr Lys
  1               5                  10                  15 caa gtc act ggc aaa atg gta cct aag tat gat tta caa att gaa gca    96
Gln Val Thr Gly Lys Met Val Pro Lys Tyr Asp Leu Gln Ile Glu Ala
             20                  25                  30 tta ggc aat ata gat gaa tta caa tca tat ctg ggt gta gtt tta gct   144
Leu Gly Asn Ile Asp Glu Leu Gln Ser Tyr Leu Gly Val Val Leu Ala
         35                  40                  45 aat tta tct aat aat tgc cag aaa cta cgt aat gaa tta gaa aat gta   192
Asn Leu Ser Asn Asn Cys Gln Lys Leu Arg Asn Glu Leu Glu Asn Val
     50                  55                  60 caa cgt aac tta tac caa tta caa gcg gat att gta gta aaa aat cat   240
Gln Arg Asn Leu Tyr Gln Leu Gln Ala Asp Ile Val Val Lys Asn His
 65                  70                  75                  80 cat gaa att aat gaa agt aat gta gta caa cta gaa aat cgt att aat   288
His Glu Ile Asn Glu Ser Asn Val Val Gln Leu Glu Asn Arg Ile Asn
                 85                  90                  95 gaa tta aca ccc aaa ata ccg tat att cct gaa ttt atc ttg ccg ggt   336
Glu Leu Thr Pro Lys Ile Pro Tyr Ile Pro Glu Phe Ile Leu Pro Gly
            100                 105                 110 ggc aaa gtt aca ggc acc aat tta cag tat gcc aga aca gtt gca aga   384
Gly Lys Val Thr Gly Thr Asn Leu Gln Tyr Ala Arg Thr Val Ala Arg
        115                 120                 125
```

```
cgc gct gaa cgc tcc ttg gtc aag ttg agt ctc aat gaa caa aaa tta      432
Arg Ala Glu Arg Ser Leu Val Lys Leu Ser Leu Asn Glu Gln Lys Leu
    130                 135                 140 gct gat tgt gat ttg gaa tat atg aat cgc tta tcc gat tat ctt ttt      480
Ala Asp Cys Asp Leu Glu Tyr Met Asn Arg Leu Ser Asp Tyr Leu Phe
145                 150                 155                 160 ata ttg gga cgt tat gcc aat gta ctt gat ggt tat act gaa aaa aaa      528
Ile Leu Gly Arg Tyr Ala Asn Val Leu Asp Gly Tyr Thr Glu Lys Lys
                165                 170                 175 agt aaa gtt agg gat aaa aac cgt att aat ggc                          561
Ser Lys Val Arg Asp Lys Asn Arg Ile Asn Gly
            180                 185

<210> SEQ ID NO 6
<211> LENGTH: 187
<212> TYPE: PRT
<213> ORGANISM: Lactobacillus Acidophilus

<400> SEQUENCE: 6

Met Thr Ile Lys Ile Tyr Thr Lys Val Gly Asp Lys Gly Leu Thr Lys
1               5                   10                  15

Gln Val Thr Gly Lys Met Val Pro Lys Tyr Asp Leu Gln Ile Glu Ala
            20                  25                  30

Leu Gly Asn Ile Asp Glu Leu Gln Ser Tyr Leu Gly Val Val Leu Ala
        35                  40                  45

Asn Leu Ser Asn Asn Cys Gln Lys Leu Arg Asn Glu Leu Glu Asn Val
    50                  55                  60

Gln Arg Asn Leu Tyr Gln Leu Gln Ala Asp Ile Val Val Lys Asn His
65                  70                  75                  80

His Glu Ile Asn Glu Ser Asn Val Val Gln Leu Glu Asn Arg Ile Asn
                85                  90                  95

Glu Leu Thr Pro Lys Ile Pro Tyr Ile Pro Glu Phe Ile Leu Pro Gly
            100                 105                 110

Gly Lys Val Thr Gly Thr Asn Leu Gln Tyr Ala Arg Thr Val Ala Arg
        115                 120                 125

Arg Ala Glu Arg Ser Leu Val Lys Leu Ser Leu Asn Glu Gln Lys Leu
    130                 135                 140

Ala Asp Cys Asp Leu Glu Tyr Met Asn Arg Leu Ser Asp Tyr Leu Phe
145                 150                 155                 160

Ile Leu Gly Arg Tyr Ala Asn Val Leu Asp Gly Tyr Thr Glu Lys Lys
                165                 170                 175

Ser Lys Val Arg Asp Lys Asn Arg Ile Asn Gly
            180                 185

<210> SEQ ID NO 7
<211> LENGTH: 522
<212> TYPE: DNA
<213> ORGANISM: Lactobacillus Acidophilus
<220> FEATURE:
<221> NAME/KEY: CDS
<222> LOCATION: (1)...(522)

<400> SEQUENCE: 7 atg gtt act gag cga cta caa atc aga caa atc gca tta atg gcc atg      48
Met Val Thr Glu Arg Leu Gln Ile Arg Gln Ile Ala Leu Met Ala Met
1               5                   10                  15 ctt aca gca atg tgt gtg gtt tta cga att ttt aaa att att cct atc      96
Leu Thr Ala Met Cys Val Val Leu Arg Ile Phe Lys Ile Ile Pro Ile
            20                  25                  30 ccc aat gta caa cca gta act gat att tta atg att gtt aca ctt aat     144
```

```
Pro Asn Val Gln Pro Val Thr Asp Ile Leu Met Ile Val Thr Leu Asn
         35                  40                  45 tta ggt att ggt tca ggt att act tta gct aca tta aca atg cta att      192
Leu Gly Ile Gly Ser Gly Ile Thr Leu Ala Thr Leu Thr Met Leu Ile
 50                  55                  60 tcg aat att tat tta gga ttc ggt att tgg act att cct caa att tta      240
Ser Asn Ile Tyr Leu Gly Phe Gly Ile Trp Thr Ile Pro Gln Ile Leu
 65                  70                  75                  80 gca tac aca ggt tgt gta tta act gtg gct ttc ttt gct aaa ttt aca      288
Ala Tyr Thr Gly Cys Val Leu Thr Val Ala Phe Phe Ala Lys Phe Thr
                 85                  90                  95 cca ttg aaa aat tac ttt ttg tta caa gta gct tta gct aca ttt tta      336
Pro Leu Lys Asn Tyr Phe Leu Leu Gln Val Ala Leu Ala Thr Phe Leu
             100                 105                 110 ggt tgg gaa tac ggt ttt tta gta gac ctt ggt atg act att ttt ggc      384
Gly Trp Glu Tyr Gly Phe Leu Val Asp Leu Gly Met Thr Ile Phe Gly
         115                 120                 125 ggt tta tct gct ttc atc gct tat ctt att tct agt ttt gct ttt gat      432
Gly Leu Ser Ala Phe Ile Ala Tyr Leu Ile Ser Ser Phe Ala Phe Asp
     130                 135                 140 acc tat cat gcc att ggt aat ttt gct ttt tac ttt gtt tta tat aaa      480
Thr Tyr His Ala Ile Gly Asn Phe Ala Phe Tyr Phe Val Leu Tyr Lys
145                 150                 155                 160 cct gta act aag gca ctt gaa gca tat caa cgg agg ata att              522
Pro Val Thr Lys Ala Leu Glu Ala Tyr Gln Arg Arg Ile Ile
                 165                 170

<210> SEQ ID NO 8
<211> LENGTH: 174
<212> TYPE: PRT
<213> ORGANISM: Lactobacillus Acidophilus

<400> SEQUENCE: 8

Met Val Thr Glu Arg Leu Gln Ile Arg Gln Ile Ala Leu Met Ala Met
 1               5                  10                  15

Leu Thr Ala Met Cys Val Val Leu Arg Ile Phe Lys Ile Ile Pro Ile
             20                  25                  30

Pro Asn Val Gln Pro Val Thr Asp Ile Leu Met Ile Val Thr Leu Asn
         35                  40                  45

Leu Gly Ile Gly Ser Gly Ile Thr Leu Ala Thr Leu Thr Met Leu Ile
 50                  55                  60

Ser Asn Ile Tyr Leu Gly Phe Gly Ile Trp Thr Ile Pro Gln Ile Leu
 65                  70                  75                  80

Ala Tyr Thr Gly Cys Val Leu Thr Val Ala Phe Phe Ala Lys Phe Thr
                 85                  90                  95

Pro Leu Lys Asn Tyr Phe Leu Leu Gln Val Ala Leu Ala Thr Phe Leu
             100                 105                 110

Gly Trp Glu Tyr Gly Phe Leu Val Asp Leu Gly Met Thr Ile Phe Gly
         115                 120                 125

Gly Leu Ser Ala Phe Ile Ala Tyr Leu Ile Ser Ser Phe Ala Phe Asp
     130                 135                 140

Thr Tyr His Ala Ile Gly Asn Phe Ala Phe Tyr Phe Val Leu Tyr Lys
145                 150                 155                 160

Pro Val Thr Lys Ala Leu Glu Ala Tyr Gln Arg Arg Ile Ile
                 165                 170

<210> SEQ ID NO 9
<211> LENGTH: 261
<212> TYPE: DNA
```

```
<213> ORGANISM: Lactobacillus Acidophilus
<220> FEATURE:
<221> NAME/KEY: CDS
<222> LOCATION: (1)...(261)

<400> SEQUENCE: 9 ttg aaa caa ggt aaa aag act gta gat acc aaa tct gtt aaa att cct      48
Met Lys Gln Gly Lys Lys Thr Val Asp Thr Lys Ser Val Lys Ile Pro
 1               5                  10                  15 aag aaa aaa gct aag gta att aca ggt ctg aaa aaa gca tgg aaa gta      96
Lys Lys Lys Ala Lys Val Ile Thr Gly Leu Lys Lys Ala Trp Lys Val
                20                  25                  30 caa gaa act aaa ggc ttt att acc tca atc gat ggt aag aag caa aat     144
Gln Glu Thr Lys Gly Phe Ile Thr Ser Ile Asp Gly Lys Lys Gln Asn
            35                  40                  45 cct aag aag aag att tat tgg act tat aca att aac ggt aaa tgg gca     192
Pro Lys Lys Lys Ile Tyr Trp Thr Tyr Thr Ile Asn Gly Lys Trp Ala
        50                  55                  60 aat aaa ggt gcc gat caa caa gcc gtt gct aac aaa gac aaa gtt aaa     240
Asn Lys Gly Ala Asp Gln Gln Ala Val Ala Asn Lys Asp Lys Val Lys
 65                  70                  75                  80 ttc acg tta gac aag gtg aag                                          261
Phe Thr Leu Asp Lys Val Lys
                85

<210> SEQ ID NO 10
<211> LENGTH: 87
<212> TYPE: PRT
<213> ORGANISM: Lactobacillus Acidophilus

<400> SEQUENCE: 10

Met Lys Gln Gly Lys Lys Thr Val Asp Thr Lys Ser Val Lys Ile Pro
 1               5                  10                  15

Lys Lys Lys Ala Lys Val Ile Thr Gly Leu Lys Lys Ala Trp Lys Val
                20                  25                  30

Gln Glu Thr Lys Gly Phe Ile Thr Ser Ile Asp Gly Lys Lys Gln Asn
            35                  40                  45

Pro Lys Lys Lys Ile Tyr Trp Thr Tyr Thr Ile Asn Gly Lys Trp Ala
        50                  55                  60

Asn Lys Gly Ala Asp Gln Gln Ala Val Ala Asn Lys Asp Lys Val Lys
 65                  70                  75                  80

Phe Thr Leu Asp Lys Val Lys
                85

<210> SEQ ID NO 11
<211> LENGTH: 1152
<212> TYPE: DNA
<213> ORGANISM: Lactobacillus Acidophilus
<220> FEATURE:
<221> NAME/KEY: CDS
<222> LOCATION: (1)...(1152)

<400> SEQUENCE: 11 atg act tat tac att cat gca gat aaa ttt ttc cta gaa aat aga act      48
Met Thr Tyr Tyr Ile His Ala Asp Lys Phe Phe Leu Glu Asn Arg Thr
 1               5                  10                  15 gaa aat ggg ggc tat ctt gaa gtt caa gat gat ggt aaa ttt ggc ttt      96
Glu Asn Gly Gly Tyr Leu Glu Val Gln Asp Asp Gly Lys Phe Gly Phe
                20                  25                  30 ttc tat cct gaa act aaa aag cca gaa gga aaa atc ctc gac tac aaa     144
Phe Tyr Pro Glu Thr Lys Lys Pro Glu Gly Lys Ile Leu Asp Tyr Lys
            35                  40                  45
```

| | | |
|---|---|---|
| ggt aag tgg gtt gca cca ggc tta gtt gat acg cat att cat ggc tct<br>Gly Lys Trp Val Ala Pro Gly Leu Val Asp Thr His Ile His Gly Ser<br>50                           55                         60 | | 192 |
| ctt cgt gaa gat gta atg aag agt gac tgg gaa gga atc gat aaa att<br>Leu Arg Glu Asp Val Met Lys Ser Asp Trp Glu Gly Ile Asp Lys Ile<br>65                           70                       75                     80 | | 240 |
| tct caa ggt ttg ctt agt gca ggt gta act tca tgg ctt cca act aca<br>Ser Gln Gly Leu Leu Ser Ala Gly Val Thr Ser Trp Leu Pro Thr Thr<br>                       85                     90                     95 | | 288 |
| att acg gct gat agt gat act tta act aga att tgt aag atg ttt gca<br>Ile Thr Ala Asp Ser Asp Thr Leu Thr Arg Ile Cys Lys Met Phe Ala<br>                    100                  105                110 | | 336 |
| gat cac caa ggt caa gaa act ggg gca aaa att caa gga att cac ttt<br>Asp His Gln Gly Gln Glu Thr Gly Ala Lys Ile Gln Gly Ile His Phe<br>             115                  120                125 | | 384 |
| gaa ggc cca ttc ttt act gaa gag cat gcc ggt gct gaa aat cct aaa<br>Glu Gly Pro Phe Phe Thr Glu Glu His Ala Gly Ala Glu Asn Pro Lys<br>         130                  135                140 | | 432 |
| tat atg atg gat ccg gat att aat gtc ttt aac aaa tgg cgt gat gtt<br>Tyr Met Met Asp Pro Asp Ile Asn Val Phe Asn Lys Trp Arg Asp Val<br>145                        150                155                160 | | 480 |
| tcg aat ggc atg ctt tgc aag att tct atg gca cct gaa aga aaa ggt<br>Ser Asn Gly Met Leu Cys Lys Ile Ser Met Ala Pro Glu Arg Lys Gly<br>                    165                  170                175 | | 528 |
| tct aaa gaa ttt att cgt gaa gct gta aaa gaa ggc gta gtt att gca<br>Ser Lys Glu Phe Ile Arg Glu Ala Val Lys Glu Gly Val Val Ile Ala<br>             180                  185                190 | | 576 |
| ttg ggt cac tca agt gcc act ttt gaa gaa gct gtc gaa ggt gtt gaa<br>Leu Gly His Ser Ser Ala Thr Phe Glu Glu Ala Val Glu Gly Val Glu<br>         195                  200                205 | | 624 |
| gca ggt gca acg atg ttt acg cat act ttt aac ggg atg cca gat cca<br>Ala Gly Ala Thr Met Phe Thr His Thr Phe Asn Gly Met Pro Asp Pro<br>210                        215                220 | | 672 |
| agt cat cat acg cca tca att tca aat gct gca atg gcc ttg aat aat<br>Ser His His Thr Pro Ser Ile Ser Asn Ala Ala Met Ala Leu Asn Asn<br>225                        230                235                240 | | 720 |
| gta act gat gaa tta att tgt gac ggc cac cac gtt caa cca tca atg<br>Val Thr Asp Glu Leu Ile Cys Asp Gly His His Val Gln Pro Ser Met<br>                    245                  250                255 | | 768 |
| gct aaa gca tta att aat gca gtt ggt cca gag cac att gct ttg att<br>Ala Lys Ala Leu Ile Asn Ala Val Gly Pro Glu His Ile Ala Leu Ile<br>             260                  265                270 | | 816 |
| act gac tgt atg gaa gcc ggg atg atg cca gac ggc gac tac atg tta<br>Thr Asp Cys Met Glu Ala Gly Met Met Pro Asp Gly Asp Tyr Met Leu<br>         275                  280                285 | | 864 |
| ggg gaa ctt cca gtt tat gta aaa gat ggt atg gct cgc ctt aag gat<br>Gly Glu Leu Pro Val Tyr Val Lys Asp Gly Met Ala Arg Leu Lys Asp<br>290                        295                300 | | 912 |
| ggc gat aat tta gca ggt tca att ttg caa tta aaa caa gca att aag<br>Gly Asp Asn Leu Ala Gly Ser Ile Leu Gln Leu Lys Gln Ala Ile Lys<br>305                        310                315                320 | | 960 |
| aat gtt gtt gat tgg aat att gta act cca gaa aaa gct gtg ctg atg<br>Asn Val Val Asp Trp Asn Ile Val Thr Pro Glu Lys Ala Val Leu Met<br>                    325                  330                335 | | 1008 |
| gct agt tac gtt cct gct aag agt gct cat att ttg aat aag tgc ggt<br>Ala Ser Tyr Val Pro Ala Lys Ser Ala His Ile Leu Asn Lys Cys Gly<br>             340                  345                350 | | 1056 |
| act att gca cct gac aag gat gct gat ttc tta atc ttg aat cca gat<br>Thr Ile Ala Pro Asp Lys Asp Ala Asp Phe Leu Ile Leu Asn Pro Asp<br>         355                  360                365 | | 1104 |

```
atg acg ctt agt gag act tac atg aat ggt gaa tca aga tac aaa gct     1152
Met Thr Leu Ser Glu Thr Tyr Met Asn Gly Glu Ser Arg Tyr Lys Ala
    370                 375                 380

<210> SEQ ID NO 12
<211> LENGTH: 384
<212> TYPE: PRT
<213> ORGANISM: Lactobacillus Acidophilus

<400> SEQUENCE: 12

Met Thr Tyr Tyr Ile His Ala Asp Lys Phe Phe Leu Glu Asn Arg Thr
 1               5                  10                  15

Glu Asn Gly Gly Tyr Leu Glu Val Gln Asp Asp Gly Lys Phe Gly Phe
            20                  25                  30

Phe Tyr Pro Glu Thr Lys Lys Pro Glu Gly Lys Ile Leu Asp Tyr Lys
        35                  40                  45

Gly Lys Trp Val Ala Pro Gly Leu Val Asp Thr His Ile His Gly Ser
    50                  55                  60

Leu Arg Glu Asp Val Met Lys Ser Asp Trp Glu Gly Ile Asp Lys Ile
65                  70                  75                  80

Ser Gln Gly Leu Leu Ser Ala Gly Val Thr Ser Trp Leu Pro Thr Thr
                85                  90                  95

Ile Thr Ala Asp Ser Asp Thr Leu Thr Arg Ile Cys Lys Met Phe Ala
            100                 105                 110

Asp His Gln Gly Gln Glu Thr Gly Ala Lys Ile Gln Gly Ile His Phe
        115                 120                 125

Glu Gly Pro Phe Phe Thr Glu Glu His Ala Gly Ala Glu Asn Pro Lys
    130                 135                 140

Tyr Met Met Asp Pro Asp Ile Asn Val Phe Asn Lys Trp Arg Asp Val
145                 150                 155                 160

Ser Asn Gly Met Leu Cys Lys Ile Ser Met Ala Pro Glu Arg Lys Gly
                165                 170                 175

Ser Lys Glu Phe Ile Arg Glu Ala Val Lys Glu Gly Val Val Ile Ala
            180                 185                 190

Leu Gly His Ser Ser Ala Thr Phe Glu Glu Ala Val Glu Gly Val Glu
        195                 200                 205

Ala Gly Ala Thr Met Phe Thr His Thr Phe Asn Gly Met Pro Asp Pro
    210                 215                 220

Ser His His Thr Pro Ser Ile Ser Asn Ala Ala Met Ala Leu Asn Asn
225                 230                 235                 240

Val Thr Asp Glu Leu Ile Cys Asp Gly His His Val Gln Pro Ser Met
                245                 250                 255

Ala Lys Ala Leu Ile Asn Ala Val Gly Pro Glu His Ile Ala Leu Ile
            260                 265                 270

Thr Asp Cys Met Glu Ala Gly Met Met Pro Asp Gly Asp Tyr Met Leu
        275                 280                 285

Gly Glu Leu Pro Val Tyr Val Lys Asp Gly Met Ala Arg Leu Lys Asp
    290                 295                 300

Gly Asp Asn Leu Ala Gly Ser Ile Leu Gln Leu Lys Gln Ala Ile Lys
305                 310                 315                 320

Asn Val Val Asp Trp Asn Ile Val Thr Pro Glu Lys Ala Val Leu Met
                325                 330                 335

Ala Ser Tyr Val Pro Ala Lys Ser Ala His Ile Leu Asn Lys Cys Gly
            340                 345                 350

Thr Ile Ala Pro Asp Lys Asp Ala Asp Phe Leu Ile Leu Asn Pro Asp
        355                 360                 365
```

Met Thr Leu Ser Glu Thr Tyr Met Asn Gly Glu Ser Arg Tyr Lys Ala
       370                 375                 380

<210> SEQ ID NO 13
<211> LENGTH: 483
<212> TYPE: DNA
<213> ORGANISM: Lactobacillus Acidophilus
<220> FEATURE:
<221> NAME/KEY: CDS
<222> LOCATION: (1)...(483)

<400> SEQUENCE: 13

```
gtg gta aaa gaa agt att tta gtt cca gta gat ggt tca gaa tca gct      48
Met Val Lys Glu Ser Ile Leu Val Pro Val Asp Gly Ser Glu Ser Ala
 1               5                  10                  15 gaa aga gct ttt gat aaa gct gtt cgt gta ggt tta aga gat ggc gca      96
Glu Arg Ala Phe Asp Lys Ala Val Arg Val Gly Leu Arg Asp Gly Ala
             20                  25                  30 cat gtt gat gta ttg aat gtt att gat act cgt caa ttt atg ggt gaa     144
His Val Asp Val Leu Asn Val Ile Asp Thr Arg Gln Phe Met Gly Glu
         35                  40                  45 atg caa gat aca tta att tct ggt gat acc att tat caa atg act caa     192
Met Gln Asp Thr Leu Ile Ser Gly Asp Thr Ile Tyr Gln Met Thr Gln
 50                  55                  60 gac tct gag gaa tat ttg aag agc tta aag aaa tgg gca cac gat aat     240
Asp Ser Glu Glu Tyr Leu Lys Ser Leu Lys Lys Trp Ala His Asp Asn
 65                  70                  75                  80 ttt aac ttt gat gat att gat tat cac att cgt tac ggt agc cct aag     288
Phe Asn Phe Asp Asp Ile Asp Tyr His Ile Arg Tyr Gly Ser Pro Lys
                 85                  90                  95 cga att att tct tat gac ttc atc aaa gat cac cat aac aac tta atc     336
Arg Ile Ile Ser Tyr Asp Phe Ile Lys Asp His His Asn Asn Leu Ile
            100                 105                 110 gtt atg gga gca aca ggt ctt aat gcc gtt gaa aga atg ctt atg ggt     384
Val Met Gly Ala Thr Gly Leu Asn Ala Val Glu Arg Met Leu Met Gly
        115                 120                 125 tca gtt act gaa tat gta aat caa cat gct tta gct gat gtt tta att     432
Ser Val Thr Glu Tyr Val Asn Gln His Ala Leu Ala Asp Val Leu Ile
    130                 135                 140 gtt aaa aca gat atg gat aat agc cct gtt aag cca agt gtg aaa aaa     480
Val Lys Thr Asp Met Asp Asn Ser Pro Val Lys Pro Ser Val Lys Lys
145                 150                 155                 160 ggt                                                                  483
Gly
```

<210> SEQ ID NO 14
<211> LENGTH: 161
<212> TYPE: PRT
<213> ORGANISM: Lactobacillus Acidophilus

<400> SEQUENCE: 14

Met Val Lys Glu Ser Ile Leu Val Pro Val Asp Gly Ser Glu Ser Ala
 1               5                  10                  15

Glu Arg Ala Phe Asp Lys Ala Val Arg Val Gly Leu Arg Asp Gly Ala
             20                  25                  30

His Val Asp Val Leu Asn Val Ile Asp Thr Arg Gln Phe Met Gly Glu
         35                  40                  45

Met Gln Asp Thr Leu Ile Ser Gly Asp Thr Ile Tyr Gln Met Thr Gln
 50                  55                  60

Asp Ser Glu Glu Tyr Leu Lys Ser Leu Lys Lys Trp Ala His Asp Asn
 65                  70                  75                  80

```
Phe Asn Phe Asp Asp Ile Asp Tyr His Ile Arg Tyr Gly Ser Pro Lys
            85                  90                  95

Arg Ile Ile Ser Tyr Asp Phe Ile Lys Asp His His Asn Asn Leu Ile
            100                 105                 110

Val Met Gly Ala Thr Gly Leu Asn Ala Val Glu Arg Met Leu Met Gly
            115                 120                 125

Ser Val Thr Glu Tyr Val Asn Gln His Ala Leu Ala Asp Val Leu Ile
    130                 135                 140

Val Lys Thr Asp Met Asp Asn Ser Pro Val Lys Pro Ser Val Lys Lys
145                 150                 155                 160

Gly

<210> SEQ ID NO 15
<211> LENGTH: 984
<212> TYPE: DNA
<213> ORGANISM: Lactobacillus Acidophilus
<220> FEATURE:
<221> NAME/KEY: CDS
<222> LOCATION: (1)...(984)

<400> SEQUENCE: 15 atg acc tta atg tgt tct att gct gga att tat tta gca aaa ttg cca      48
Met Thr Leu Met Cys Ser Ile Ala Gly Ile Tyr Leu Ala Lys Leu Pro
1               5                   10                  15 tat gct aac ata att ggg gca ttg gta tta gca ctt ctg tta ggt att      96
Tyr Ala Asn Ile Ile Gly Ala Leu Val Leu Ala Leu Leu Leu Gly Ile
            20                  25                  30 ctc atg caa tta gca cca gag aag atg cgt aaa gaa gct tca agt ggt     144
Leu Met Gln Leu Ala Pro Glu Lys Met Arg Lys Glu Ala Ser Ser Gly
        35                  40                  45 atg agt ttt att tca aat aaa ttc tta aga tta gga att atc tta cta     192
Met Ser Phe Ile Ser Asn Lys Phe Leu Arg Leu Gly Ile Ile Leu Leu
    50                  55                  60 gga ttt aga ctt gat tta gaa aaa cta gct gct gca gga gtc aaa acc     240
Gly Phe Arg Leu Asp Leu Glu Lys Leu Ala Ala Ala Gly Val Lys Thr
65                  70                  75                  80 att tta gtt gcc gct ctt gct gtt gca ggg act att aca tta act tac     288
Ile Leu Val Ala Ala Leu Ala Val Ala Gly Thr Ile Thr Leu Thr Tyr
                85                  90                  95 tgg ctt agt cgc aaa ttt ggt gca gaa gat gaa ttg gca ttt tta tca     336
Trp Leu Ser Arg Lys Phe Gly Ala Glu Asp Glu Leu Ala Phe Leu Ser
            100                 105                 110 gca tgt gga tgt ggt gtc tgc ggt gca gca gcc gta atg ggg gtt tct     384
Ala Cys Gly Cys Gly Val Cys Gly Ala Ala Ala Val Met Gly Val Ser
        115                 120                 125 cct caa att aca gct gct agt gaa gag aga aaa aga gag aat gaa gtt     432
Pro Gln Ile Thr Ala Ala Ser Glu Glu Arg Lys Arg Glu Asn Glu Val
    130                 135                 140 tta gca gta gcg gtt gtc tgt gtg atg ggt aca gtt ttt act tta tta     480
Leu Ala Val Ala Val Val Cys Val Met Gly Thr Val Phe Thr Leu Leu
145                 150                 155                 160 gaa att gga ctt aag cca gtt ctt ggt tta act gat tct caa ttc ggc     528
Glu Ile Gly Leu Lys Pro Val Leu Gly Leu Thr Asp Ser Gln Phe Gly
                165                 170                 175 att gtt gcc ggt ggt tct ttg cac gaa att gct cat gcg gtt gct tca     576
Ile Val Ala Gly Gly Ser Leu His Glu Ile Ala His Ala Val Ala Ser
            180                 185                 190 ggt ggt gca ttt ggt aat atc agt tta gat agt gca tta atc atg aaa     624
Gly Gly Ala Phe Gly Asn Ile Ser Leu Asp Ser Ala Leu Ile Met Lys
        195                 200                 205
```

-continued

| | | |
|---|---|---|
| cta tct cgt gta att ctt tta gca cct gtg gca tta att atc ggc tat<br>Leu Ser Arg Val Ile Leu Leu Ala Pro Val Ala Leu Ile Ile Gly Tyr<br>210                          215                            220 | 672 |
| tta tac caa cgc cgc aca gct aag gta agt aca att gac agt act aca<br>Leu Tyr Gln Arg Arg Thr Ala Lys Val Ser Thr Ile Asp Ser Thr Thr<br>225                          230                          235                      240 | 720 |
| aag act ggc aaa ttg cca att cct tgg ttc tta gga gga ttt att tta<br>Lys Thr Gly Lys Leu Pro Ile Pro Trp Phe Leu Gly Gly Phe Ile Leu<br>                          245                          250                          255 | 768 |
| acc agt gtt tta ggt act tac tta cca ttc tct act agt tta tta gat<br>Thr Ser Val Leu Gly Thr Tyr Leu Pro Phe Ser Thr Ser Leu Leu Asp<br>                    260                          265                          270 | 816 |
| gct tta gta caa gta gcc tac atc ttt tta gga atg gct atg gcc gca<br>Ala Leu Val Gln Val Ala Tyr Ile Phe Leu Gly Met Ala Met Ala Ala<br>                275                          280                          285 | 864 |
| ttg ggc att tct gta aac ttc aaa gtt atc ttt aag cga gga gga gct<br>Leu Gly Ile Ser Val Asn Phe Lys Val Ile Phe Lys Arg Gly Gly Ala<br>290                          295                          300 | 912 |
| gta ttt ggt gct gcc gca att agt tct act tgt tta ttg att ttc atg<br>Val Phe Gly Ala Ala Ala Ile Ser Ser Thr Cys Leu Leu Ile Phe Met<br>305                          310                          315                      320 | 960 |
| att att atg agt aaa tta ttc ttt<br>Ile Ile Met Ser Lys Leu Phe Phe<br>                    325 | 984 |

<210> SEQ ID NO 16
<211> LENGTH: 328
<212> TYPE: PRT
<213> ORGANISM: Lactobacillus Acidophilus

<400> SEQUENCE: 16

Met Thr Leu Met Cys Ser Ile Ala Gly Ile Tyr Leu Ala Lys Leu Pro
1               5                   10                  15

Tyr Ala Asn Ile Ile Gly Ala Leu Val Leu Ala Leu Leu Leu Gly Ile
            20                  25                  30

Leu Met Gln Leu Ala Pro Glu Lys Met Arg Lys Glu Ala Ser Ser Gly
        35                  40                  45

Met Ser Phe Ile Ser Asn Lys Phe Leu Arg Leu Gly Ile Ile Leu Leu
    50                  55                  60

Gly Phe Arg Leu Asp Leu Glu Lys Leu Ala Ala Ala Gly Val Lys Thr
65                  70                  75                  80

Ile Leu Val Ala Ala Leu Ala Val Ala Gly Thr Ile Thr Leu Thr Tyr
                85                  90                  95

Trp Leu Ser Arg Lys Phe Gly Ala Glu Asp Glu Leu Ala Phe Leu Ser
            100                 105                 110

Ala Cys Gly Cys Gly Val Cys Gly Ala Ala Val Met Gly Val Ser
        115                 120                 125

Pro Gln Ile Thr Ala Ala Ser Glu Glu Arg Lys Arg Glu Asn Glu Val
    130                 135                 140

Leu Ala Val Ala Val Cys Val Met Gly Thr Val Phe Thr Leu Leu
145                 150                 155                 160

Glu Ile Gly Leu Lys Pro Val Leu Gly Leu Thr Asp Ser Gln Phe Gly
                165                 170                 175

Ile Val Ala Gly Gly Ser Leu His Glu Ile Ala His Ala Val Ala Ser
            180                 185                 190

Gly Gly Ala Phe Gly Asn Ile Ser Leu Asp Ser Ala Leu Ile Met Lys
        195                 200                 205

```
Leu Ser Arg Val Ile Leu Ala Pro Val Ala Leu Ile Gly Tyr
    210                 215                 220

Leu Tyr Gln Arg Arg Thr Ala Lys Val Ser Thr Ile Asp Ser Thr Thr
225                 230                 235                 240

Lys Thr Gly Lys Leu Pro Ile Pro Trp Phe Leu Gly Gly Phe Ile Leu
                245                 250                 255

Thr Ser Val Leu Gly Thr Tyr Leu Pro Phe Ser Thr Ser Leu Leu Asp
                260                 265                 270

Ala Leu Val Gln Val Ala Tyr Ile Phe Leu Gly Met Ala Met Ala Ala
            275                 280                 285

Leu Gly Ile Ser Val Asn Phe Lys Val Ile Phe Lys Arg Gly Gly Ala
        290                 295                 300

Val Phe Gly Ala Ala Ile Ser Ser Thr Cys Leu Leu Ile Phe Met
305                 310                 315                 320

Ile Ile Met Ser Lys Leu Phe Phe
                325
```

<210> SEQ ID NO 17
<211> LENGTH: 2271
<212> TYPE: DNA
<213> ORGANISM: Lactobacillus Acidophilus
<220> FEATURE:
<221> NAME/KEY: CDS
<222> LOCATION: (1)...(2271)

<400> SEQUENCE: 17

```
atg act gga aaa ttt gaa ggc tta act caa gcc gaa gcc gat aag cga      48
Met Thr Gly Lys Phe Glu Gly Leu Thr Gln Ala Glu Ala Asp Lys Arg
 1               5                  10                  15 ctt aaa gaa gat ggg tta aat gaa gta cct gaa cct gaa tat aat ttc      96
Leu Lys Glu Asp Gly Leu Asn Glu Val Pro Glu Pro Glu Tyr Asn Phe
                 20                  25                  30 ttt aag gaa ttc tta tct aag cta tgg aac ttg tct gct tgg att ctt     144
Phe Lys Glu Phe Leu Ser Lys Leu Trp Asn Leu Ser Ala Trp Ile Leu
             35                  40                  45 gaa gga gcg tta att ctt gaa tgt atc tta ggt aaa tgg gtt caa tct     192
Glu Gly Ala Leu Ile Leu Glu Cys Ile Leu Gly Lys Trp Val Gln Ser
         50                  55                  60 cta ttt gtt ttg tta atg ctc tta ttt gca gca ttt aac ggg gca tct     240
Leu Phe Val Leu Leu Met Leu Leu Phe Ala Ala Phe Asn Gly Ala Ser
 65                  70                  75                  80 aag aaa aag caa tca cgt cgc gtt tta gat act att tca cac caa ttg     288
Lys Lys Lys Gln Ser Arg Arg Val Leu Asp Thr Ile Ser His Gln Leu
                 85                  90                  95 aca cca acg gtt gcg gta aaa aga gat gga aac tgg atc aaa att gat     336
Thr Pro Thr Val Ala Val Lys Arg Asp Gly Asn Trp Ile Lys Ile Asp
                100                 105                 110 tct aaa caa tta gtt aaa ggt gac tta att tca tta caa cgt gga gat     384
Ser Lys Gln Leu Val Lys Gly Asp Leu Ile Ser Leu Gln Arg Gly Asp
            115                 120                 125 gtt tta gcc gct gac gtt gaa cta gtt gac ggc agt att gcc tgc gat     432
Val Leu Ala Ala Asp Val Glu Leu Val Asp Gly Ser Ile Ala Cys Asp
        130                 135                 140 gaa agt tca atc acc ggt gaa tca aaa cca gtt aaa aaa aat gta ggt     480
Glu Ser Ser Ile Thr Gly Glu Ser Lys Pro Val Lys Lys Asn Val Gly
145                 150                 155                 160 gat gct gcc tat gct ggt act aca att gtt gaa ggt gat ggc cta gca     528
Asp Ala Ala Tyr Ala Gly Thr Thr Ile Val Glu Gly Asp Gly Leu Ala
                165                 170                 175 att gtt act gca aca ggc aaa aat tca aga agt ggt aaa act atc aac     576
```

|  |  |
|---|---|
| Ile Val Thr Ala Thr Gly Lys Asn Ser Arg Ser Gly Lys Thr Ile Asn<br>                  180                       185                     190 |  |
| ttg att aat aat tct gct gct cca ggc cac tta caa caa tta tta acc<br>Leu Ile Asn Asn Ser Ala Ala Pro Gly His Leu Gln Gln Leu Leu Thr<br>          195                    200                   205 | 624 |
| aag att att tac tat ctt tgc cta ctt gat ggt gta ctt aca tta gtt<br>Lys Ile Ile Tyr Tyr Leu Cys Leu Leu Asp Gly Val Leu Thr Leu Val<br> 210                    215                    220 | 672 |
| atc atc att gcc tca ttc ttt aag gga ggc aac ttt gat act ttc att<br>Ile Ile Ile Ala Ser Phe Phe Lys Gly Gly Asn Phe Asp Thr Phe Ile<br>225                   230                   235                240 | 720 |
| aac atg tta cca ttc ctt gcg atg atg ttt att gcc tct att ccg gtt<br>Asn Met Leu Pro Phe Leu Ala Met Met Phe Ile Ala Ser Ile Pro Val<br>                  245                    250                    255 | 768 |
| gca atg cca tca act ttt gct tta tcc aac tca ttt gaa gca act cgc<br>Ala Met Pro Ser Thr Phe Ala Leu Ser Asn Ser Phe Glu Ala Thr Arg<br>                  260                    265                   270 | 816 |
| ttg agt aaa gaa ggg gtt tta act tct gat tta act ggt atc caa gat<br>Leu Ser Lys Glu Gly Val Leu Thr Ser Asp Leu Thr Gly Ile Gln Asp<br>        275                    280                    285 | 864 |
| gca gct aat ttg aat tta ttg cta ctt gat aaa aca gga aca att aca<br>Ala Ala Asn Leu Asn Leu Leu Leu Leu Asp Lys Thr Gly Thr Ile Thr<br> 290                    295                    300 | 912 |
| gaa aat aaa acc gct gtt acg agt tgg act gac cta agt agt tta cca<br>Glu Asn Lys Thr Ala Val Thr Ser Trp Thr Asp Leu Ser Ser Leu Pro<br>305                   310                   315                320 | 960 |
| gat aaa gaa gtt tta gct tta gct ggt agc gct aca gat aag cga aat<br>Asp Lys Glu Val Leu Ala Leu Ala Gly Ser Ala Thr Asp Lys Arg Asn<br>                  325                    330                   335 | 1008 |
| gca gga att att gat acc gca ata gat gaa aat cta aca gaa aac aac<br>Ala Gly Ile Ile Asp Thr Ala Ile Asp Glu Asn Leu Thr Glu Asn Asn<br>                    340                    345                   350 | 1056 |
| att cct ata atg acg gca gag aaa ttt act cca ttt acc tct gat acg<br>Ile Pro Ile Met Thr Ala Glu Lys Phe Thr Pro Phe Thr Ser Asp Thr<br>        355                    360                    365 | 1104 |
| gga tat tca atg tct att att gat ggt cat aat gtt aaa ctt ggt tct<br>Gly Tyr Ser Met Ser Ile Ile Asp Gly His Asn Val Lys Leu Gly Ser<br> 370                    375                    380 | 1152 |
| ttt aag caa tta tct tta att gat aaa aat gcc aat gaa aaa att gaa<br>Phe Lys Gln Leu Ser Leu Ile Asp Lys Asn Ala Asn Glu Lys Ile Glu<br>385                   390                   395                400 | 1200 |
| ggt atc aat ttc aaa gct ggt cga tcc gtt gct gtt tta att gat gac<br>Gly Ile Asn Phe Lys Ala Gly Arg Ser Val Ala Val Leu Ile Asp Asp<br>                  405                    410                   415 | 1248 |
| aag tta gct ggc gtc ttt atc ttg caa gat aag gta aga aaa gat tct<br>Lys Leu Ala Gly Val Phe Ile Leu Gln Asp Lys Val Arg Lys Asp Ser<br>                    420                    425                   430 | 1296 |
| aag gca gct tta gca gac ctc aaa aag cgt ggc gtt cgt cca att atg<br>Lys Ala Ala Leu Ala Asp Leu Lys Lys Arg Gly Val Arg Pro Ile Met<br>        435                    440                    445 | 1344 |
| tta act ggt gat aac caa aga act gct gca gct gtt gct gaa gaa gtt<br>Leu Thr Gly Asp Asn Gln Arg Thr Ala Ala Ala Val Ala Glu Glu Val<br> 450                     455                    460 | 1392 |
| ggc tta aat ggt caa gtt att tca att cac gat ttt aac gaa aat act<br>Gly Leu Asn Gly Gln Val Ile Ser Ile His Asp Phe Asn Glu Asn Thr<br>465                   470                   475                480 | 1440 |
| gat att gat gac cta gca ggt att gct gat gtt tta cca gaa gac aaa<br>Asp Ile Asp Asp Leu Ala Gly Ile Ala Asp Val Leu Pro Glu Asp Lys<br>                  485                    490                   495 | 1488 |
| ctt aat atg gta aaa ttt ttc cag caa aaa ggc tat att gtg gga atg | 1536 |

-continued

```
           Leu Asn Met Val Lys Phe Phe Gln Gln Lys Gly Tyr Ile Val Gly Met
                           500                 505                 510 acc ggt gat ggt gtt aac gat tct cct gct tta aag caa gct gaa gtt       1584
Thr Gly Asp Gly Val Asn Asp Ser Pro Ala Leu Lys Gln Ala Glu Val
            515                 520                 525 ggt att gca gtt tca aat gca gca gac gtt gct aaa cgt tct ggt aag       1632
Gly Ile Ala Val Ser Asn Ala Ala Asp Val Ala Lys Arg Ser Gly Lys
        530                 535                 540 atg gta ctt tta gat gat ggc tta ggt tca att gtt aaa att tta gat       1680
Met Val Leu Leu Asp Asp Gly Leu Gly Ser Ile Val Lys Ile Leu Asp
545                 550                 555                 560 gct ggt cac cgc gtt tac caa aga atg act act tgg tca tta acc aaa       1728
Ala Gly His Arg Val Tyr Gln Arg Met Thr Thr Trp Ser Leu Thr Lys
                565                 570                 575 ctt gcc aga act gct gaa tta act atg ttg cta acc ttt ggt tac tta       1776
Leu Ala Arg Thr Ala Glu Leu Thr Met Leu Leu Thr Phe Gly Tyr Leu
            580                 585                 590 ttc ttc aac tat att cca atg gca tta aac gca atg gtt att tac aca       1824
Phe Phe Asn Tyr Ile Pro Met Ala Leu Asn Ala Met Val Ile Tyr Thr
        595                 600                 605 atc atg aat aat atg gta acc atg atg atc ggt act gat aga act cat       1872
Ile Met Asn Asn Met Val Thr Met Met Ile Gly Thr Asp Arg Thr His
610                 615                 620 att act tac aag cct gaa aac tgg aac atg gca aaa tta gct aag atc       1920
Ile Thr Tyr Lys Pro Glu Asn Trp Asn Met Ala Lys Leu Ala Lys Ile
625                 630                 635                 640 gcc ttt tca tta gct gca ggt tgg aca att atc gga ttc atc ttt att       1968
Ala Phe Ser Leu Ala Ala Gly Trp Thr Ile Ile Gly Phe Ile Phe Ile
                645                 650                 655 tgg tac cta aat act cac ggt tgg agt cat ggt aca att tca aca atg       2016
Trp Tyr Leu Asn Thr His Gly Trp Ser His Gly Thr Ile Ser Thr Met
            660                 665                 670 gtt tat gtt tac cta gtg ctt agc gca atg tta atc gtc tta atc act       2064
Val Tyr Val Tyr Leu Val Leu Ser Ala Met Leu Ile Val Leu Ile Thr
        675                 680                 685 aga act cgt aaa tat ttc tgg caa gat tat cca tca aag atg gtc ggt       2112
Arg Thr Arg Lys Tyr Phe Trp Gln Asp Tyr Pro Ser Lys Met Val Gly
690                 695                 700 att gtc caa att gcc gat gta gca tta acc ttt atc ctt gct ctt tgc       2160
Ile Val Gln Ile Ala Asp Val Ala Leu Thr Phe Ile Leu Ala Leu Cys
705                 710                 715                 720 ggt tta gct atg gtc caa atc agc tgg caa aac tta tta atc aca ata       2208
Gly Leu Ala Met Val Gln Ile Ser Trp Gln Asn Leu Leu Ile Thr Ile
                725                 730                 735 att gtt gca gta att gca gct ata tta atc gat tta gtc tat cag cca       2256
Ile Val Ala Val Ile Ala Ala Ile Leu Ile Asp Leu Val Tyr Gln Pro
            740                 745                 750 gta atg aaa aat aga                                                   2271
Val Met Lys Asn Arg
        755

<210> SEQ ID NO 18
<211> LENGTH: 757
<212> TYPE: PRT
<213> ORGANISM: Lactobacillus Acidophilus

<400> SEQUENCE: 18

Met Thr Gly Lys Phe Glu Gly Leu Thr Gln Ala Glu Ala Asp Lys Arg
1               5                   10                  15

Leu Lys Glu Asp Gly Leu Asn Glu Val Pro Glu Pro Glu Tyr Asn Phe
            20                  25                  30
```

Phe Lys Glu Phe Leu Ser Lys Leu Trp Asn Leu Ser Ala Trp Ile Leu
            35                  40                  45

Glu Gly Ala Leu Ile Leu Glu Cys Ile Leu Gly Lys Trp Val Gln Ser
 50                  55                  60

Leu Phe Val Leu Leu Met Leu Leu Phe Ala Ala Phe Asn Gly Ala Ser
 65                  70                  75                  80

Lys Lys Lys Gln Ser Arg Arg Val Leu Asp Thr Ile Ser His Gln Leu
                 85                  90                  95

Thr Pro Thr Val Ala Val Lys Arg Asp Gly Asn Trp Ile Lys Ile Asp
            100                 105                 110

Ser Lys Gln Leu Val Lys Gly Asp Leu Ile Ser Leu Gln Arg Gly Asp
            115                 120                 125

Val Leu Ala Ala Asp Val Glu Leu Val Asp Gly Ser Ile Ala Cys Asp
 130                 135                 140

Glu Ser Ser Ile Thr Gly Glu Ser Lys Pro Val Lys Lys Asn Val Gly
145                 150                 155                 160

Asp Ala Ala Tyr Ala Gly Thr Thr Ile Val Glu Gly Asp Gly Leu Ala
                 165                 170                 175

Ile Val Thr Ala Thr Gly Lys Asn Ser Arg Ser Gly Lys Thr Ile Asn
            180                 185                 190

Leu Ile Asn Asn Ser Ala Ala Pro Gly His Leu Gln Gln Leu Leu Thr
            195                 200                 205

Lys Ile Ile Tyr Tyr Leu Cys Leu Leu Asp Gly Val Leu Thr Leu Val
            210                 215                 220

Ile Ile Ile Ala Ser Phe Phe Lys Gly Gly Asn Phe Asp Thr Phe Ile
225                 230                 235                 240

Asn Met Leu Pro Phe Leu Ala Met Met Phe Ile Ala Ser Ile Pro Val
                 245                 250                 255

Ala Met Pro Ser Thr Phe Ala Leu Ser Asn Ser Phe Glu Ala Thr Arg
            260                 265                 270

Leu Ser Lys Glu Gly Val Leu Thr Ser Asp Leu Thr Gly Ile Gln Asp
            275                 280                 285

Ala Ala Asn Leu Asn Leu Leu Leu Asp Lys Thr Gly Thr Ile Thr
            290                 295                 300

Glu Asn Lys Thr Ala Val Thr Ser Trp Thr Asp Leu Ser Ser Leu Pro
305                 310                 315                 320

Asp Lys Glu Val Leu Ala Leu Ala Gly Ser Ala Thr Asp Lys Arg Asn
                 325                 330                 335

Ala Gly Ile Ile Asp Thr Ala Ile Asp Glu Asn Leu Thr Glu Asn Asn
            340                 345                 350

Ile Pro Ile Met Thr Ala Glu Lys Phe Thr Pro Phe Thr Ser Asp Thr
            355                 360                 365

Gly Tyr Ser Met Ser Ile Ile Asp Gly His Asn Val Lys Leu Gly Ser
370                 375                 380

Phe Lys Gln Leu Ser Leu Ile Asp Lys Asn Ala Asn Glu Lys Ile Glu
385                 390                 395                 400

Gly Ile Asn Phe Lys Ala Gly Arg Ser Val Ala Val Leu Ile Asp Asp
                 405                 410                 415

Lys Leu Ala Gly Val Phe Ile Leu Gln Asp Lys Val Arg Lys Asp Ser
            420                 425                 430

Lys Ala Ala Leu Ala Asp Leu Lys Lys Arg Gly Val Arg Pro Ile Met
            435                 440                 445

Leu Thr Gly Asp Asn Gln Arg Thr Ala Ala Ala Val Ala Glu Glu Val

```
                    450             455             460
Gly Leu Asn Gly Gln Val Ile Ser Ile His Asp Phe Asn Glu Asn Thr
465                 470                 475                 480

Asp Ile Asp Asp Leu Ala Gly Ile Ala Asp Val Leu Pro Glu Asp Lys
                    485                 490                 495

Leu Asn Met Val Lys Phe Phe Gln Gln Lys Gly Tyr Ile Val Gly Met
                500                 505                 510

Thr Gly Asp Gly Val Asn Asp Ser Pro Ala Leu Lys Gln Ala Glu Val
            515                 520                 525

Gly Ile Ala Val Ser Asn Ala Ala Asp Val Ala Lys Arg Ser Gly Lys
        530                 535                 540

Met Val Leu Leu Asp Asp Gly Leu Gly Ser Ile Val Lys Ile Leu Asp
545                 550                 555                 560

Ala Gly His Arg Val Tyr Gln Arg Met Thr Thr Trp Ser Leu Thr Lys
                565                 570                 575

Leu Ala Arg Thr Ala Glu Leu Thr Met Leu Thr Phe Gly Tyr Leu
                580                 585                 590

Phe Phe Asn Tyr Ile Pro Met Ala Leu Asn Ala Met Val Ile Tyr Thr
            595                 600                 605

Ile Met Asn Asn Met Val Thr Met Met Ile Gly Thr Asp Arg Thr His
610                 615                 620

Ile Thr Tyr Lys Pro Glu Asn Trp Asn Met Ala Lys Leu Ala Lys Ile
625                 630                 635                 640

Ala Phe Ser Leu Ala Ala Gly Trp Thr Ile Gly Phe Ile Phe Ile
                645                 650                 655

Trp Tyr Leu Asn Thr His Gly Trp Ser His Gly Thr Ile Ser Thr Met
                660                 665                 670

Val Tyr Val Tyr Leu Val Leu Ser Ala Met Leu Ile Val Leu Ile Thr
            675                 680                 685

Arg Thr Arg Lys Tyr Phe Trp Gln Asp Tyr Pro Ser Lys Met Val Gly
            690                 695                 700

Ile Val Gln Ile Ala Asp Val Ala Leu Thr Phe Ile Leu Ala Leu Cys
705                 710                 715                 720

Gly Leu Ala Met Val Gln Ile Ser Trp Gln Asn Leu Leu Ile Thr Ile
                725                 730                 735

Ile Val Ala Val Ile Ala Ile Leu Ile Asp Leu Val Tyr Gln Pro
            740                 745                 750

Val Met Lys Asn Arg
        755

<210> SEQ ID NO 19
<211> LENGTH: 834
<212> TYPE: DNA
<213> ORGANISM: Lactobacillus Acidophilus
<220> FEATURE:
<221> NAME/KEY: CDS
<222> LOCATION: (1)...(834)

<400> SEQUENCE: 19 atg aaa aac att aaa caa cgt tcc tgg ata aaa ggg cta gta ttt tta      48
Met Lys Asn Ile Lys Gln Arg Ser Trp Ile Lys Gly Leu Val Phe Leu
  1               5                  10                  15 gcg gga ctt gaa att ata gca ata gca att aat ttc ttt tat gga cca      96
Ala Gly Leu Glu Ile Ile Ala Ile Ala Ile Asn Phe Phe Tyr Gly Pro
             20                  25                  30 atc aat att gct gct gga gga tct acc ggt att tca att ttg att gat     144
Ile Asn Ile Ala Ala Gly Gly Ser Thr Gly Ile Ser Ile Leu Ile Asp
```

```
                35                  40                  45
gct gtt tgg gga gtt aac cgc tca ata act gtt ttt att gtt aat ggt    192
Ala Val Trp Gly Val Asn Arg Ser Ile Thr Val Phe Ile Val Asn Gly
    50                  55                  60 tta atg ctg ata tta gcc gca att ttt tta ggt aaa aaa gta acc aaa    240
Leu Met Leu Ile Leu Ala Ala Ile Phe Leu Gly Lys Lys Val Thr Lys
 65                  70                  75                  80 aat gtg gca gca ggt agt ttg tta tta cca atc tta atg gag att acc    288
Asn Val Ala Ala Gly Ser Leu Leu Leu Pro Ile Leu Met Glu Ile Thr
                 85                  90                  95 cct agt ttt gaa ata act agc aat aaa ttg cta gct gta ata tat ggt    336
Pro Ser Phe Glu Ile Thr Ser Asn Lys Leu Leu Ala Val Ile Tyr Gly
            100                 105                 110 gga gct tta atg gga ttt ggt att tca ctt ctt tat cgt gtt aat gca    384
Gly Ala Leu Met Gly Phe Gly Ile Ser Leu Leu Tyr Arg Val Asn Ala
        115                 120                 125 tca agt ggt gga aca acg atc cca ccg atg att tta aaa aag tat ttt    432
Ser Ser Gly Gly Thr Thr Ile Pro Pro Met Ile Leu Lys Lys Tyr Phe
    130                 135                 140 tat ttg aat cca gca acc acg ctt aca att att gac atg att ata att    480
Tyr Leu Asn Pro Ala Thr Thr Leu Thr Ile Ile Asp Met Ile Ile Ile
145                 150                 155                 160 ttc ttg aat att ttc gta gat ggt tgg aat gct ttt ctt tta gca gct    528
Phe Leu Asn Ile Phe Val Asp Gly Trp Asn Ala Phe Leu Leu Ala Ala
                165                 170                 175 ttg tca caa gta gtt acg gca att acg atg cgc tac acg gag act ggt    576
Leu Ser Gln Val Val Thr Ala Ile Thr Met Arg Tyr Thr Glu Thr Gly
            180                 185                 190 ttt gat aaa aag tat caa gta cgt att atg tca aat aaa tat ctt gaa    624
Phe Asp Lys Lys Tyr Gln Val Arg Ile Met Ser Asn Lys Tyr Leu Glu
        195                 200                 205 caa att cag gat atg tta aaa gac gag tat caa gga tta aca att tat    672
Gln Ile Gln Asp Met Leu Lys Asp Glu Tyr Gln Gly Leu Thr Ile Tyr
    210                 215                 220 aat gtt gtt ggt ggc tat agc gat gaa gat aaa cgt cag ttg tta atc    720
Asn Val Val Gly Gly Tyr Ser Asp Glu Asp Lys Arg Gln Leu Leu Ile
225                 230                 235                 240 gtg gtt gat acg cgt gat tat ggt cca ttg att tct aaa att cat gca    768
Val Val Asp Thr Arg Asp Tyr Gly Pro Leu Ile Ser Lys Ile His Ala
                245                 250                 255 att gat caa gat gca ttt att att act gaa aat gta gct aaa gtt cat    816
Ile Asp Gln Asp Ala Phe Ile Ile Thr Glu Asn Val Ala Lys Val His
            260                 265                 270 ggt ggt caa tgg ggg ata                                            834
Gly Gly Gln Trp Gly Ile
        275

<210> SEQ ID NO 20
<211> LENGTH: 278
<212> TYPE: PRT
<213> ORGANISM: Lactobacillus Acidophilus

<400> SEQUENCE: 20

Met Lys Asn Ile Lys Gln Arg Ser Trp Ile Lys Gly Leu Val Phe Leu
 1               5                  10                  15

Ala Gly Leu Glu Ile Ile Ala Ile Ala Ile Asn Phe Phe Tyr Gly Pro
            20                  25                  30

Ile Asn Ile Ala Ala Gly Gly Ser Thr Gly Ile Ser Ile Leu Ile Asp
        35                  40                  45

Ala Val Trp Gly Val Asn Arg Ser Ile Thr Val Phe Ile Val Asn Gly
```

```
            50                  55                  60
Leu Met Leu Ile Leu Ala Ala Ile Phe Leu Gly Lys Lys Val Thr Lys
 65                  70                  75                  80

Asn Val Ala Ala Gly Ser Leu Leu Pro Ile Leu Met Glu Ile Thr
                 85                  90                  95

Pro Ser Phe Glu Ile Thr Ser Asn Lys Leu Leu Ala Val Ile Tyr Gly
            100                 105                 110

Gly Ala Leu Met Gly Phe Gly Ile Ser Leu Leu Tyr Arg Val Asn Ala
            115                 120                 125

Ser Ser Gly Gly Thr Thr Ile Pro Pro Met Ile Leu Lys Lys Tyr Phe
130                 135                 140

Tyr Leu Asn Pro Ala Thr Thr Leu Thr Ile Ile Asp Met Ile Ile
145                 150                 155                 160

Phe Leu Asn Ile Phe Val Asp Gly Trp Asn Ala Phe Leu Leu Ala Ala
                165                 170                 175

Leu Ser Gln Val Val Thr Ala Ile Thr Met Arg Tyr Thr Glu Thr Gly
            180                 185                 190

Phe Asp Lys Lys Tyr Gln Val Arg Ile Met Ser Asn Lys Tyr Leu Glu
            195                 200                 205

Gln Ile Gln Asp Met Leu Lys Asp Glu Tyr Gln Gly Leu Thr Ile Tyr
    210                 215                 220

Asn Val Val Gly Gly Tyr Ser Asp Glu Asp Lys Arg Gln Leu Leu Ile
225                 230                 235                 240

Val Val Asp Thr Arg Asp Tyr Gly Pro Leu Ile Ser Lys Ile His Ala
                245                 250                 255

Ile Asp Gln Asp Ala Phe Ile Ile Thr Glu Asn Val Ala Lys Val His
            260                 265                 270

Gly Gly Gln Trp Gly Ile
            275

<210> SEQ ID NO 21
<211> LENGTH: 2001
<212> TYPE: DNA
<213> ORGANISM: Lactobacillus Acidophilus
<220> FEATURE:
<221> NAME/KEY: CDS
<222> LOCATION: (1)...(2001)

<400> SEQUENCE: 21 atg aca caa tta tca cgt ttt ctt tat ggt ggt gat tat aat cct gac    48
Met Thr Gln Leu Ser Arg Phe Leu Tyr Gly Gly Asp Tyr Asn Pro Asp
  1               5                  10                  15 caa tgg cca gaa gaa aca tgg tcg aaa gat att cac gta ttt aaa aag    96
Gln Trp Pro Glu Glu Thr Trp Ser Lys Asp Ile His Val Phe Lys Lys
             20                  25                  30 gcg gat att aat tcg gca acg att aac att ttt tct tgg gca ttg ctt   144
Ala Asp Ile Asn Ser Ala Thr Ile Asn Ile Phe Ser Trp Ala Leu Leu
         35                  40                  45 gaa cca aga gaa gga aaa tat aat ttc tca aaa tta gat aaa gtt gta   192
Glu Pro Arg Glu Gly Lys Tyr Asn Phe Ser Lys Leu Asp Lys Val Val
     50                  55                  60 caa caa tta tct gat gct aac ttt gat att gtg atg gga aca gcc aca   240
Gln Gln Leu Ser Asp Ala Asn Phe Asp Ile Val Met Gly Thr Ala Thr
 65                  70                  75                  80 gca gcg atg cca gct tgg atg ttt aaa aaa tat ccc gat att gcc aga   288
Ala Ala Met Pro Ala Trp Met Phe Lys Lys Tyr Pro Asp Ile Ala Arg
                 85                  90                  95 gta gat tat caa gac aga cgt cat gta ttt ggt cag cgg cat aac ttc   336
```

-continued

| | | | | | | | | | | | | | | |
|---|---|---|---|---|---|---|---|---|---|---|---|---|---|---|
| | Val | Asp | Tyr | Gln | Asp | Arg | Arg | His | Val | Phe | Gly | Gln | Arg | His | Asn | Phe |
| | | | 100 | | | | | 105 | | | | | 110 | | |

| tgt | cct | aat | agc | tca | aat | tat | caa | aga | tta | gct | ggt | gaa | tta | gta | aag | 384 |
|---|---|---|---|---|---|---|---|---|---|---|---|---|---|---|---|---|
| Cys | Pro | Asn | Ser | Ser | Asn | Tyr | Gln | Arg | Leu | Ala | Gly | Glu | Leu | Val | Lys | |
| | | | 115 | | | | | 120 | | | | | 125 | | | |

| cag | tta | gtt | gaa | cgc | tac | aag | gat | aat | aag | cat | atc | gta | gtt | tgg | cac | 432 |
|---|---|---|---|---|---|---|---|---|---|---|---|---|---|---|---|---|
| Gln | Leu | Val | Glu | Arg | Tyr | Lys | Asp | Asn | Lys | His | Ile | Val | Val | Trp | His | |
| | 130 | | | | | 135 | | | | | 140 | | | | | |

| ata | aac | aat | gaa | tat | ggt | ggc | aac | tgt | tat | tgt | gag | aat | tgt | caa | aac | 480 |
|---|---|---|---|---|---|---|---|---|---|---|---|---|---|---|---|---|
| Ile | Asn | Asn | Glu | Tyr | Gly | Gly | Asn | Cys | Tyr | Cys | Glu | Asn | Cys | Gln | Asn | |
| 145 | | | | | 150 | | | | | 155 | | | | | 160 | |

| gct | ttt | aga | aaa | tgg | ttg | aag | aat | aaa | tat | aag | acc | gtt | gaa | ggt | ctt | 528 |
|---|---|---|---|---|---|---|---|---|---|---|---|---|---|---|---|---|
| Ala | Phe | Arg | Lys | Trp | Leu | Lys | Asn | Lys | Tyr | Lys | Thr | Val | Glu | Gly | Leu | |
| | | | | 165 | | | | | 170 | | | | | 175 | | |

| aac | aag | gca | tgg | aat | atg | aat | gta | tgg | agc | cat | acg | att | tat | gac | tgg | 576 |
|---|---|---|---|---|---|---|---|---|---|---|---|---|---|---|---|---|
| Asn | Lys | Ala | Trp | Asn | Met | Asn | Val | Trp | Ser | His | Thr | Ile | Tyr | Asp | Trp | |
| | | | 180 | | | | | 185 | | | | | 190 | | | |

| gat | gaa | att | gtt | gtt | cct | aat | gag | tta | ggg | gat | gta | tgg | gga | ata | gaa | 624 |
|---|---|---|---|---|---|---|---|---|---|---|---|---|---|---|---|---|
| Asp | Glu | Ile | Val | Val | Pro | Asn | Glu | Leu | Gly | Asp | Val | Trp | Gly | Ile | Glu | |
| | | | 195 | | | | | 200 | | | | | 205 | | | |

| ggt | agt | gaa | act | att | gta | gct | ggt | ctt | tca | att | gat | tat | ctg | cgt | ttt | 672 |
|---|---|---|---|---|---|---|---|---|---|---|---|---|---|---|---|---|
| Gly | Ser | Glu | Thr | Ile | Val | Ala | Gly | Leu | Ser | Ile | Asp | Tyr | Leu | Arg | Phe | |
| | 210 | | | | | 215 | | | | | 220 | | | | | |

| caa | tct | gaa | agt | atg | caa | aat | ctt | ttc | aag | atg | gaa | aag | aag | att | att | 720 |
|---|---|---|---|---|---|---|---|---|---|---|---|---|---|---|---|---|
| Gln | Ser | Glu | Ser | Met | Gln | Asn | Leu | Phe | Lys | Met | Glu | Lys | Lys | Ile | Ile | |
| 225 | | | | | 230 | | | | | 235 | | | | | 240 | |

| aaa | aaa | tat | gat | ccg | gaa | act | cct | gta | acg | act | aat | ttc | cat | ggt | ttg | 768 |
|---|---|---|---|---|---|---|---|---|---|---|---|---|---|---|---|---|
| Lys | Lys | Tyr | Asp | Pro | Glu | Thr | Pro | Val | Thr | Thr | Asn | Phe | His | Gly | Leu | |
| | | | | 245 | | | | | 250 | | | | | 255 | | |

| cct | aac | aag | atg | gtt | gat | tat | caa | aag | tgg | gca | aaa | ggt | caa | gat | att | 816 |
|---|---|---|---|---|---|---|---|---|---|---|---|---|---|---|---|---|
| Pro | Asn | Lys | Met | Val | Asp | Tyr | Gln | Lys | Trp | Ala | Lys | Gly | Gln | Asp | Ile | |
| | | | 260 | | | | | 265 | | | | | 270 | | | |

| att | tca | tat | gat | agt | tat | cca | act | tat | gat | gct | cct | gca | tat | aaa | gcg | 864 |
|---|---|---|---|---|---|---|---|---|---|---|---|---|---|---|---|---|
| Ile | Ser | Tyr | Asp | Ser | Tyr | Pro | Thr | Tyr | Asp | Ala | Pro | Ala | Tyr | Lys | Ala | |
| | | 275 | | | | | 280 | | | | | 285 | | | | |

| gca | ttc | ttg | tat | gac | tta | atg | cga | agc | ttg | aaa | cat | cag | cca | ttt | atg | 912 |
|---|---|---|---|---|---|---|---|---|---|---|---|---|---|---|---|---|
| Ala | Phe | Leu | Tyr | Asp | Leu | Met | Arg | Ser | Leu | Lys | His | Gln | Pro | Phe | Met | |
| 290 | | | | | 295 | | | | | 300 | | | | | | |

| tta | atg | gaa | tct | gcg | cct | tca | caa | gtt | aac | tgg | caa | cca | tat | agt | ccg | 960 |
|---|---|---|---|---|---|---|---|---|---|---|---|---|---|---|---|---|
| Leu | Met | Glu | Ser | Ala | Pro | Ser | Gln | Val | Asn | Trp | Gln | Pro | Tyr | Ser | Pro | |
| 305 | | | | | 310 | | | | | 315 | | | | | 320 | |

| ctt | aag | cgg | cct | gga | caa | atg | gaa | gca | act | gaa | ttt | caa | gct | gta | gcc | 1008 |
|---|---|---|---|---|---|---|---|---|---|---|---|---|---|---|---|---|
| Leu | Lys | Arg | Pro | Gly | Gln | Met | Glu | Ala | Thr | Glu | Phe | Gln | Ala | Val | Ala | |
| | | | | 325 | | | | | 330 | | | | | 335 | | |

| cat | ggt | gct | gat | acg | gta | caa | ttc | ttc | caa | tta | aaa | caa | gca | gtt | ggt | 1056 |
|---|---|---|---|---|---|---|---|---|---|---|---|---|---|---|---|---|
| His | Gly | Ala | Asp | Thr | Val | Gln | Phe | Phe | Gln | Leu | Lys | Gln | Ala | Val | Gly | |
| | | | 340 | | | | | 345 | | | | | 350 | | | |

| ggc | tcc | gaa | aaa | ttc | cac | agt | gca | gtt | att | gct | cat | tcg | caa | aga | acc | 1104 |
|---|---|---|---|---|---|---|---|---|---|---|---|---|---|---|---|---|
| Gly | Ser | Glu | Lys | Phe | His | Ser | Ala | Val | Ile | Ala | His | Ser | Gln | Arg | Thr | |
| | | 355 | | | | | 360 | | | | | 365 | | | | |

| gat | act | aga | gta | ttt | aaa | gaa | cta | gct | gat | tta | ggg | aag | aaa | tta | aag | 1152 |
|---|---|---|---|---|---|---|---|---|---|---|---|---|---|---|---|---|
| Asp | Thr | Arg | Val | Phe | Lys | Glu | Leu | Ala | Asp | Leu | Gly | Lys | Lys | Leu | Lys | |
| 370 | | | | | 375 | | | | | 380 | | | | | | |

| aat | gct | gga | cca | acg | att | tta | ggg | tca | aag | act | aag | gca | aag | gtc | gca | 1200 |
|---|---|---|---|---|---|---|---|---|---|---|---|---|---|---|---|---|
| Asn | Ala | Gly | Pro | Thr | Ile | Leu | Gly | Ser | Lys | Thr | Lys | Ala | Lys | Val | Ala | |
| 385 | | | | | 390 | | | | | 395 | | | | | 400 | |

| att | gtc | ttt | gat | tgg | agt | aac | ttc | tgg | tcg | tat | gag | tat | gtg | gac | gga | 1248 |
|---|---|---|---|---|---|---|---|---|---|---|---|---|---|---|---|---|
| Ile | Val | Phe | Asp | Trp | Ser | Asn | Phe | Trp | Ser | Tyr | Glu | Tyr | Val | Asp | Gly | |
| | | | | 405 | | | | | 410 | | | | | 415 | | |

| att | act | caa | gat | ttg | aac | tat | gta | gat | tct | att | ctt | gat | tac | tac | cgt | 1296 |

-continued

| | | |
|---|---|---|
| Ile Thr Gln Asp Leu Asn Tyr Val Asp Ser Ile Leu Asp Tyr Tyr Arg<br>    420                 425                 430 | | |
| cag ttc tat gaa cgc aat att cca act gac atc att ggt gta gac gat<br>Gln Phe Tyr Glu Arg Asn Ile Pro Thr Asp Ile Ile Gly Val Asp Asp<br>        435                 440                 445 | | 1344 |
| gac ttt agc aac tat gat ttg gtt gta gcg cct gtg ctt tat atg gtt<br>Asp Phe Ser Asn Tyr Asp Leu Val Val Ala Pro Val Leu Tyr Met Val<br>    450                 455                 460 | | 1392 |
| aaa cat ggt ctt gat aag aag atc aac gac tat gtt gaa aac ggt ggt<br>Lys His Gly Leu Asp Lys Lys Ile Asn Asp Tyr Val Glu Asn Gly Gly<br>465                 470                 475                 480 | | 1440 |
| aac ttt gtc act act tat atg tca ggc atg gtg aac tca tca gat aat<br>Asn Phe Val Thr Thr Tyr Met Ser Gly Met Val Asn Ser Ser Asp Asn<br>                485                 490                 495 | | 1488 |
| gta tat ctt ggt ggc tat cct ggt cca ttg aag gaa gtt aca ggc att<br>Val Tyr Leu Gly Gly Tyr Pro Gly Pro Leu Lys Glu Val Thr Gly Ile<br>            500                 505                 510 | | 1536 |
| tgg gtt gaa gaa agt gat gca gta gtc cca gga caa aag att aag gtc<br>Trp Val Glu Glu Ser Asp Ala Val Val Pro Gly Gln Lys Ile Lys Val<br>        515                 520                 525 | | 1584 |
| tta atg aat ggt aag gat tat gat act ggt ctg atc tgt aac ttg att<br>Leu Met Asn Gly Lys Asp Tyr Asp Thr Gly Leu Ile Cys Asn Leu Ile<br>    530                 535                 540 | | 1632 |
| cat cca aat gac gct aag att ttg gca act tat gcg agt gaa ttt tat<br>His Pro Asn Asp Ala Lys Ile Leu Ala Thr Tyr Ala Ser Glu Phe Tyr<br>545                 550                 555                 560 | | 1680 |
| gca ggt acg cca gct gtt acc gaa aat caa tat ggc aaa ggt agg gct<br>Ala Gly Thr Pro Ala Val Thr Glu Asn Gln Tyr Gly Lys Gly Arg Ala<br>                565                 570                 575 | | 1728 |
| tgg tat att ggt aca agg ctt gaa cat caa ggg tta act caa tta ttc<br>Trp Tyr Ile Gly Thr Arg Leu Glu His Gln Gly Leu Thr Gln Leu Phe<br>            580                 585                 590 | | 1776 |
| aat cat att att ttt gaa acg ggt gtt gaa tca ctg gtt tgc gat agt<br>Asn His Ile Ile Phe Glu Thr Gly Val Glu Ser Leu Val Cys Asp Ser<br>        595                 600                 605 | | 1824 |
| cat aaa cta gaa ata act aag cgt gtt act gaa gat ggt aag gaa ctt<br>His Lys Leu Glu Ile Thr Lys Arg Val Thr Glu Asp Gly Lys Glu Leu<br>    610                 615                 620 | | 1872 |
| tac ttt gtg ctt aat atg agt aat gaa gaa aga acg tta cca agc aag<br>Tyr Phe Val Leu Asn Met Ser Asn Glu Glu Arg Thr Leu Pro Ser Lys<br>625                 630                 635                 640 | | 1920 |
| ttc aca ggt tat gaa gat att tta act ggt gaa aaa gct cat aaa gat<br>Phe Thr Gly Tyr Glu Asp Ile Leu Thr Gly Glu Lys Ala His Lys Asp<br>                645                 650                 655 | | 1968 |
| atg aaa ggt tgg gat gtt caa gta ttg aga aat<br>Met Lys Gly Trp Asp Val Gln Val Leu Arg Asn<br>            660                 665 | | 2001 |

<210> SEQ ID NO 22
<211> LENGTH: 667
<212> TYPE: PRT
<213> ORGANISM: Lactobacillus Acidophilus

<400> SEQUENCE: 22

Met Thr Gln Leu Ser Arg Phe Leu Tyr Gly Gly Asp Tyr Asn Pro Asp
 1               5                  10                  15

Gln Trp Pro Glu Glu Thr Trp Ser Lys Asp Ile His Val Phe Lys Lys
            20                  25                  30

Ala Asp Ile Asn Ser Ala Thr Ile Asn Ile Phe Ser Trp Ala Leu Leu
        35                  40                  45

```
Glu Pro Arg Glu Gly Lys Tyr Asn Phe Ser Lys Leu Asp Lys Val Val
 50                  55                  60

Gln Gln Leu Ser Asp Ala Asn Phe Asp Ile Val Met Gly Thr Ala Thr
 65                  70                  75                  80

Ala Ala Met Pro Ala Trp Met Phe Lys Lys Tyr Pro Asp Ile Ala Arg
                 85                  90                  95

Val Asp Tyr Gln Asp Arg Arg His Val Phe Gly Gln Arg His Asn Phe
                100                 105                 110

Cys Pro Asn Ser Ser Asn Tyr Gln Arg Leu Ala Gly Glu Leu Val Lys
                115                 120                 125

Gln Leu Val Glu Arg Tyr Lys Asp Asn Lys His Ile Val Val Trp His
        130                 135                 140

Ile Asn Asn Glu Tyr Gly Gly Asn Cys Tyr Cys Glu Asn Cys Gln Asn
145                 150                 155                 160

Ala Phe Arg Lys Trp Leu Lys Asn Lys Tyr Lys Thr Val Glu Gly Leu
                165                 170                 175

Asn Lys Ala Trp Asn Met Asn Val Trp Ser His Thr Ile Tyr Asp Trp
                180                 185                 190

Asp Glu Ile Val Val Pro Asn Glu Leu Gly Asp Val Trp Gly Ile Glu
        195                 200                 205

Gly Ser Glu Thr Ile Val Ala Gly Leu Ser Ile Asp Tyr Leu Arg Phe
210                 215                 220

Gln Ser Glu Ser Met Gln Asn Leu Phe Lys Met Glu Lys Lys Ile Ile
225                 230                 235                 240

Lys Lys Tyr Asp Pro Glu Thr Pro Val Thr Thr Asn Phe His Gly Leu
                245                 250                 255

Pro Asn Lys Met Val Asp Tyr Gln Lys Trp Ala Lys Gly Gln Asp Ile
                260                 265                 270

Ile Ser Tyr Asp Ser Tyr Pro Thr Tyr Asp Ala Pro Ala Tyr Lys Ala
                275                 280                 285

Ala Phe Leu Tyr Asp Leu Met Arg Ser Leu Lys His Gln Pro Phe Met
                290                 295                 300

Leu Met Glu Ser Ala Pro Ser Gln Val Asn Trp Gln Pro Tyr Ser Pro
305                 310                 315                 320

Leu Lys Arg Pro Gly Gln Met Glu Ala Thr Glu Phe Gln Ala Val Ala
                325                 330                 335

His Gly Ala Asp Thr Val Gln Phe Phe Gln Leu Lys Gln Ala Val Gly
                340                 345                 350

Gly Ser Glu Lys Phe His Ser Ala Val Ile Ala His Ser Gln Arg Thr
        355                 360                 365

Asp Thr Arg Val Phe Lys Glu Leu Ala Asp Leu Gly Lys Lys Leu Lys
        370                 375                 380

Asn Ala Gly Pro Thr Ile Leu Gly Ser Lys Thr Lys Ala Lys Val Ala
385                 390                 395                 400

Ile Val Phe Asp Trp Ser Asn Phe Trp Ser Tyr Glu Tyr Val Asp Gly
                405                 410                 415

Ile Thr Gln Asp Leu Asn Tyr Val Asp Ser Ile Leu Asp Tyr Tyr Arg
                420                 425                 430

Gln Phe Tyr Glu Arg Asn Ile Pro Thr Asp Ile Gly Val Asp Asp
                435                 440                 445

Asp Phe Ser Asn Tyr Asp Leu Val Val Ala Pro Val Leu Tyr Met Val
        450                 455                 460

Lys His Gly Leu Asp Lys Lys Ile Asn Asp Tyr Val Glu Asn Gly Gly
465                 470                 475                 480
```

```
Asn Phe Val Thr Thr Tyr Met Ser Gly Met Val Asn Ser Ser Asp Asn
            485                 490                 495

Val Tyr Leu Gly Gly Tyr Pro Gly Pro Leu Lys Glu Val Thr Gly Ile
        500                 505                 510

Trp Val Glu Glu Ser Asp Ala Val Pro Gly Gln Lys Ile Lys Val
            515                 520                 525

Leu Met Asn Gly Lys Asp Tyr Asp Thr Gly Leu Ile Cys Asn Leu Ile
    530                 535                 540

His Pro Asn Asp Ala Lys Ile Leu Ala Thr Tyr Ala Ser Glu Phe Tyr
545                 550                 555                 560

Ala Gly Thr Pro Ala Val Thr Glu Asn Gln Tyr Gly Lys Gly Arg Ala
                565                 570                 575

Trp Tyr Ile Gly Thr Arg Leu Glu His Gln Gly Leu Thr Gln Leu Phe
            580                 585                 590

Asn His Ile Ile Phe Glu Thr Gly Val Glu Ser Leu Val Cys Asp Ser
        595                 600                 605

His Lys Leu Glu Ile Thr Lys Arg Val Thr Glu Asp Gly Lys Glu Leu
    610                 615                 620

Tyr Phe Val Leu Asn Met Ser Asn Glu Glu Arg Thr Leu Pro Ser Lys
625                 630                 635                 640

Phe Thr Gly Tyr Glu Asp Ile Leu Thr Gly Glu Lys Ala His Lys Asp
                645                 650                 655

Met Lys Gly Trp Asp Val Gln Val Leu Arg Asn
            660                 665

<210> SEQ ID NO 23
<211> LENGTH: 840
<212> TYPE: DNA
<213> ORGANISM: Lactobacillus Acidophilus
<220> FEATURE:
<221> NAME/KEY: CDS
<222> LOCATION: (1)...(840)

<400> SEQUENCE: 23 atg aaa cgc aat ata aaa ctt tta tcg act att agt gtt gct gca gct    48
Met Lys Arg Asn Ile Lys Leu Leu Ser Thr Ile Ser Val Ala Ala Ala
1               5                   10                  15 tta gca ggt agt gct att ttt gtt atg aat aat aat caa gaa gac aat    96
Leu Ala Gly Ser Ala Ile Phe Val Met Asn Asn Asn Gln Glu Asp Asn
                20                  25                  30 tca aca gtt caa gct gca tca att aca ttg cct tct ggc tat act aaa   144
Ser Thr Val Gln Ala Ala Ser Ile Thr Leu Pro Ser Gly Tyr Thr Lys
            35                  40                  45 aat gct gtt att aaa tgg aat caa act ggt aaa gca agt aaa gcc tta   192
Asn Ala Val Ile Lys Trp Asn Gln Thr Gly Lys Ala Ser Lys Ala Leu
        50                  55                  60 att aat gcc tca aaa aag ggc atg atg gaa aac act aat agc gat gca   240
Ile Asn Ala Ser Lys Lys Gly Met Met Glu Asn Thr Asn Ser Asp Ala
65                  70                  75                  80 ggt tct gac aat act cta gtt aat gtt act aag ttg act aat agt caa   288
Gly Ser Asp Asn Thr Leu Val Asn Val Thr Lys Leu Thr Asn Ser Gln
                85                  90                  95 aaa gtt gag ttg agc aaa tat act tta agt tta atc aat tct gct cgt   336
Lys Val Glu Leu Ser Lys Tyr Thr Leu Ser Leu Ile Asn Ser Ala Arg
            100                 105                 110 agc caa ctt ggc aaa aaa cct tgg aca tat aga agt ggc gct tta cgt   384
Ser Gln Leu Gly Lys Lys Pro Trp Thr Tyr Arg Ser Gly Ala Leu Arg
        115                 120                 125
```

```
ttt gca gat cgt gtt gcc aat cag tac tat aca cat aac aag tca tgt        432
Phe Ala Asp Arg Val Ala Asn Gln Tyr Tyr Thr His Asn Lys Ser Cys
    130                 135                 140 tgg gat cct gat cat tat gta gct ggt att tta cgg gct gct aaa gct        480
Trp Asp Pro Asp His Tyr Val Ala Gly Ile Leu Arg Ala Ala Lys Ala
145                 150                 155                 160 tca ggt ctt aat tca aat gca ggt caa gta tat gaa gat gaa gca ggc        528
Ser Gly Leu Asn Ser Asn Ala Gly Gln Val Tyr Glu Asp Glu Ala Gly
                165                 170                 175 tta cct att tca tca caa tat ggc tca aat ctt cgt act atg tca gtt        576
Leu Pro Ile Ser Ser Gln Tyr Gly Ser Asn Leu Arg Thr Met Ser Val
            180                 185                 190 tta aag aat caa att tac ttt aat gta aaa caa atg ctt ttc ggt ggt        624
Leu Lys Asn Gln Ile Tyr Phe Asn Val Lys Gln Met Leu Phe Gly Gly
        195                 200                 205 ttt gcc ggt agc gat agt caa atg aat gat tct tca aga tat act gaa        672
Phe Ala Gly Ser Asp Ser Gln Met Asn Asp Ser Ser Arg Tyr Thr Glu
    210                 215                 220 tgg gaa cac gcc ggt gat tta ctt ggt tgt cgt aca aag aat tat gat        720
Trp Glu His Ala Gly Asp Leu Leu Gly Cys Arg Thr Lys Asn Tyr Asp
225                 230                 235                 240 gcc aag act aaa tac ttt ggt gta agt ttt agt gga tta aaa gat gat        768
Ala Lys Thr Lys Tyr Phe Gly Val Ser Phe Ser Gly Leu Lys Asp Asp
                245                 250                 255 caa agt aag att agt gtt cac atg att ggt gtt gca aaa cgt tat att        816
Gln Ser Lys Ile Ser Val His Met Ile Gly Val Ala Lys Arg Tyr Ile
            260                 265                 270 caa aac tac aaa aaa ttt aac cac                                        840
Gln Asn Tyr Lys Lys Phe Asn His
        275                 280

<210> SEQ ID NO 24
<211> LENGTH: 280
<212> TYPE: PRT
<213> ORGANISM: Lactobacillus Acidophilus

<400> SEQUENCE: 24

Met Lys Arg Asn Ile Lys Leu Leu Ser Thr Ile Ser Val Ala Ala Ala
1               5                   10                  15

Leu Ala Gly Ser Ala Ile Phe Val Met Asn Asn Asn Gln Glu Asp Asn
            20                  25                  30

Ser Thr Val Gln Ala Ala Ser Ile Thr Leu Pro Ser Gly Tyr Thr Lys
        35                  40                  45

Asn Ala Val Ile Lys Trp Asn Gln Thr Gly Lys Ala Ser Lys Ala Leu
    50                  55                  60

Ile Asn Ala Ser Lys Lys Gly Met Met Glu Asn Thr Asn Ser Asp Ala
65                  70                  75                  80

Gly Ser Asp Asn Thr Leu Val Asn Val Thr Lys Leu Thr Asn Ser Gln
                85                  90                  95

Lys Val Glu Leu Ser Lys Tyr Thr Leu Ser Leu Ile Asn Ser Ala Arg
            100                 105                 110

Ser Gln Leu Gly Lys Lys Pro Trp Thr Tyr Arg Ser Gly Ala Leu Arg
        115                 120                 125

Phe Ala Asp Arg Val Ala Asn Gln Tyr Tyr Thr His Asn Lys Ser Cys
    130                 135                 140

Trp Asp Pro Asp His Tyr Val Ala Gly Ile Leu Arg Ala Ala Lys Ala
145                 150                 155                 160

Ser Gly Leu Asn Ser Asn Ala Gly Gln Val Tyr Glu Asp Glu Ala Gly
                165                 170                 175
```

```
Leu Pro Ile Ser Ser Gln Tyr Gly Ser Asn Leu Arg Thr Met Ser Val
            180                 185                 190

Leu Lys Asn Gln Ile Tyr Phe Asn Val Lys Gln Met Leu Phe Gly Gly
        195                 200                 205

Phe Ala Gly Ser Asp Ser Gln Met Asn Asp Ser Ser Arg Tyr Thr Glu
210                 215                 220

Trp Glu His Ala Gly Asp Leu Leu Gly Cys Arg Thr Lys Asn Tyr Asp
225                 230                 235                 240

Ala Lys Thr Lys Tyr Phe Gly Val Ser Phe Gly Leu Lys Asp Asp
                245                 250                 255

Gln Ser Lys Ile Ser Val His Met Ile Gly Val Ala Lys Arg Tyr Ile
        260                 265                 270

Gln Asn Tyr Lys Lys Phe Asn His
        275                 280

<210> SEQ ID NO 25
<211> LENGTH: 663
<212> TYPE: DNA
<213> ORGANISM: Lactobacillus Acidophilus
<220> FEATURE:
<221> NAME/KEY: CDS
<222> LOCATION: (1)...(663)

<400> SEQUENCE: 25
```

| | | | | | | | | | | | | | | | | |
|---|---|---|---|---|---|---|---|---|---|---|---|---|---|---|---|---|
| atg | ctt | aaa | ggc | tta | att | ttt | gat | tta | gat | ggt | gtc | tta | acc | gac | tca | 48 |
| Met | Leu | Lys | Gly | Leu | Ile | Phe | Asp | Leu | Asp | Gly | Val | Leu | Thr | Asp | Ser | |
| 1 | | | | 5 | | | | | 10 | | | | | 15 | | |
| gca | cgt | ttc | cac | ctt | aca | gct | tgg | aat | aat | ttg | gct | aag | gaa | tta | ggc | 96 |
| Ala | Arg | Phe | His | Leu | Thr | Ala | Trp | Asn | Asn | Leu | Ala | Lys | Glu | Leu | Gly | |
| | | | 20 | | | | | 25 | | | | | 30 | | | |
| att | act | tta | aca | aac | gaa | caa | ctt | gat | agt | tta | cgt | ggt | att | tca | aga | 144 |
| Ile | Thr | Leu | Thr | Asn | Glu | Gln | Leu | Asp | Ser | Leu | Arg | Gly | Ile | Ser | Arg | |
| | | 35 | | | | | 40 | | | | | 45 | | | | |
| atg | gat | tcg | ctt | aat | ttg | atc | ttg | aag | tat | ggc | ggt | caa | gaa | gat | aag | 192 |
| Met | Asp | Ser | Leu | Asn | Leu | Ile | Leu | Lys | Tyr | Gly | Gly | Gln | Glu | Asp | Lys | |
| 50 | | | | | 55 | | | | | 60 | | | | | | |
| tat | act | gaa | gca | gaa | aaa | gaa | aaa | ttt | gct | gca | gaa | aag | aat | gct | aag | 240 |
| Tyr | Thr | Glu | Ala | Glu | Lys | Glu | Lys | Phe | Ala | Ala | Glu | Lys | Asn | Ala | Lys | |
| 65 | | | | | 70 | | | | | 75 | | | | | 80 | |
| ttt | gtt | gag | caa | gtt | gaa | aca | atg | aca | cca | aag | gat | atc | cta | cct | ggc | 288 |
| Phe | Val | Glu | Gln | Val | Glu | Thr | Met | Thr | Pro | Lys | Asp | Ile | Leu | Pro | Gly | |
| | | | | 85 | | | | | 90 | | | | | 95 | | |
| att | cca | gaa | tta | ctt | agt | gat | gct | aag | aag | caa | aac | tta | aag | atg | gta | 336 |
| Ile | Pro | Glu | Leu | Leu | Ser | Asp | Ala | Lys | Lys | Gln | Asn | Leu | Lys | Met | Val | |
| | | | 100 | | | | | 105 | | | | | 110 | | | |
| att | gct | tct | gct | tca | aag | aat | gca | cct | aag | att | tta | act | aga | cta | gga | 384 |
| Ile | Ala | Ser | Ala | Ser | Lys | Asn | Ala | Pro | Lys | Ile | Leu | Thr | Arg | Leu | Gly | |
| | | 115 | | | | | 120 | | | | | 125 | | | | |
| att | atg | gat | gaa | ttt | gat | ggg | att | gtt | gat | cct | gcc | act | ctt | cat | cat | 432 |
| Ile | Met | Asp | Glu | Phe | Asp | Gly | Ile | Val | Asp | Pro | Ala | Thr | Leu | His | His | |
| | 130 | | | | | 135 | | | | | 140 | | | | | |
| ggt | aag | cca | gat | cca | gaa | att | tat | atc | aaa | gcg | caa | gaa | ctt | gtt | gga | 480 |
| Gly | Lys | Pro | Asp | Pro | Glu | Ile | Tyr | Ile | Lys | Ala | Gln | Glu | Leu | Val | Gly | |
| 145 | | | | | 150 | | | | | 155 | | | | | 160 | |
| ttg | aag | gca | aat | gaa | gta | att | agc | ttt | gaa | gat | gcc | caa | gct | ggt | gtt | 528 |
| Leu | Lys | Ala | Asn | Glu | Val | Ile | Ser | Phe | Glu | Asp | Ala | Gln | Ala | Gly | Val | |
| | | | | 165 | | | | | 170 | | | | | 175 | | |
| gaa | gca | att | aag | gct | gct | cat | caa | ttt | gca | gtt | gga | ata | ggt | aat | aaa | 576 |
| Glu | Ala | Ile | Lys | Ala | Ala | His | Gln | Phe | Ala | Val | Gly | Ile | Gly | Asn | Lys | |
| | | | 180 | | | | | 185 | | | | | 190 | | | |

```
aag ctt ttg aaa gaa gct gat tac atc gtt cca acc act gct gat ctt      624
Lys Leu Leu Lys Glu Ala Asp Tyr Ile Val Pro Thr Thr Ala Asp Leu
        195                 200                 205 aag ctt agt gaa att gaa aaa gtt ttt gaa gag aaa gaa                  663
Lys Leu Ser Glu Ile Glu Lys Val Phe Glu Glu Lys Glu
    210                 215                 220

<210> SEQ ID NO 26
<211> LENGTH: 221
<212> TYPE: PRT
<213> ORGANISM: Lactobacillus Acidophilus

<400> SEQUENCE: 26

Met Leu Lys Gly Leu Ile Phe Asp Leu Asp Gly Val Leu Thr Asp Ser
1               5                   10                  15

Ala Arg Phe His Leu Thr Ala Trp Asn Asn Leu Ala Lys Glu Leu Gly
            20                  25                  30

Ile Thr Leu Thr Asn Glu Gln Leu Asp Ser Leu Arg Gly Ile Ser Arg
        35                  40                  45

Met Asp Ser Leu Asn Leu Ile Leu Lys Tyr Gly Gly Gln Glu Asp Lys
    50                  55                  60

Tyr Thr Glu Ala Glu Lys Glu Lys Phe Ala Ala Glu Lys Asn Ala Lys
65                  70                  75                  80

Phe Val Glu Gln Val Glu Thr Met Thr Pro Lys Asp Ile Leu Pro Gly
                85                  90                  95

Ile Pro Glu Leu Leu Ser Asp Ala Lys Lys Gln Asn Leu Lys Met Val
            100                 105                 110

Ile Ala Ser Ala Ser Lys Asn Ala Pro Lys Ile Leu Thr Arg Leu Gly
        115                 120                 125

Ile Met Asp Glu Phe Asp Gly Ile Val Asp Pro Ala Thr Leu His His
    130                 135                 140

Gly Lys Pro Asp Pro Glu Ile Tyr Ile Lys Ala Gln Glu Leu Val Gly
145                 150                 155                 160

Leu Lys Ala Asn Glu Val Ile Ser Phe Glu Asp Ala Gln Ala Gly Val
                165                 170                 175

Glu Ala Ile Lys Ala Ala His Gln Phe Ala Val Gly Ile Gly Asn Lys
            180                 185                 190

Lys Leu Leu Lys Glu Ala Asp Tyr Ile Val Pro Thr Thr Ala Asp Leu
        195                 200                 205

Lys Leu Ser Glu Ile Glu Lys Val Phe Glu Glu Lys Glu
    210                 215                 220

<210> SEQ ID NO 27
<211> LENGTH: 432
<212> TYPE: DNA
<213> ORGANISM: Lactobacillus Acidophilus
<220> FEATURE:
<221> NAME/KEY: CDS
<222> LOCATION: (1)...(432)

<400> SEQUENCE: 27 ttg aat gaa ctc tca gat aga gaa aaa gca gat ata aaa aag caa ata      48
Met Asn Glu Leu Ser Asp Arg Glu Lys Ala Asp Ile Lys Lys Gln Ile
1               5                   10                  15 ttt aaa aca aaa gac tgg aat gaa aac tcg tta cgg cta ttg gcg atg      96
Phe Lys Thr Lys Asp Trp Asn Glu Asn Ser Leu Arg Leu Leu Ala Met
            20                  25                  30 gct atg cca ttt ttt aat ata gag gac tta aaa ttt att att aat act     144
Ala Met Pro Phe Phe Asn Ile Glu Asp Leu Lys Phe Ile Ile Asn Thr
```

```
                   35                  40                  45
att ttt agt aaa tat tat tca atg aaa gat gtt ttg gat gtt cag caa        192
Ile Phe Ser Lys Tyr Tyr Ser Met Lys Asp Val Leu Asp Val Gln Gln
 50                  55                  60 gaa ttg gta tct gca att gct gta aac tat ttg gga tta gct tat cat        240
Glu Leu Val Ser Ala Ile Ala Val Asn Tyr Leu Gly Leu Ala Tyr His
 65                  70                  75                  80 gag cat gat aaa gat gaa aaa gaa ata aaa tta gct ctt tct tta ctt        288
Glu His Asp Lys Asp Glu Lys Glu Ile Lys Leu Ala Leu Ser Leu Leu
                 85                  90                  95 aga cag tta agt cac gaa cct aaa aat tgc ttt gct aaa att atg gaa        336
Arg Gln Leu Ser His Glu Pro Lys Asn Cys Phe Ala Lys Ile Met Glu
            100                 105                 110 caa tat tat acg gct caa ttt gat aat gat aaa aag aaa gcg gag agg        384
Gln Tyr Tyr Thr Ala Gln Phe Asp Asn Asp Lys Lys Lys Ala Glu Arg
        115                 120                 125 att aaa cag ttt ttt att gaa aat gat atg aac tat tat gta gga gaa        432
Ile Lys Gln Phe Phe Ile Glu Asn Asp Met Asn Tyr Tyr Val Gly Glu
    130                 135                 140
```

<210> SEQ ID NO 28
<211> LENGTH: 144
<212> TYPE: PRT
<213> ORGANISM: Lactobacillus Acidophilus

<400> SEQUENCE: 28

```
Met Asn Glu Leu Ser Asp Arg Glu Lys Ala Asp Ile Lys Lys Gln Ile
 1               5                  10                  15

Phe Lys Thr Lys Asp Trp Asn Glu Asn Ser Leu Arg Leu Leu Ala Met
             20                  25                  30

Ala Met Pro Phe Phe Asn Ile Glu Asp Leu Lys Phe Ile Ile Asn Thr
         35                  40                  45

Ile Phe Ser Lys Tyr Tyr Ser Met Lys Asp Val Leu Asp Val Gln Gln
 50                  55                  60

Glu Leu Val Ser Ala Ile Ala Val Asn Tyr Leu Gly Leu Ala Tyr His
 65                  70                  75                  80

Glu His Asp Lys Asp Glu Lys Glu Ile Lys Leu Ala Leu Ser Leu Leu
                 85                  90                  95

Arg Gln Leu Ser His Glu Pro Lys Asn Cys Phe Ala Lys Ile Met Glu
            100                 105                 110

Gln Tyr Tyr Thr Ala Gln Phe Asp Asn Asp Lys Lys Lys Ala Glu Arg
        115                 120                 125

Ile Lys Gln Phe Phe Ile Glu Asn Asp Met Asn Tyr Tyr Val Gly Glu
    130                 135                 140
```

<210> SEQ ID NO 29
<211> LENGTH: 717
<212> TYPE: DNA
<213> ORGANISM: Lactobacillus Acidophilus
<220> FEATURE:
<221> NAME/KEY: CDS
<222> LOCATION: (1)...(717)

<400> SEQUENCE: 29

```
atg aaa gtt att gtt act gaa aac aaa att caa ggc agc gct aaa gca         48
Met Lys Val Ile Val Thr Glu Asn Lys Ile Gln Gly Ser Ala Lys Ala
 1               5                  10                  15 ttt gaa att ttt gaa aaa gga atc aag aat gga gct aag gtc tta ggc         96
Phe Glu Ile Phe Glu Lys Gly Ile Lys Asn Gly Ala Lys Val Leu Gly
             20                  25                  30
```

```
cta gct act ggt tct act cca gaa att ctt tac cag aat tgg gta aaa       144
Leu Ala Thr Gly Ser Thr Pro Glu Ile Leu Tyr Gln Asn Trp Val Lys
            35                  40                  45 agt gat ctt aac tgc gat gac ctt acc agt atc aat ctt gat gaa tat       192
Ser Asp Leu Asn Cys Asp Asp Leu Thr Ser Ile Asn Leu Asp Glu Tyr
50                  55                  60 gtc ggc tta aca cct gat aat cct caa agt tac cat tac ttc atg caa       240
Val Gly Leu Thr Pro Asp Asn Pro Gln Ser Tyr His Tyr Phe Met Gln
65                  70                  75                  80 aaa cac tta ttt gat aaa aaa aca ttc aag aaa acc tat atc cct gac       288
Lys His Leu Phe Asp Lys Lys Thr Phe Lys Lys Thr Tyr Ile Pro Asp
                85                  90                  95 ggc atg act aag gat gtt cca gca tac tgc aag gaa tac gat caa ata       336
Gly Met Thr Lys Asp Val Pro Ala Tyr Cys Lys Glu Tyr Asp Gln Ile
            100                 105                 110 att aaa gac aat cct att gat att caa tta tta ggt atc ggc caa aac       384
Ile Lys Asp Asn Pro Ile Asp Ile Gln Leu Leu Gly Ile Gly Gln Asn
            115                 120                 125 ggt cat att gcc ttt aat gaa cct ggt act cca ttc gat att ggc act       432
Gly His Ile Ala Phe Asn Glu Pro Gly Thr Pro Phe Asp Ile Gly Thr
130                 135                 140 cac gaa gtt aaa tta act gaa aac act att aag gct aac gca cgc ttt       480
His Glu Val Lys Leu Thr Glu Asn Thr Ile Lys Ala Asn Ala Arg Phe
145                 150                 155                 160 ttc gat aat gaa gat gaa gtt cca aag agc gca att tgt atg ggt act       528
Phe Asp Asn Glu Asp Glu Val Pro Lys Ser Ala Ile Cys Met Gly Thr
                165                 170                 175 gct aat atc atg gat tca aag aaa att gtt tta atg gca ttc ggt gaa       576
Ala Asn Ile Met Asp Ser Lys Lys Ile Val Leu Met Ala Phe Gly Glu
            180                 185                 190 aag aaa gct aag gcc att aaa gaa atg atc gaa gga cct atc act gaa       624
Lys Lys Ala Lys Ala Ile Lys Glu Met Ile Glu Gly Pro Ile Thr Glu
            195                 200                 205 gaa gtt cct gca tcc atc tta caa aaa cac cca gac gta act gtc atc       672
Glu Val Pro Ala Ser Ile Leu Gln Lys His Pro Asp Val Thr Val Ile
210                 215                 220 gtt gat aca tat gca gct caa gag ctt gac gat aaa tat aag aac            717
Val Asp Thr Tyr Ala Ala Gln Glu Leu Asp Asp Lys Tyr Lys Asn
225                 230                 235
```

<210> SEQ ID NO 30
<211> LENGTH: 239
<212> TYPE: PRT
<213> ORGANISM: Lactobacillus Acidophilus

<400> SEQUENCE: 30

```
Met Lys Val Ile Val Thr Glu Asn Lys Ile Gln Gly Ser Ala Lys Ala
1               5                   10                  15

Phe Glu Ile Phe Glu Lys Gly Ile Lys Asn Gly Ala Lys Val Leu Gly
            20                  25                  30

Leu Ala Thr Gly Ser Thr Pro Glu Ile Leu Tyr Gln Asn Trp Val Lys
            35                  40                  45

Ser Asp Leu Asn Cys Asp Asp Leu Thr Ser Ile Asn Leu Asp Glu Tyr
50                  55                  60

Val Gly Leu Thr Pro Asp Asn Pro Gln Ser Tyr His Tyr Phe Met Gln
65                  70                  75                  80

Lys His Leu Phe Asp Lys Lys Thr Phe Lys Lys Thr Tyr Ile Pro Asp
                85                  90                  95

Gly Met Thr Lys Asp Val Pro Ala Tyr Cys Lys Glu Tyr Asp Gln Ile
            100                 105                 110
```

```
Ile Lys Asp Asn Pro Ile Asp Ile Gln Leu Leu Gly Ile Gly Gln Asn
        115                 120                 125

Gly His Ile Ala Phe Asn Glu Pro Gly Thr Pro Phe Asp Ile Gly Thr
130                 135                 140

His Glu Val Lys Leu Thr Glu Asn Thr Ile Lys Ala Asn Ala Arg Phe
145                 150                 155                 160

Phe Asp Asn Glu Asp Glu Val Pro Lys Ser Ala Ile Cys Met Gly Thr
                165                 170                 175

Ala Asn Ile Met Asp Ser Lys Lys Ile Val Leu Met Ala Phe Gly Glu
            180                 185                 190

Lys Lys Ala Lys Ala Ile Lys Glu Met Ile Glu Gly Pro Ile Thr Glu
        195                 200                 205

Glu Val Pro Ala Ser Ile Leu Gln Lys His Pro Asp Val Thr Val Ile
    210                 215                 220

Val Asp Thr Tyr Ala Ala Gln Glu Leu Asp Asp Lys Tyr Lys Asn
225                 230                 235
```

<210> SEQ ID NO 31
<211> LENGTH: 2415
<212> TYPE: DNA
<213> ORGANISM: Lactobacillus Acidophilus
<220> FEATURE:
<221> NAME/KEY: CDS
<222> LOCATION: (1)...(2415)

<400> SEQUENCE: 31

```
gtg ctc aaa gga gaa aaa atg aca gtt aat tac gat tcc aaa gat tac     48
Met Leu Lys Gly Glu Lys Met Thr Val Asn Tyr Asp Ser Lys Asp Tyr
 1               5                  10                  15 tta aag agc gtt gac gca tat tgg cgt gca gct aat tat ttg tca gtt     96
Leu Lys Ser Val Asp Ala Tyr Trp Arg Ala Ala Asn Tyr Leu Ser Val
                20                  25                  30 gga caa tta ttt tta atg aaa aat ccg ttg tta aag aaa cct tta aca    144
Gly Gln Leu Phe Leu Met Lys Asn Pro Leu Leu Lys Lys Pro Leu Thr
            35                  40                  45 gct gaa gat gta aaa cct aag cca atc ggt cac tgg ggt act att gct    192
Ala Glu Asp Val Lys Pro Lys Pro Ile Gly His Trp Gly Thr Ile Ala
        50                  55                  60 cca caa aac ttt att tat gct cac tta aat cgt gcg ctt aaa aaa tat    240
Pro Gln Asn Phe Ile Tyr Ala His Leu Asn Arg Ala Leu Lys Lys Tyr
 65                  70                  75                  80 gac ttg gat atg ttc tat att gaa ggt tca ggt cac ggt ggc caa gtg    288
Asp Leu Asp Met Phe Tyr Ile Glu Gly Ser Gly His Gly Gly Gln Val
                 85                  90                  95 atg gtt tca aat tca tat ctt gat ggt tca tat act gaa cgt tat cca    336
Met Val Ser Asn Ser Tyr Leu Asp Gly Ser Tyr Thr Glu Arg Tyr Pro
            100                 105                 110 gaa att acc caa gat gaa aag ggt atg gct aaa ttg ttt aag cgc ttt    384
Glu Ile Thr Gln Asp Glu Lys Gly Met Ala Lys Leu Phe Lys Arg Phe
        115                 120                 125 agt ttc cca ggt ggt gta gct tct cac gct gct cct gaa act cca ggt    432
Ser Phe Pro Gly Gly Val Ala Ser His Ala Ala Pro Glu Thr Pro Gly
    130                 135                 140 tct att cat gaa ggt ggg gaa tta gga tac gca ctt tca cat ggg gta    480
Ser Ile His Glu Gly Gly Glu Leu Gly Tyr Ala Leu Ser His Gly Val
145                 150                 155                 160 ggt gct att tta gac aat cca gat gta att gct gcc gtt gaa att ggt    528
Gly Ala Ile Leu Asp Asn Pro Asp Val Ile Ala Ala Val Glu Ile Gly
                165                 170                 175
```

-continued

| | | |
|---|---|---|
| gat ggt gaa gca gaa act ggt cca ctt gca gct agc tgg ttc agt gac<br>Asp Gly Glu Ala Glu Thr Gly Pro Leu Ala Ala Ser Trp Phe Ser Asp<br>180                      185                     190 | | 576 |
| aag ttt att aat cca att aag gat ggt gca gtt tta cca att ctt caa<br>Lys Phe Ile Asn Pro Ile Lys Asp Gly Ala Val Leu Pro Ile Leu Gln<br>     195                    200                   205 | | 624 |
| att aat ggt ttc aag att tct aac cca act atc gtt tca aga atg agc<br>Ile Asn Gly Phe Lys Ile Ser Asn Pro Thr Ile Val Ser Arg Met Ser<br>210                      215                     220 | | 672 |
| gat gaa gaa tta act gaa tac ttc cgt ggc atg ggt tgg gat ccg cac<br>Asp Glu Glu Leu Thr Glu Tyr Phe Arg Gly Met Gly Trp Asp Pro His<br>225                    230                   235                  240 | | 720 |
| ttt gtt tca gta ttt aag ggt ggc cgc ttt gac ggt gaa aag gat cca<br>Phe Val Ser Val Phe Lys Gly Gly Arg Phe Asp Gly Glu Lys Asp Pro<br>                      245                   250                   255 | | 768 |
| atg caa gtc cac gaa gaa atg gct aaa acc atg gac gaa gta att gaa<br>Met Gln Val His Glu Glu Met Ala Lys Thr Met Asp Glu Val Ile Glu<br>                260                   265                   270 | | 816 |
| gaa att aag gct att caa aag cat gct cgt gaa aat aat gat gct act<br>Glu Ile Lys Ala Ile Gln Lys His Ala Arg Glu Asn Asn Asp Ala Thr<br>275                    280                   285 | | 864 |
| ttg cca cat tgg cca ttg att atc ttc caa tgt cca aag ggc tgg acc<br>Leu Pro His Trp Pro Leu Ile Ile Phe Gln Cys Pro Lys Gly Trp Thr<br>290                    295                 300 | | 912 |
| ggt cca aag aag gat ctt gac ggc aat cca att gaa aac tca ttt aga<br>Gly Pro Lys Lys Asp Leu Asp Gly Asn Pro Ile Glu Asn Ser Phe Arg<br>305                    310                   315                  320 | | 960 |
| gca cac caa att cca att cct gtc tca caa tac gat atg aaa cat gtt<br>Ala His Gln Ile Pro Ile Pro Val Ser Gln Tyr Asp Met Lys His Val<br>                      325                   330                   335 | | 1008 |
| gat atg ttg act gat tgg ctt gaa agt tat aag cca aac gaa tta ttc<br>Asp Met Leu Thr Asp Trp Leu Glu Ser Tyr Lys Pro Asn Glu Leu Phe<br>340                    345                   350 | | 1056 |
| aac gaa gat ggt tca cca aag gaa att gtt act gaa aac act gct aag<br>Asn Glu Asp Gly Ser Pro Lys Glu Ile Val Thr Glu Asn Thr Ala Lys<br>     355                    360                   365 | | 1104 |
| ggt gat caa cgt atg gca atg aat ccg atc act aat ggt ggt aag gat<br>Gly Asp Gln Arg Met Ala Met Asn Pro Ile Thr Asn Gly Gly Lys Asp<br>370                      375                     380 | | 1152 |
| cct aaa cga ttg aac cta cca gat tat cgc aac ttt gca ctt aag ttt<br>Pro Lys Arg Leu Asn Leu Pro Asp Tyr Arg Asn Phe Ala Leu Lys Phe<br>385                      390                   395                  400 | | 1200 |
| gac aag cca ggt tca gtt gaa gca caa gac atg gtt gaa tgg gct aaa<br>Asp Lys Pro Gly Ser Val Glu Ala Gln Asp Met Val Glu Trp Ala Lys<br>                      405                   410                   415 | | 1248 |
| tat tta aac gaa gtt gct aaa ctt aac cca act act ttc cgt ggc ttt<br>Tyr Leu Asn Glu Val Ala Lys Leu Asn Pro Thr Thr Phe Arg Gly Phe<br>420                      425                   430 | | 1296 |
| ggt cct gat gaa tct aaa tca aac cgt tta ttt aaa ctt tta gat gat<br>Gly Pro Asp Glu Ser Lys Ser Asn Arg Leu Phe Lys Leu Leu Asp Asp<br>                 435                   440                   445 | | 1344 |
| caa aag cgt caa tgg gaa cct gaa gtt cat gaa cca aat gat gaa aac<br>Gln Lys Arg Gln Trp Glu Pro Glu Val His Glu Pro Asn Asp Glu Asn<br>450                    455                   460 | | 1392 |
| ttg gca cca agt ggc cgc gtt atc gat tca caa tta tca gaa cac caa<br>Leu Ala Pro Ser Gly Arg Val Ile Asp Ser Gln Leu Ser Glu His Gln<br>465                    470                   475                  480 | | 1440 |
| gac gaa ggc ttc ctt gaa ggc tac gtt tta act ggt cgt cac ggc ttc<br>Asp Glu Gly Phe Leu Glu Gly Tyr Val Leu Thr Gly Arg His Gly Phe<br>                      485                   490                   495 | | 1488 |

-continued

| | | |
|---|---|---|
| ttt gca acc tac gaa gca ttt ggt cgt gta gta gat tcg atg ctt act<br>Phe Ala Thr Tyr Glu Ala Phe Gly Arg Val Val Asp Ser Met Leu Thr<br>500 505 510 | | 1536 |
| caa cat atg aag tgg ctt aga aaa gct aaa gaa caa tat tgg cgt cat<br>Gln His Met Lys Trp Leu Arg Lys Ala Lys Glu Gln Tyr Trp Arg His<br>515 520 525 | | 1584 |
| gat tat cca tca ctt aac ttt gtt gct act tca aca gta ttc caa caa<br>Asp Tyr Pro Ser Leu Asn Phe Val Ala Thr Ser Thr Val Phe Gln Gln<br>530 535 540 | | 1632 |
| gat cac aat ggt tac act cac caa gat cca ggc att tta act cac tta<br>Asp His Asn Gly Tyr Thr His Gln Asp Pro Gly Ile Leu Thr His Leu<br>545 550 555 560 | | 1680 |
| tat gaa aag aat cgt cca gat tta gtt cat gaa tac ttg cca tca gat<br>Tyr Glu Lys Asn Arg Pro Asp Leu Val His Glu Tyr Leu Pro Ser Asp<br>565 570 575 | | 1728 |
| act aat act tta ctt gct gta ggt aac aag gca ttt act gat cgt gaa<br>Thr Asn Thr Leu Leu Ala Val Gly Asn Lys Ala Phe Thr Asp Arg Glu<br>580 585 590 | | 1776 |
| tgt att aat gtt tta gta act tca aag caa cct cgt cca caa tgg ttc<br>Cys Ile Asn Val Leu Val Thr Ser Lys Gln Pro Arg Pro Gln Trp Phe<br>595 600 605 | | 1824 |
| tca att gag gaa gca caa aag tta gtt gat aaa ggt tta agt tac att<br>Ser Ile Glu Glu Ala Gln Lys Leu Val Asp Lys Gly Leu Ser Tyr Ile<br>610 615 620 | | 1872 |
| gat tgg gct tca act gat aaa ggt gta aaa cca gat att gtc ttt gct<br>Asp Trp Ala Ser Thr Asp Lys Gly Val Lys Pro Asp Ile Val Phe Ala<br>625 630 635 640 | | 1920 |
| tca aca gaa act gaa cca aca att gaa act ttg gca gca att gat att<br>Ser Thr Glu Thr Glu Pro Thr Ile Glu Thr Leu Ala Ala Ile Asp Ile<br>645 650 655 | | 1968 |
| ttg cat gac aag ttc cca gat ctt aag att cgc tac att aac gta att<br>Leu His Asp Lys Phe Pro Asp Leu Lys Ile Arg Tyr Ile Asn Val Ile<br>660 665 670 | | 2016 |
| gat gtg atg aaa tta atg tca cca aag gac aat aag aat ggt att tct<br>Asp Val Met Lys Leu Met Ser Pro Lys Asp Asn Lys Asn Gly Ile Ser<br>675 680 685 | | 2064 |
| gat gaa gaa ttt gat cgc tta ttc cca aag gac gtt cct gta atc ttt<br>Asp Glu Glu Phe Asp Arg Leu Phe Pro Lys Asp Val Pro Val Ile Phe<br>690 695 700 | | 2112 |
| gca tgg cac ggc tac aag agt atg atg gaa tca att tgg ttt gca cgt<br>Ala Trp His Gly Tyr Lys Ser Met Met Glu Ser Ile Trp Phe Ala Arg<br>705 710 715 720 | | 2160 |
| aac cgt cat aat gta cat att cac tgc tac gaa gaa aac ggt gat att<br>Asn Arg His Asn Val His Ile His Cys Tyr Glu Glu Asn Gly Asp Ile<br>725 730 735 | | 2208 |
| act acc cca ttt gat atg cgt gtt ttg aac cac ctt gac aga ttt gat<br>Thr Thr Pro Phe Asp Met Arg Val Leu Asn His Leu Asp Arg Phe Asp<br>740 745 750 | | 2256 |
| ctt gcc aaa gat gct gtt gaa agt gtt gat aaa ttg aag ggc aag aac<br>Leu Ala Lys Asp Ala Val Glu Ser Val Asp Lys Leu Lys Gly Lys Asn<br>755 760 765 | | 2304 |
| gct gac ttt atc agt cat atg gat gac ttg ctt gaa aag cac cac caa<br>Ala Asp Phe Ile Ser His Met Asp Asp Leu Leu Glu Lys His His Gln<br>770 775 780 | | 2352 |
| tac att cgt gat aat ggt aaa gat atg cca gaa gtt act gaa tgg aag<br>Tyr Ile Arg Asp Asn Gly Lys Asp Met Pro Glu Val Thr Glu Trp Lys<br>785 790 795 800 | | 2400 |
| tgg aag ggc ttg aag<br>Trp Lys Gly Leu Lys<br>805 | | 2415 |

<210> SEQ ID NO 32
<211> LENGTH: 805
<212> TYPE: PRT
<213> ORGANISM: Lactobacillus Acidophilus

<400> SEQUENCE: 32

```
Met Leu Lys Gly Glu Lys Met Thr Val Asn Tyr Asp Ser Lys Asp Tyr
 1               5                  10                  15
Leu Lys Ser Val Asp Ala Tyr Trp Arg Ala Ala Asn Tyr Leu Ser Val
                20                  25                  30
Gly Gln Leu Phe Leu Met Lys Asn Pro Leu Leu Lys Lys Pro Leu Thr
            35                  40                  45
Ala Glu Asp Val Lys Pro Lys Pro Ile Gly His Trp Gly Thr Ile Ala
        50                  55                  60
Pro Gln Asn Phe Ile Tyr Ala His Leu Asn Arg Ala Leu Lys Lys Tyr
65                  70                  75                  80
Asp Leu Asp Met Phe Tyr Ile Glu Gly Ser Gly His Gly Gly Gln Val
                85                  90                  95
Met Val Ser Asn Ser Tyr Leu Asp Gly Ser Tyr Thr Glu Arg Tyr Pro
            100                 105                 110
Glu Ile Thr Gln Asp Glu Lys Gly Met Ala Lys Leu Phe Lys Arg Phe
        115                 120                 125
Ser Phe Pro Gly Gly Val Ala Ser His Ala Ala Pro Glu Thr Pro Gly
    130                 135                 140
Ser Ile His Glu Gly Gly Glu Leu Gly Tyr Ala Leu Ser His Gly Val
145                 150                 155                 160
Gly Ala Ile Leu Asp Asn Pro Asp Val Ile Ala Ala Val Glu Ile Gly
                165                 170                 175
Asp Gly Glu Ala Glu Thr Gly Pro Leu Ala Ala Ser Trp Phe Ser Asp
            180                 185                 190
Lys Phe Ile Asn Pro Ile Lys Asp Gly Ala Val Leu Pro Ile Leu Gln
        195                 200                 205
Ile Asn Gly Phe Lys Ile Ser Asn Pro Thr Ile Val Ser Arg Met Ser
    210                 215                 220
Asp Glu Glu Leu Thr Glu Tyr Phe Arg Gly Met Gly Trp Asp Pro His
225                 230                 235                 240
Phe Val Ser Val Phe Lys Gly Gly Arg Phe Asp Gly Glu Lys Asp Pro
                245                 250                 255
Met Gln Val His Glu Glu Met Ala Lys Thr Met Asp Gly Val Ile Glu
            260                 265                 270
Glu Ile Lys Ala Ile Gln Lys His Ala Arg Glu Asn Asn Asp Ala Thr
        275                 280                 285
Leu Pro His Trp Pro Leu Ile Ile Phe Gln Cys Pro Lys Gly Trp Thr
    290                 295                 300
Gly Pro Lys Lys Asp Leu Asp Gly Asn Pro Ile Glu Asn Ser Phe Arg
305                 310                 315                 320
Ala His Gln Ile Pro Ile Pro Val Ser Gln Tyr Asp Met Lys His Val
                325                 330                 335
Asp Met Leu Thr Asp Trp Leu Glu Ser Tyr Lys Pro Asn Glu Leu Phe
            340                 345                 350
Asn Glu Asp Gly Ser Pro Lys Glu Ile Val Thr Glu Asn Thr Ala Lys
        355                 360                 365
Gly Asp Gln Arg Met Ala Met Asn Pro Ile Thr Asn Gly Gly Lys Asp
    370                 375                 380
```

-continued

Pro Lys Arg Leu Asn Leu Pro Asp Tyr Arg Asn Phe Ala Leu Lys Phe
385                 390                 395                 400

Asp Lys Pro Gly Ser Val Glu Ala Gln Asp Met Val Glu Trp Ala Lys
            405                 410                 415

Tyr Leu Asn Glu Val Ala Lys Leu Asn Pro Thr Thr Phe Arg Gly Phe
        420                 425                 430

Gly Pro Asp Glu Ser Lys Ser Asn Arg Leu Phe Lys Leu Leu Asp Asp
    435                 440                 445

Gln Lys Arg Gln Trp Glu Pro Glu Val His Glu Pro Asn Asp Glu Asn
450                 455                 460

Leu Ala Pro Ser Gly Arg Val Ile Asp Ser Gln Leu Ser Glu His Gln
465                 470                 475                 480

Asp Glu Gly Phe Leu Glu Gly Tyr Val Leu Thr Gly Arg His Gly Phe
                485                 490                 495

Phe Ala Thr Tyr Glu Ala Phe Gly Arg Val Val Asp Ser Met Leu Thr
            500                 505                 510

Gln His Met Lys Trp Leu Arg Lys Ala Lys Glu Gln Tyr Trp Arg His
        515                 520                 525

Asp Tyr Pro Ser Leu Asn Phe Val Ala Thr Ser Thr Val Phe Gln Gln
    530                 535                 540

Asp His Asn Gly Tyr Thr His Gln Asp Pro Gly Ile Leu Thr His Leu
545                 550                 555                 560

Tyr Glu Lys Asn Arg Pro Asp Leu Val His Glu Tyr Leu Pro Ser Asp
                565                 570                 575

Thr Asn Thr Leu Leu Ala Val Gly Asn Lys Ala Phe Thr Asp Arg Glu
            580                 585                 590

Cys Ile Asn Val Leu Val Thr Ser Lys Gln Pro Arg Pro Gln Trp Phe
        595                 600                 605

Ser Ile Glu Glu Ala Gln Lys Leu Val Asp Lys Gly Leu Ser Tyr Ile
    610                 615                 620

Asp Trp Ala Ser Thr Asp Lys Gly Val Lys Pro Asp Ile Val Phe Ala
625                 630                 635                 640

Ser Thr Glu Thr Glu Pro Thr Ile Glu Thr Leu Ala Ala Ile Asp Ile
                645                 650                 655

Leu His Asp Lys Phe Pro Asp Leu Lys Ile Arg Tyr Ile Asn Val Ile
            660                 665                 670

Asp Val Met Lys Leu Met Ser Pro Lys Asp Asn Lys Asn Gly Ile Ser
        675                 680                 685

Asp Glu Glu Phe Asp Arg Leu Phe Pro Lys Asp Pro Val Ile Phe
    690                 695                 700

Ala Trp His Gly Tyr Lys Ser Met Met Glu Ser Ile Trp Phe Ala Arg
705                 710                 715                 720

Asn Arg His Asn Val His Ile His Cys Tyr Glu Glu Asn Gly Asp Ile
                725                 730                 735

Thr Thr Pro Phe Asp Met Arg Val Leu Asn His Leu Asp Arg Phe Asp
            740                 745                 750

Leu Ala Lys Asp Ala Val Glu Ser Val Asp Lys Leu Lys Gly Lys Asn
        755                 760                 765

Ala Asp Phe Ile Ser His Met Asp Asp Leu Leu Glu Lys His His Gln
    770                 775                 780

Tyr Ile Arg Asp Asn Gly Lys Asp Met Pro Glu Val Thr Glu Trp Lys
785                 790                 795                 800

Trp Lys Gly Leu Lys
                805

<210> SEQ ID NO 33
<211> LENGTH: 369
<212> TYPE: DNA
<213> ORGANISM: Lactobacillus Acidophilus
<220> FEATURE:
<221> NAME/KEY: CDS
<222> LOCATION: (1)...(369)

<400> SEQUENCE: 33

```
atg gca gaa gaa aaa caa act cca gaa caa aag gac caa gaa acc ttg      48
Met Ala Glu Glu Lys Gln Thr Pro Glu Gln Lys Asp Gln Glu Thr Leu
 1               5                  10                  15 atg gct gct atg ggc tta att gca aat ggt gga aat gca aaa agt tta      96
Met Ala Ala Met Gly Leu Ile Ala Asn Gly Gly Asn Ala Lys Ser Leu
             20                  25                  30 gct ttt gaa gca att cgt ctt gca aag act ggt gat atc gaa ggc gca     144
Ala Phe Glu Ala Ile Arg Leu Ala Lys Thr Gly Asp Ile Glu Gly Ala
         35                  40                  45 cgt gaa aag tta aag gaa agt gat aag tca ctt ctt gag gca cac aat     192
Arg Glu Lys Leu Lys Glu Ser Asp Lys Ser Leu Leu Glu Ala His Asn
     50                  55                  60 tca cag aca agt atg ctt act caa gaa gca caa ggt gat cat atg cac     240
Ser Gln Thr Ser Met Leu Thr Gln Glu Ala Gln Gly Asp His Met His
 65                  70                  75                  80 gtg acc tta ttg gta gta cac tca caa gat cac ttg atg aat gct att     288
Val Thr Leu Leu Val Val His Ser Gln Asp His Leu Met Asn Ala Ile
                 85                  90                  95 acc ttt aga gat ttg gct gga gaa atg gtg gat ctt tac gaa aag cta     336
Thr Phe Arg Asp Leu Ala Gly Glu Met Val Asp Leu Tyr Glu Lys Leu
            100                 105                 110 tat aat tct ggc gct ctt aaa aaa gaa gat aag                         369
Tyr Asn Ser Gly Ala Leu Lys Lys Glu Asp Lys
        115                 120
```

<210> SEQ ID NO 34
<211> LENGTH: 123
<212> TYPE: PRT
<213> ORGANISM: Lactobacillus Acidophilus

<400> SEQUENCE: 34

```
Met Ala Glu Glu Lys Gln Thr Pro Glu Gln Lys Asp Gln Glu Thr Leu
 1               5                  10                  15

Met Ala Ala Met Gly Leu Ile Ala Asn Gly Gly Asn Ala Lys Ser Leu
             20                  25                  30

Ala Phe Glu Ala Ile Arg Leu Ala Lys Thr Gly Asp Ile Glu Gly Ala
         35                  40                  45

Arg Glu Lys Leu Lys Glu Ser Asp Lys Ser Leu Leu Glu Ala His Asn
     50                  55                  60

Ser Gln Thr Ser Met Leu Thr Gln Glu Ala Gln Gly Asp His Met His
 65                  70                  75                  80

Val Thr Leu Leu Val Val His Ser Gln Asp His Leu Met Asn Ala Ile
                 85                  90                  95

Thr Phe Arg Asp Leu Ala Gly Glu Met Val Asp Leu Tyr Glu Lys Leu
            100                 105                 110

Tyr Asn Ser Gly Ala Leu Lys Lys Glu Asp Lys
        115                 120
```

<210> SEQ ID NO 35
<211> LENGTH: 2268
<212> TYPE: DNA

<213> ORGANISM: Lactobacillus Acidophilus
<220> FEATURE:
<221> NAME/KEY: CDS
<222> LOCATION: (1)...(2268)

<400> SEQUENCE: 35

| | | | | | | | | | | | | | | | | |
|---|---|---|---|---|---|---|---|---|---|---|---|---|---|---|---|---|
| atg | aaa | cga | att | ttt | gaa | att | gat | cct | tgg | aaa | gtc | att | act | cat | aaa | 48 |
| Met | Lys | Arg | Ile | Phe | Glu | Ile | Asp | Pro | Trp | Lys | Val | Ile | Thr | His | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | gat | cca | aaa | gat | aag | aga | ttg | cag | gaa | agt | atg | act | gca | atc | ggt | 96 |
| Phe | Asp | Pro | Lys | Asp | Lys | Arg | Leu | Gln | Glu | Ser | Met | Thr | Ala | Ile | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | gat | tac | atg | gga | atg | aga | gga | aac | ttt | gaa | gaa | ggt | tat | tca | ggt | 144 |
| Asn | Asp | Tyr | Met | Gly | Met | Arg | Gly | Asn | Phe | Glu | Glu | Gly | Tyr | Ser | Gly | |
| | | | 35 | | | | | 40 | | | | | 45 | | | |

| | | | | | | | | | | | | | | | | |
|---|---|---|---|---|---|---|---|---|---|---|---|---|---|---|---|---|
| gat | agc | ctc | caa | ggt | aca | tac | tta | gca | gga | gtt | tgg | ttc | cca | gat | aaa | 192 |
| Asp | Ser | Leu | Gln | Gly | Thr | Tyr | Leu | Ala | Gly | Val | Trp | Phe | Pro | Asp | Lys | |
| 50 | | | | | 55 | | | | | 60 | | | | | | |

| | | | | | | | | | | | | | | | | |
|---|---|---|---|---|---|---|---|---|---|---|---|---|---|---|---|---|
| acg | gtt | gtt | ggt | tgg | tgg | aag | aat | gga | tat | cca | aaa | tat | ttt | ggt | aaa | 240 |
| Thr | Val | Val | Gly | Trp | Trp | Lys | Asn | Gly | Tyr | Pro | Lys | Tyr | Phe | Gly | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | cca | aat | gct | cca | agt | ttt | att | gga | att | gga | atc | aat | gta | aat | ggt | 288 |
| Thr | Pro | Asn | Ala | Pro | Ser | Phe | Ile | Gly | Ile | Gly | Ile | Asn | Val | Asn | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | aag | gtc | gat | tta | gct | aaa | gtt | aaa | ttt | agc | gac | ttt | gaa | tta | tca | 336 |
| Glu | Lys | Val | Asp | Leu | Ala | Lys | Val | Lys | Phe | Ser | Asp | Phe | Glu | Leu | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| cta | gac | atg | cat | caa | ggt | ctt | ctt | tcg | aga | agt | ttt | atc | tat | gaa | ggt | 384 |
| Leu | Asp | Met | His | Gln | Gly | Leu | Leu | Ser | Arg | Ser | Phe | Ile | Tyr | Glu | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| aaa | gat | gtc | aaa | gtt | aag | ctt | gaa | ttt | gaa | cgc | ttt | ctt | cac | att | gtt | 432 |
| Lys | Asp | Val | Lys | Val | Lys | Leu | Glu | Phe | Glu | Arg | Phe | Leu | His | Ile | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| caa | aaa | gaa | gct | gct | cta | att | aaa | gtt | aaa | gca | act | gta | ctt | gaa | ggc | 480 |
| Gln | Lys | Glu | Ala | Ala | Leu | Ile | Lys | Val | Lys | Ala | Thr | Val | Leu | Glu | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cat | gca | aag | att | gat | ttt | gac | tca | act | tta | gac | ggc | act | gtt | gtt | aat | 528 |
| His | Ala | Lys | Ile | Asp | Phe | Asp | Ser | Thr | Leu | Asp | Gly | Thr | Val | Val | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | gac | agt | aat | tat | ggc | gat | cgc | ttc | tgg | att | cca | ctt | ggt | gaa | gat | 576 |
| Glu | Asp | Ser | Asn | Tyr | Gly | Asp | Arg | Phe | Trp | Ile | Pro | Leu | Gly | Glu | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | gat | gaa | aaa | act | att | caa | gta | aag | act | aag | aaa | aat | cca | tat | gac | 624 |
| Lys | Asp | Glu | Lys | Thr | Ile | Gln | Val | Lys | Thr | Lys | Lys | Asn | Pro | Tyr | Asp | |
| | | | 195 | | | | | 200 | | | | | 205 | | | |

| | | | | | | | | | | | | | | | | |
|---|---|---|---|---|---|---|---|---|---|---|---|---|---|---|---|---|
| gta | cca | caa | ttt | aca | gta | ttg | ttg | aaa | gaa | gca | tta | cgt | aat | aat | ggc | 672 |
| Val | Pro | Gln | Phe | Thr | Val | Leu | Leu | Lys | Glu | Ala | Leu | Arg | Asn | Asn | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| gta | gca | gta | aat | gga | gaa | gtt | act | act | gaa | gat | gca | aaa | ttg | agt | gaa | 720 |
| Val | Ala | Val | Asn | Gly | Glu | Val | Thr | Thr | Glu | Asp | Ala | Lys | Leu | Ser | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aga | ttc | tca | gta | gaa | tta | gac | gaa | ggt | caa | agc | tat | gaa | ctt | gaa | aaa | 768 |
| Arg | Phe | Ser | Val | Glu | Leu | Asp | Glu | Gly | Gln | Ser | Tyr | Glu | Leu | Glu | Lys | |
| | | | | 245 | | | | | 250 | | | | | 255 | | |

| | | | | | | | | | | | | | | | | |
|---|---|---|---|---|---|---|---|---|---|---|---|---|---|---|---|---|
| gat | gtc | att | gtt | gta | act | agt | cgt | gat | gtt | gaa | gaa | aaa | gat | caa | gca | 816 |
| Asp | Val | Ile | Val | Val | Thr | Ser | Arg | Asp | Val | Glu | Glu | Lys | Asp | Gln | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| gcc | gtt | gct | aac | aac | ttg | atg | agt | aaa | ctt | caa | acc | aag | agt | ttt | gaa | 864 |
| Ala | Val | Ala | Asn | Asn | Leu | Met | Ser | Lys | Leu | Gln | Thr | Lys | Ser | Phe | Glu | |
| | | | 275 | | | | | 280 | | | | | 285 | | | |

| | | | | | | | | | | | | | | | | |
|---|---|---|---|---|---|---|---|---|---|---|---|---|---|---|---|---|
| gat | aac | tta | gca | gat | cat | aca | gaa | gct | tgg | aag | aag | cgt | tgg | gaa | aca | 912 |

```
                Asp Asn Leu Ala Asp His Thr Glu Ala Trp Lys Lys Arg Trp Glu Thr
                    290                 295                 300 agt gat gta gaa atc agc ggc gac gat gca gct caa caa ggt att cgc        960
Ser Asp Val Glu Ile Ser Gly Asp Asp Ala Ala Gln Gln Gly Ile Arg
305                 310                 315                 320 ttc aat att tgt caa tta ttt atg aca tat tac ggt gaa gac aag cgc       1008
Phe Asn Ile Cys Gln Leu Phe Met Thr Tyr Tyr Gly Glu Asp Lys Arg
                325                 330                 335 ttg aat gta ggt cct aaa ggc ttt act ggt gaa aaa tac ggt ggt gcc       1056
Leu Asn Val Gly Pro Lys Gly Phe Thr Gly Glu Lys Tyr Gly Gly Ala
        340                 345                 350 act tat tgg gat acc gaa gcc ttt atc gtt cca atg tat tta gca gta       1104
Thr Tyr Trp Asp Thr Glu Ala Phe Ile Val Pro Met Tyr Leu Ala Val
            355                 360                 365 act aaa cca agt gtt aca aga gca ctt ctt caa tat cgt cac gat caa       1152
Thr Lys Pro Ser Val Thr Arg Ala Leu Leu Gln Tyr Arg His Asp Gln
370                 375                 380 ttg cca ggt gct tac cat aat gct aaa gaa caa ggc ctt cca ggt gca       1200
Leu Pro Gly Ala Tyr His Asn Ala Lys Glu Gln Gly Leu Pro Gly Ala
385                 390                 395                 400 tta ttc cca atg gtt acc ttc aat ggt att gaa tgt cac aac gaa tgg       1248
Leu Phe Pro Met Val Thr Phe Asn Gly Ile Glu Cys His Asn Glu Trp
                405                 410                 415 gaa atc aca ttt gaa gaa att cac aga aat gca gat att ccc cac gca       1296
Glu Ile Thr Phe Glu Glu Ile His Arg Asn Ala Asp Ile Pro His Ala
                420                 425                 430 ata gcc atg tac act gat tac act ggc gat gac agt tac gtt aag aat       1344
Ile Ala Met Tyr Thr Asp Tyr Thr Gly Asp Asp Ser Tyr Val Lys Asn
        435                 440                 445 gaa ggt atg gac gtt tta gtc ggt aca gca aga ttc tgg gca gct aga       1392
Glu Gly Met Asp Val Leu Val Gly Thr Ala Arg Phe Trp Ala Ala Arg
    450                 455                 460 gtt cac tgg tca aag atg cgt aac aaa tac gta atg cac ggt gta aca       1440
Val His Trp Ser Lys Met Arg Asn Lys Tyr Val Met His Gly Val Thr
465                 470                 475                 480 ggt cct aat gaa tat gaa aat aac gta aac aac aac tgg ttt act aac       1488
Gly Pro Asn Glu Tyr Glu Asn Asn Val Asn Asn Asn Trp Phe Thr Asn
                485                 490                 495 aca atg gct aga tgg ctt ctc aaa tat act ttg gaa cgt ttg cca ctt       1536
Thr Met Ala Arg Trp Leu Leu Lys Tyr Thr Leu Glu Arg Leu Pro Leu
                500                 505                 510 gct act aag gaa gct caa gaa aga gtt cgt gtt act gac gaa gaa aaa       1584
Ala Thr Lys Glu Ala Gln Glu Arg Val Arg Val Thr Asp Glu Glu Lys
        515                 520                 525 gct aaa tgg caa gat att gtg gat aac atg tac tta cca gaa gat gaa       1632
Ala Lys Trp Gln Asp Ile Val Asp Asn Met Tyr Leu Pro Glu Asp Glu
530                 535                 540 gat ctt ggc att ttc ttg caa caa gat gat ttc tta gat aaa gat att       1680
Asp Leu Gly Ile Phe Leu Gln Gln Asp Asp Phe Leu Asp Lys Asp Ile
545                 550                 555                 560 cgt cct gtt act gag att gaa gat caa cgt cca att aat caa cac tgg       1728
Arg Pro Val Thr Glu Ile Glu Asp Gln Arg Pro Ile Asn Gln His Trp
                565                 570                 575 tca tgg gac aag att tta cgt tca cca ttt att aag caa gcc gat gtt       1776
Ser Trp Asp Lys Ile Leu Arg Ser Pro Phe Ile Lys Gln Ala Asp Val
                580                 585                 590 tta caa ggt att tac ttc ttt gat gat caa tac act atg gat caa aag       1824
Leu Gln Gly Ile Tyr Phe Phe Asp Asp Gln Tyr Thr Met Asp Gln Lys
        595                 600                 605 gaa aag aac ttc gat ttc tat gaa cca tta aca gtt cac gaa agt tca       1872
```

```
Glu Lys Asn Phe Asp Phe Tyr Glu Pro Leu Thr Val His Glu Ser Ser
        610             615                 620 ctt tca cca tgt att tac tca att atg gct gca gaa ctt ggc aag aaa    1920
Leu Ser Pro Cys Ile Tyr Ser Ile Met Ala Ala Glu Leu Gly Lys Lys
625                 630                 635                 640 gaa aag gca gtt gaa ctt tac caa aga act gca cgt ctt gac ctt gat    1968
Glu Lys Ala Val Glu Leu Tyr Gln Arg Thr Ala Arg Leu Asp Leu Asp
            645                 650                 655 aac tat aat aac gac aca gta gat ggt tta cac att act tca atg agt    2016
Asn Tyr Asn Asn Asp Thr Val Asp Gly Leu His Ile Thr Ser Met Ser
        660                 665                 670 ggt tca tgg ctt gcg att gtt caa ggt ttc gca ggg atg cgt tac gat    2064
Gly Ser Trp Leu Ala Ile Val Gln Gly Phe Ala Gly Met Arg Tyr Asp
675                 680                 685 cat gat caa ttg aag ttc aac cca ttt gtt cct gat ggt tgg gat cac    2112
His Asp Gln Leu Lys Phe Asn Pro Phe Val Pro Asp Gly Trp Asp His
        690                 695                 700 tac agc ttt aag att aat tat cgt ggt cgt ttg att gaa gtt tat gta    2160
Tyr Ser Phe Lys Ile Asn Tyr Arg Gly Arg Leu Ile Glu Val Tyr Val
705                 710                 715                 720 gat cat gat gaa tgc aag att act tta ctt tct ggt gat gat ctt gaa    2208
Asp His Asp Glu Cys Lys Ile Thr Leu Leu Ser Gly Asp Asp Leu Glu
                725                 730                 735 gtc atg gta cat gac aat aaa ttg gat ttg aag gaa ggt aaa act aaa    2256
Val Met Val His Asp Asn Lys Leu Asp Leu Lys Glu Gly Lys Thr Lys
            740                 745                 750 tgc tta aag gct                                                    2268
Cys Leu Lys Ala
        755

<210> SEQ ID NO 36
<211> LENGTH: 756
<212> TYPE: PRT
<213> ORGANISM: Lactobacillus Acidophilus

<400> SEQUENCE: 36

Met Lys Arg Ile Phe Glu Ile Asp Pro Trp Lys Val Ile Thr His Lys
1               5                   10                  15

Phe Asp Pro Lys Asp Lys Arg Leu Gln Glu Ser Met Thr Ala Ile Gly
            20                  25                  30

Asn Asp Tyr Met Gly Met Arg Gly Asn Phe Glu Glu Gly Tyr Ser Gly
        35                  40                  45

Asp Ser Leu Gln Gly Thr Tyr Leu Ala Gly Val Trp Phe Pro Asp Lys
    50                  55                  60

Thr Val Val Gly Trp Trp Lys Asn Gly Tyr Pro Lys Tyr Phe Gly Lys
65                  70                  75                  80

Thr Pro Asn Ala Pro Ser Phe Ile Gly Ile Gly Ile Asn Val Asn Gly
                85                  90                  95

Glu Lys Val Asp Leu Ala Lys Val Lys Phe Ser Asp Phe Glu Leu Ser
            100                 105                 110

Leu Asp Met His Gln Gly Leu Leu Ser Arg Ser Phe Ile Tyr Glu Gly
        115                 120                 125

Lys Asp Val Lys Val Leu Glu Phe Glu Arg Phe Leu His Ile Val
    130                 135                 140

Gln Lys Glu Ala Ala Leu Ile Lys Val Lys Ala Thr Val Leu Glu Gly
145                 150                 155                 160

His Ala Lys Ile Asp Phe Asp Ser Thr Leu Asp Gly Thr Val Val Asn
                165                 170                 175
```

```
Glu Asp Ser Asn Tyr Gly Asp Arg Phe Trp Ile Pro Leu Gly Asp
            180                 185                 190
Lys Asp Glu Lys Thr Ile Gln Val Lys Thr Lys Asn Pro Tyr Asp
        195                 200                 205
Val Pro Gln Phe Thr Val Leu Leu Lys Glu Ala Leu Arg Asn Asn Gly
    210                 215                 220
Val Ala Val Asn Gly Glu Val Thr Thr Glu Asp Ala Lys Leu Ser Glu
225                 230                 235                 240
Arg Phe Ser Val Glu Leu Asp Glu Gly Gln Ser Tyr Glu Leu Glu Lys
                245                 250                 255
Asp Val Ile Val Thr Ser Arg Asp Val Glu Glu Lys Asp Gln Ala
            260                 265                 270
Ala Val Ala Asn Asn Leu Met Ser Lys Leu Gln Thr Lys Ser Phe Glu
    275                 280                 285
Asp Asn Leu Ala Asp His Thr Glu Ala Trp Lys Lys Arg Trp Glu Thr
        290                 295                 300
Ser Asp Val Glu Ile Ser Gly Asp Asp Ala Ala Gln Gln Gly Ile Arg
305                 310                 315                 320
Phe Asn Ile Cys Gln Leu Phe Met Thr Tyr Tyr Gly Glu Asp Lys Arg
                325                 330                 335
Leu Asn Val Gly Pro Lys Gly Phe Thr Gly Glu Lys Tyr Gly Gly Ala
            340                 345                 350
Thr Tyr Trp Asp Thr Glu Ala Phe Ile Val Pro Met Tyr Leu Ala Val
        355                 360                 365
Thr Lys Pro Ser Val Thr Arg Ala Leu Leu Gln Tyr Arg His Asp Gln
    370                 375                 380
Leu Pro Gly Ala Tyr His Asn Ala Lys Glu Gln Gly Leu Pro Gly Ala
385                 390                 395                 400
Leu Phe Pro Met Val Thr Phe Asn Gly Ile Glu Cys His Asn Glu Trp
                405                 410                 415
Glu Ile Thr Phe Glu Glu Ile His Arg Asn Ala Asp Ile Pro His Ala
            420                 425                 430
Ile Ala Met Tyr Thr Asp Tyr Thr Gly Asp Asp Ser Tyr Val Lys Asn
        435                 440                 445
Glu Gly Met Asp Val Leu Val Gly Thr Ala Arg Phe Trp Ala Ala Arg
    450                 455                 460
Val His Trp Ser Lys Met Arg Asn Lys Tyr Val Met His Gly Val Thr
465                 470                 475                 480
Gly Pro Asn Glu Tyr Glu Asn Asn Val Asn Asn Trp Phe Thr Asn
                485                 490                 495
Thr Met Ala Arg Trp Leu Leu Lys Tyr Thr Leu Glu Arg Leu Pro Leu
            500                 505                 510
Ala Thr Lys Glu Ala Gln Glu Arg Val Arg Val Thr Asp Glu Glu Lys
        515                 520                 525
Ala Lys Trp Gln Asp Ile Val Asp Asn Met Tyr Leu Pro Glu Asp Glu
    530                 535                 540
Asp Leu Gly Ile Phe Leu Gln Gln Asp Phe Leu Asp Lys Asp Ile
545                 550                 555                 560
Arg Pro Val Thr Glu Ile Glu Asp Gln Arg Pro Ile Asn Gln His Trp
                565                 570                 575
Ser Trp Asp Lys Ile Leu Arg Ser Pro Phe Ile Lys Gln Ala Asp Val
            580                 585                 590
Leu Gln Gly Ile Tyr Phe Phe Asp Asp Gln Tyr Thr Met Asp Gln Lys
        595                 600                 605
```

-continued

```
Glu Lys Asn Phe Asp Phe Tyr Glu Pro Leu Thr Val His Glu Ser Ser
    610                 615             620

Leu Ser Pro Cys Ile Tyr Ser Ile Met Ala Ala Glu Leu Gly Lys Lys
625                 630             635                     640

Glu Lys Ala Val Glu Leu Tyr Gln Arg Thr Ala Arg Leu Asp Leu Asp
                645             650                 655

Asn Tyr Asn Asn Asp Thr Val Asp Gly Leu His Ile Thr Ser Met Ser
            660             665                 670

Gly Ser Trp Leu Ala Ile Val Gln Gly Phe Ala Gly Met Arg Tyr Asp
            675             680             685

His Asp Gln Leu Lys Phe Asn Pro Phe Val Pro Asp Gly Trp Asp His
    690             695             700

Tyr Ser Phe Lys Ile Asn Tyr Arg Gly Arg Leu Ile Glu Val Tyr Val
705                 710             715                 720

Asp His Asp Glu Cys Lys Ile Thr Leu Leu Ser Gly Asp Asp Leu Glu
                725             730             735

Val Met Val His Asp Asn Lys Leu Asp Leu Lys Glu Gly Lys Thr Lys
            740             745             750

Cys Leu Lys Ala
            755
```

LACTOBACILLUS ACIDOPHILUS NUCLEIC ACIDS AND USES THEREOF

CROSS-REFERENCE TO RELATED APPLICATIONS

This application is a divisional of U.S. application Ser. No. 11/260,843, filed Oct. 27, 2005, now U.S. Pat. No. 7,468,182 which claims the benefit of U.S. Provisional Application No. 60/711,491, filed Aug. 26, 2005 and U.S. Provisional Application No. 60/622,712, filed Oct. 27, 2004, the contents of both applications are hereby incorporated by reference in their entirety.

FIELD OF THE INVENTION

This invention relates to polynucleotides and polypeptides encoded by them, as well as methods for using the polypeptides and microorganisms expressing them.

BACKGROUND OF THE INVENTION

*Lactobacillus acidophilus* is a Gram-positive, rod-shaped, non-spore forming, homofermentative bacterium that is a normal inhabitant of the gastrointestinal and genitourinary tracts. Since its original isolation by Moro (1900) from infant feces, the "acid loving" organism has been found in the intestinal tract of humans, breast fed infants, and persons consuming high milk-, lactose-, or dextrin diets. Historically, *Lactobacillus Acidophilus* is the *Lactobacillus* species most often implicated as an intestinal probiotic capable of eliciting beneficial effects on the microflora of the gastrointestinal tract (Klaenhammer and Russell (2000) "Species of the *Lactobacillus acidophilus* Complex," in *Encyclopedia of Food Microbiology*, Volume 2, ed. Robinson et al., (Academic Press, San Diego, Calif.), pp. 1151-1157). *Lactobacillus Acidophilus* can ferment hexoses, including lactose and more complex oligosaccharides (Kaplan and Hutkins (2000) *Appl. Environ. Microbiol.* 66:2682-2684) to produce lactic acid and lower the pH of the environment where the organism is cultured. Acidified environments (e.g. food, vagina, and regions within the gastrointestinal tract) can interfere with the growth of undesirable bacteria, pathogens, and yeasts. The organism is well known for its acid tolerance, survival in cultured dairy products, and viability during passage through the stomach and gastrointestinal tract. Lactobacilli and other commensal bacteria, some of which are considered as probiotic bacteria that "favor life," have been studied extensively for their effects on human health, particularly in the prevention or treatment of enteric infections, diarrheal disease, prevention of cancer, and stimulation of the immune system.

Microbial esterases and lipases are presently of interest because of their potential applications in biotechnology for food processing, surfactant composition, detergents, paper, oil manufacture, diagnostics, and optically active drugs (Jaeger et al. (1999) *Annu. Rev. Microbiol.* 53:315-351, Jaeger and Reetz (1998) *Trends Biotech.* 16:396-403). The enzymes that modify milk fat are lipases (triacylglycerol lipases; EC 3.1.1.3) and esterases (EC 3.1.1.1). Esterases are, by definition, enzymes that have the ability to hydrolyze ester substrates with short-chain fatty esters ($\leq C_{10}$), whereas lipases hydrolyze long-chain acylglycerols ($\geq C_{10}$) (Verger (1997) *Trends Biotech.* 15:32-38). The substrates and products of these enzymes may be involved in the formation of various flavor components of maturing cheeses, fermented dairy products, cured bacon and fermented sausages. It has been an interest in the dairy field to reduce the inherent cost and to enhance flavor intensity of various cheeses by shortening the maturation period in their preparation and processing. The free fatty acids, which are liberated by the action of lipases or esterases on milk fat, give dairy products their typical flavor characteristics. Upon further breakdown of fatty acids, reactions with other components of maturing cheeses and fermented dairy products, which may contribute to the formation of various flavor components, are likely to occur (Stead (1986) *J. Dairy Sci.* 53:481-505).

Oxalic acid is a strong dicarboxylic acid ($pK_a^1=1.23$; $pK_a^2=3.83$) and a toxic compound that irritates tissues. This effect was recognized in the eighteenth century, when used for cleaning and bleaching. Oxalate in extremely high concentrations can cause death in humans and animals, and pathological disorders, including hyperoxaluria (an oxalate level exceeding the normal range), pyridoxine deficiency, urolithiasis (formation of calculi or uroliths), renal failure, and others (Hatch et al. (1995) *Scanning Microsc* 9:1121-1126). The toxicity of oxalate has been related to its capability to generate reactive oxygen species (through the Fenton reaction) as hydroxyl or carbonate radicals during its interaction with hydrogen peroxide (Park et al. (1997) *Free Rad Res* 27:447-458 and Urzua et al. (1998) *Appl. Envirn. Microbiol.* 64:68-73). Oxalate occurs widely in nature and many foods such as boiled carrots (1.88 mg/g), tomatoes (0.04 mg/g), celery (0.17 mg/g), potato (0.02 mg/g) and corn (0.03 mg/g), and other dietary sources such as tea (0.11 mg/ml), coffee (0.05 mg/ml) and chocolate (1.17 mg/g). Oxalic acid can also be produced by non enzymatic degradation or from some metabolic precursors (like ascorbic acid) by the intestinal microflora (Ogawa et al. (2000) *World J. Surg.* 24:1154-1159). In the intestine, oxalate may combine with calcium, sodium, magnesium, or potassium forming less soluble salts, but also with iron generating high soluble salts. The presence of bacteria that specifically degrade oxalate has been proposed to regulate the oxalate homeostasis of the host by preventing absorption, catabolizing free oxalate and enhancing oxalate secretion from the circulation. A recent clinical study has demonstrated a correlation between low rates of intestine colonization with oxalate-degrading bacteria, specifically *Oxalobacter formigenes*, with an increased risk of hyperoxaluria due to an increase in urinary oxalate concentration (Troxel et al. (2003) *J. Endourol.* 17:173-176). Accordingly, compositions and methods are needed in the art that can modulate oxalate degradation.

SUMMARY OF THE INVENTION

Figure 1:
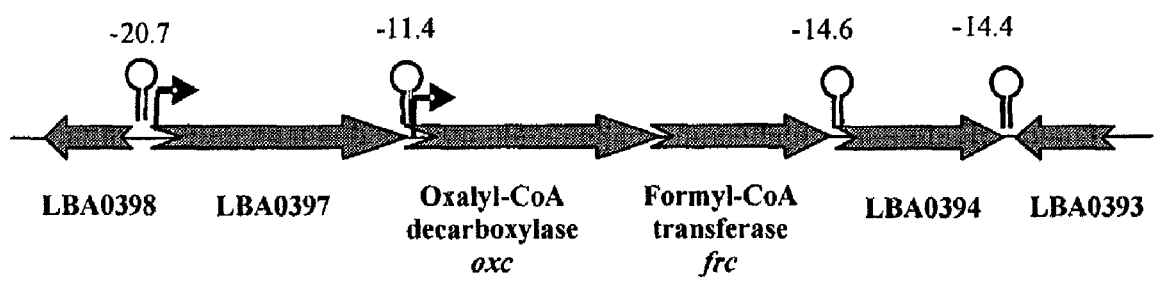
FIG. 1 shows the formyl-CoA transferase and oxalyl-CoA decarboxylase genes in *L. acidophilus* NCFM. Putative rho-dependent terminators and their correspondent free energy are indicated.

Specifically, the present invention provides isolated nucleic acid molecules comprising, consisting essentially of and/or consisting of the nucleotide sequences as set forth in odd numbered sequences as set forth in SEQ ID NOS:1-36, and isolated nucleic acid molecules encoding the amino acid sequences comprising the even numbered sequences as set forth in SEQ ID NOS:1-36. Also provided are isolated or recombinant polypeptides encoded by a nucleic acid molecule described herein, as well as. polypeptides comprising, consisting essentially of and/or consisting of the amino acid sequences as set forth in even numbered SEQ ID NOS:1-36. Variant nucleic acid molecules and polypeptides sufficiently identical to the nucleotide and amino acid sequences set forth in the sequence listings are encompassed by the present invention. Additionally, fragments and sufficiently identical fragments of the nucleotide and amino acid sequences are encompassed. Nucleotide sequences that are complementary to a nucleotide sequence of the invention, or that hybridize to a sequence of the invention are also encompassed.

Compositions further include vectors and cells for recombinant expression of the nucleic acid molecules described herein, as well as transgenic microbial and/or cell populations comprising the vectors. Also included in the invention are methods for the recombinant production of the polypeptides of the invention, and methods for their use. Further are included methods and kits for detecting the presence of a nucleic acid or polypeptide sequence of the invention in a sample, and antibodies that bind to a polypeptide of the invention.

Vectors, cells, and microbes having at least one of these sequences are further provided. These sequences can find use in modulating the oxalate degrading activity of a cell or an organism. Further provided are methods for modulating oxalate degradation in a subject. In one embodiment, oxalate degradation in a subject is increased by administering to the subject and effective concentration of at least one oxalate degrading sequence of the invention. In another embodiment, oxalate degradation in a subject is increased by administering to the subject an effective concentration of a microbe having at least one of the oxalate degrading sequences of the invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. As used herein, "a" or "an" can mean one or more than one. For example, "a cell" can mean a single cell or a plurality of cells.

As used herein, the terms "gene" and "recombinant gene" refer to nucleic acid molecules comprising an open reading frame (ORF) encoding a protein. Isolated nucleic acid molecules of the present invention comprise nucleotide sequences encoding the amino acid sequences set forth in even numbered SEQ ID NOS:1-36, the nucleic acid sequences set forth in odd numbered SEQ ID NOS:1-36 (it being appreciated that nucleic acids are given in the odd-number sequences only, while amino acid sequences are set forth in even numbers), and variants and fragments thereof. The present invention also encompasses antisense nucleic acid molecules, as described below. In another embodiment, promoter and/or regulatory nucleic acid sequences are provided to facilitate expression of nucleic acids.

In addition, isolated polypeptides and proteins encoded by the ORFs set forth, and variants and fragments thereof, are encompassed, as well as methods for producing those polypeptides. For purposes of the present invention, the terms "protein" and "polypeptide" are used interchangeably.

The nucleic acid and protein compositions encompassed by the present invention are isolated or substantially purified. By "isolated" or "substantially purified" is meant that the nucleic acid or protein molecules, or biologically active fragments or variants, are substantially or essentially free from components normally found in association with the nucleic acid or protein in its natural state. Such components include other cellular material, culture media from recombinant production, and various chemicals used in chemically synthesizing the proteins or nucleic acids. Preferably, an "isolated" nucleic acid of the present invention is free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition. For example, in various embodiments, the isolated nucleic acid contains less than 5 kb, 4 kb, 3 kb, 2 kb, 1 kb, 0.5 kb, or 0.1 kb of nucleic acid sequence normally associated with the genomic DNA in the cells from which it was derived. Similarly, a substantially purified protein has less than about 30%, 20%, 10%, 5%, or 1% (by dry weight) of contaminating protein. When the protein is recombinantly produced, preferably culture medium represents less than 30%, 20%, 10%, or 5% of the volume of the protein preparation, and when the protein is produced chemically, preferably the preparations have less than about 30%, 20%, 10%, or 5% (by dry weight) of chemical precursors.

The compositions and methods of the present invention can be used to modulate the function of molecules. By "modulate," "alter," or "modify" is meant the up- or down-regulation of a target activity. In accordance with the present invention, the level or activity of a sequence of the invention is modulated (i.e., overexpressed or underexpressed) if the level and/or activity of the sequence is statistically lower or higher than the level and/or activity of the same sequence in an appropriate control. Concentration and/or activity can be increased or decreased by at least 0.5%, 1%, 5%, 10%, 20%, 30%, 40%, 50%, 60%, 70%, 80%, or 90% relative to an appropriate control. Proteins of the invention are useful in modifying the abilities of various bacteria including probiotics and lactic acid bacteria, and also in modifying the nutritional or health-promoting characteristics of foods fermented by such bacteria. Nucleotide molecules of the invention are useful in modulating protein expression. Up- or down-regulation of expression from a polynucleotide of the present invention is encompassed. Up-regulation may be accomplished by providing multiple gene copies, modulating expression by modifying regulatory elements, promoting transcriptional or translational mechanisms, or other means. Down-regulation may be accomplished by using known antisense and gene silencing techniques.

By "lactic acid bacteria" is meant bacteria from a genus selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella* (Holzapfel et al. (2001) *Am. J. Clin. Nutr.* 73:365 S-373S; Bergey's Manual of Systematic Bacteriology, Vol. 2. 1986. Williams and Wilkins, Baltimore. pp 1075-1079).

By "*Lactobacillus*" is meant any bacteria from the genus *Lactobacillus*, including but not limited to *L. casei, L. rhamnosus, L. johnsonni, L. gasserei, L. acidophilus, L. plantarum, L. fermentum, L. salivarius, L. bulgaricus*, and numerous other species outlined by Wood et al. (Holzapfel, W. H. N. *The Genera of Lactic Acid Bacteria*, Vol. 2. 1995. Brian J. B. Wood, Ed. Aspen Publishers, Inc.)

The polypeptides of the present invention or microbes producing them are useful as nutritional additives or supplements, and as additives in dairy and fermentation processing. The polynucleotide sequences, encoded polypeptides and microorganisms expressing them are useful in the manufacture of milk-derived products, such as cheeses, yogurt, fermented milk products, sour milks and buttermilk. Microorganisms that produce polypeptides of the invention may be probiotic organisms. By "probiotic" is meant a live microorganism that survives passage through the gastrointestinal tract and has a beneficial effect on the subject. By "subject" is meant a living organism, including a plant, a microbe, a human, an animal (domestic, agricultural, or exotic), etc.

The polynucleotides and polypeptides of the present invention are useful in modifying milk-derived products. These uses include, but are not limited to, modulating the growth rate of a bacterium, modifying the flavor of a fermented dairy product, modulating the acidification rate of a milk product fermented by lactic acid bacteria, and altering the products produced during fermentation.

In another embodiment, the compositions of the invention comprise oxalate degrading polypeptides and polynucleotides. Such sequences include those set forth in SEQ ID NOS:1, 2, 3, and 4. Additional sequences include those set forth in SEQ ID NOS:5-36 which can be used to modulate oxalate degradation. As discussed in further detail below, such sequences can be used to modulate the oxalate degradation capability of a variety of cell types, microbes, and subjects. Specific proteins included in the present invention can be found in Table 1.

In various embodiments, the nucleic acid molecules of the invention encode proteins. They can also encode mRNA transcripts having the cDNA sequences comprising nucleotide sequences as set forth in SEQ ID NO:1 or 3 or odd numbered SEQ ID NOS:5-36.

In addition to the nucleotide sequences disclosed herein, and fragments and variants thereof, the isolated nucleic acid molecules of the current invention also encompass homologous DNA sequences identified and isolated from other organisms or cells by hybridization with entire or partial sequences obtained from the nucleotide sequences disclosed herein, or variants and fragments thereof.

Fragments and Variants

The invention includes isolated nucleic acid molecules comprising nucleotide sequences regulating and encoding proteins or variants and fragments thereof, as well as the proteins encoded thereby. By "protein" is meant proteins having the amino acid sequences as set forth in SEQ ID NOS:2 and 4 and even numbered SEQ ID NOS:5-36. Fragments, biologically active portions, and/or variants of these nucleotide sequences and encoded proteins are also provided. By "fragment" of a nucleotide sequence or protein is meant a portion of the nucleotide sequence or amino acid sequence that is less than the entire nucleotide sequence or protein.

Fragments of the nucleic acid molecules disclosed herein can be used as hybridization probes to identify other sequences in a sample having varying degrees of homology to the nucleic acid molecules of this invention, or can be used as primers in PCR amplification protocols or mutation of sequences. Fragments of nucleic acid molecules of this invention can also be bound to a physical substrate to comprise what can be considered a macro- or microarray (see, for example, U.S. Pat. Nos. 5,837,832; 5,861,242; 6,309,823, and International Publication Nos. WO 89/10977, WO 89/11548, and WO 93/17126). Such arrays of nucleic acids can be used to study gene expression or to identify nucleic acid molecules with sufficient identity to the target sequences.

By "nucleic acid molecule" is meant DNA molecules (e.g., cDNA or genomic DNA) and RNA molecules (e.g., mRNA) and analogs of DNA or RNA generated using nucleotide analogs. The nucleic acid molecule can be single-stranded or double-stranded, but preferably is double-stranded DNA. A nucleotide fragment of a protein can encode a protein fragment that is biologically active, or it can be used as a hybridization probe or PCR primer as described herein. A biologically active nucleotide fragment can be prepared by isolating a portion of one of the nucleotide sequences of the invention, expressing the nucleotide sequence to produce the encoded portion of the protein (e.g., by recombinant expression in vitro), and assessing the activity of the encoded portion of the protein. Fragments of nucleic acid molecules can comprise at least about 5, 10, 15, 20, 25, 30, 35, 40, 45, 50, 75, 100, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2200, 2500, 2700, 3000, 3200, 3500, 3700, 4000, 4200, or 4500 contiguous nucleotides, including any number between 5 and 4500 not specifically recited herein, or up to the total number of nucleotides present in a full-length nucleotide sequence as disclosed herein.

Fragments of amino acid sequences include polypeptide fragments suitable for use as immunogens to raise antibodies. Fragments include peptides comprising amino acid sequences sufficiently identical to or derived from the amino acid sequence of a protein, or partial-length protein, of the invention and exhibiting at least one activity of a protein, but which include fewer amino acids than the full-length proteins disclosed herein. Typically, biologically active fragments comprise a domain or motif with at least one activity of the protein. A biologically active fragment of a protein can be a polypeptide which is, for example, 5, 10, 15, 20, 25, 30, 40, 50, 75, 100, 150, 200, 300, 400, or 500 contiguous amino acids in length, including any number between 5 and 500 not specifically recited herein, or up to the total number of amino acids present in a full-length protein of the current invention. Such biologically active fragments can be prepared, for example, by recombinant techniques and evaluated for one or more of the immunogenic and/or functional activities of a native protein. As used here, a fragment comprises at least 5 contiguous amino acids of even numbered SEQ ID NOS:1-36. The invention encompasses other fragments, however, such as any fragment in the protein greater than 6, 7, 8, or 9 amino acids.

In one embodiment of the invention, fragments of the polynucleotides or polypeptides of SEQ ID NOS:5-36 are provided. A biologically active fragment of a polypeptide or polynucleotide of SEQ ID NO:5-36 can comprise, for example, 5, 10, 15, 20, 25, 30, 40, 50, 75, 100, 150, 200, 300, 400, or 500 contiguous amino acids or nucleotides in length, including any number between 5 and 500 not specifically recited herein, or up to the total number of amino acids or nucleotides present in a full-length protein or polynucleotide of the invention. Such biologically active fragments can continue to be biologically active (i.e., modulate oxalate degrading activity or any other activity disclosed herein).

In another embodiment of the invention, fragments of the polynucleotides or polypeptides of SEQ ID NOS:1, 2, 3, or 4 are provided. A biologically active fragment of a polypeptide or polynucleotide of SEQ ID NO:1, 2, 3, or 4 can comprise, for example, 5, 10, 15, 20, 25, 30, 40, 50, 75, 100, 150, 200, 300, 400, or 500 contiguous amino acids or nucleotides in length, including any number between 5 and 500 not specifically recited herein, or up to the total number of amino acids or nucleotides present in a full-length protein or polynucleotide of the invention. Such biologically active fragments can continue to be biologically active (i.e., have oxalate degrading activity or any other method disclosed herein).

Variants of the nucleotide and amino acid sequences are encompassed in the present invention. By "variant" is meant a sufficiently identical sequence. Accordingly, the invention encompasses isolated nucleic acid molecules that are sufficiently identical to the nucleotide sequences encoding polypeptides comprising amino acid sequences as set forth in even numbered SEQ ID NOS:1-36, or nucleic acid molecules that hybridize to a nucleic acid molecule comprising a nucleotide sequence as set forth in odd numbered SEQ ID NOS:1-36, or a complement thereof, under stringent conditions. Variants also include polypeptides encoded by the nucleotide sequences of the present invention. In addition, polypeptides of the current invention have an amino acid sequence that is sufficiently identical to an amino acid sequence as set forth in even numbered SEQ. ID NOS:1-36. By "sufficiently identical" is meant that one amino acid sequence or nucleotide sequence contains a sufficient or minimal number of equivalent or identical amino acid residues or nucleotides as compared to a second amino acid or nucleotide sequence, thus providing a common structural domain and/or indicating a common functional activity. Conservative nucleotide sequence variants include those nucleotide sequences that differ due to the degeneracy of the genetic code.

In general, amino acid sequences or nucleotide sequences that have at least about 45%, 55%, 65%, 70%, 75%, 80%, 85% or 90%, 91%, 92%, 93%, 94%, 95%, 95%, 96%, 97%, 98%, or 99% sequence identity to any of the amino acid sequences of even numbered SEQ ID NOS:1-36 or any of the nucleotide sequences of odd numbered SEQ ID NOS:1-36, respectively, are defined herein as sufficiently identical. Variant proteins encompassed by the present invention are biologically active, that is they continue to possess the desired biological activity of the native protein, that is, activity as described herein. A biologically active variant of a protein of the invention can differ from that protein by as few as 1-15 amino acid residues, as few as 1-10, such as 6-10, as few as 5, as few as 4, 3, 2, or even 1 amino acid residue.

In one embodiment of the invention, variants of polypeptides or polynucleotides of SEQ ID NOS:1, 2, 3, or 4 are provided. A variant of a polypeptide or polynucleotide of SEQ ID NO:1, 2, 3, or 4 can comprise, in general, amino acid sequences or nucleotide sequences that have at least about 45%, 55%, 65%, 70%, 75%, 80%, 85% or 90%, 91%, 92%, 93%, 94%, 95%, 95%, 96%, 97%, 98%, or 99% sequence identity to any of the amino acid sequences of SEQ ID NO:2 or 4 or any of the nucleotide sequences of SEQ ID NO:1 or 3, respectively. Biologically active variants can continue to be biologically active (i.e., have oxalate degrading activity).

In another embodiment of the invention, variants of polypeptides or polynucleotides of SEQ ID NOS:5-36 are provided. A variant of a polypeptide or polynucleotide of SEQ ID NO:5-36 can comprise, in general, amino acid sequences or nucleotide sequences that have at least about 45%, 55%, 65%, 70%, 75%, 80%, 85% or 90%, 91%, 92%, 93%, 94%, 95%, 95%, 96%, 97%, 98%, or 99% sequence identity to any of the amino acid sequences of even numbered SEQ ID NOS:5-36 or any of the nucleotide sequences of odd numbered SEQ ID NO:5-36, respectively. Biologically active variants can continue to be biologically active (i.e., have oxalate degrading activity or any other activity disclosed herein).

Naturally occurring variants can exist within a population (e.g., the *Lactobacillus Acidophilus* population). Such variants can be identified by using well-known molecular biology techniques, such as the polymerase chain reaction (PCR), and hybridization as described herein. Synthetically derived nucleotide sequences, for example, sequences generated by site-directed mutagenesis or PCR-mediated mutagenesis which still encode a protein, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) can be made at the N-terminal or C-terminal end of the native protein, or at one or more sites in the native protein. Similarly, a substitution of one or more nucleotides or amino acids can be made at one or more sites in the native protein.

For example, conservative amino acid substitutions can be made at one or more predicted, preferably nonessential, amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

Alternatively, mutations can be made randomly along all or part of the length of the coding sequence, such as by saturation mutagenesis. The mutants can be expressed recombinantly, and screened for those that retain biological activity by assaying for activity using standard assay techniques. Methods for mutagenesis and nucleotide sequence alterations are known in the art. See, for example, Kunkel (1985) *Proc. Natl. Acad. Sci. USA* 82:488-492; Kunkel et al. (1987) *Methods in Enzymol. Molecular Biology* (MacMillan Publishing Company, New York) and the references sited therein. Obviously the mutations made in the DNA encoding the variant must not disrupt the reading frame and preferably will not create complementary regions that could produce secondary mRNA structure. See, EP Patent Application Publication No. 75,444. Guidance as to appropriate amino acid substitutions that do not affect biological activity of the protein of interest can be found in the model of Dayhoff et al. (1978) *Atlas of Protein Sequence and Structure* (Natl. Biomed. Res. Found., Washington, D.C.), herein incorporated by reference.

The deletions, insertions, and substitutions of the amino sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide and amino acid sequences of the present invention also encompass sequences derived from mutagenic and recombinogenic procedures such as DNA shuffling. With such a procedure, one or more different protein coding regions can be used to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest can be shuffled between the gene of the invention and other known genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Variants of the proteins of this invention can function as either agonists (mimetics) or as antagonists. An agonist of the protein can retain substantially the same, or a subset, of the biological activities of the naturally occurring form of the protein. An antagonist of the protein can inhibit one or more of the activities of the naturally occurring form of the protein by, for example, competitively binding to a downstream or upstream member of a cellular signaling cascade that includes the protein.

Variants of a protein that function as either agonists or antagonists can be identified by screening combinatorial libraries of mutants, e.g., truncation mutants, of a protein for protein agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual polypeptides, or alternatively, as a set of larger fusion proteins (e.g., for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a protein coding sequence can be used to generate a variegated population of fragments for screening and subsequent selection of variants of a protein. In one embodiment, a library of coding sequence fragments can be generated by treating a double-stranded PCR fragment of a coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify variants (Arkin and Yourvan (1992) *Proc. Natl. Acad. Sci. USA* 89:7811-7815; Delgrave et al. (1993) *Protein Engineering* 6(3):327-331).

Sequence Identity

The sequences are members of multiple families of molecules, with conserved functional features. By "family" is meant two or more proteins or nucleic acid molecules having sufficient nucleotide or amino acid sequence identity. A family that contains deeply divergent groups can be divided into subfamilies. A clan is a group of families that are thought to have common ancestry. Members of a clan often have a similar tertiary structure.

By "sequence identity" is meant the nucleotide or amino acid residues that are the same when aligning two sequences for maximum correspondence over a specified comparison window. By "comparison window" is meant a contiguous segment of the two nucleotide sequences or amino acid sequences for optimal alignment, wherein the second sequence can contain additions or deletions (i.e., gaps) as compared to the first sequence. Generally, for nucleotide sequence alignments, the comparison window is at least 20 contiguous nucleotides in length, and optionally can be 30, 40, 50, 100, or longer. For amino acid sequence alignments, the comparison window is at least 6 contiguous amino acids in length, and optionally can be 10, 15, 20, 30, or longer. Those of skill in the art understand that to avoid a high similarity due to inclusion of gaps, a gap penalty is typically introduced and is subtracted from the number of matches.

Family members can be from the same or different species, and can include homologues as well as distinct proteins. Often, members of a family display common functional characteristics. Homologues can be isolated based on their identity to the nucleic acid sequences disclosed herein using the cDNA, or a portion thereof, as a hybridization probe according to standard hybridization techniques under stringent hybridization conditions as disclosed below.

To determine the percent identity of two amino acid or nucleotide sequences, an alignment is performed. Percent identity of the two sequences is a function of the number of identical residues shared by the two sequences in the comparison window (i.e., percent identity=number of identical residues/total number of residues×100). In one embodiment, the sequences are the same length. Methods similar to those mentioned below can be used to determine the percent identity between two sequences. The methods can be used with or without allowing gaps. Alignment can also be performed manually by inspection.

When amino acid sequences differ in conservative substitutions, the percent identity can be adjusted upwards to correct for the conservative nature of the substitution. Means for making this adjustment are known in the art. Typically the conservative substitution is scored as a partial, rather than a full mismatch, thereby increasing the percentage sequence identity.

Mathematical algorithms can be used to determine the percent identity of two sequences. Non-limiting examples of mathematical algorithms are the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877; the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; and the search-for-similarity-method of Pearson and Lipman (1988) *Proc. Natl. Acad. Sci. USA* 85:2444-2448.

Various computer implementations based on these mathematical algorithms have been designed to enable the determination of sequence identity. The BLAST programs of Altschul et al. (1990) *J. Mol. Biol.* 215:403 are based on the algorithm of Karlin and Altschul (1990) supra. Searches to obtain nucleotide sequences that are homologous to nucleotide sequences of the present invention can be performed with the BLASTN program, score =100, wordlength =12. To obtain amino acid sequences homologous to sequences encoding a protein or polypeptide of the current invention, the BLASTX program can be used, score =50, wordlength =3. Gapped alignments can be obtained by using Gapped BLAST as described in Altschul et al. (1997) *Nucleic Acids Res.* 25:3389. To detect distant relationships between molecules, PSI-BLAST can be used. See Altschul et al. (1997) supra. For all of the BLAST programs, the default parameters of the respective programs can be used.

Another program that can be used to determine percent sequence identity is the ALIGN program (version 2.0), which uses the mathematical algorithm of Myers and Miller (1988) supra. A PAM120 weight residue table, a gap length penalty of 12, and a gap penalty of 4 can be used with this program when comparing amino acid sequences.

In addition to the ALIGN and BLAST programs, the BESTFIT, GAP, FASTA and TFASTA programs are part of the Wisconsin Genetics Software Package (from GCG, Madison, Wis.), and can be used for performing sequence alignments. The preferred program is GAP version 10, which used the algorithm of Needleman and Wunsch (1970) supra. Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. Other equivalent programs can also be used. By "equivalent program" is meant any sequence comparison program that, for any two sequences in question, generates an alignment having identical nucleotide or amino acid residue matches and an identical percent sequence identity when compared to the corresponding alignment generated by GAP Version 10.

Identification and Isolation of Homologous Sequences

Nucleotide sequences identified based on their sequence identity to the nucleotide sequences set forth herein, or to fragments and variants thereof, are encompassed by the present invention. Methods such as PCR or hybridization can be used to identify sequences from a cDNA or genomic library, for example that are substantially identical to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Methods for construction of such cDNA and genomic libraries are generally known in the art and are also disclosed in the above references.

In hybridization techniques, the hybridization probes can be genomic DNA fragments, cDNA fragments, RNA fragments, or other oligonucleotides, and can consist of all or part of a known nucleotide sequence disclosed herein. In addition, they can be labeled with a detectable group such as $^{32}$P, or any other detectable marker, such as other radioisotopes, a fluorescence compound, an enzyme, or an enzyme co-factor. Probes for hybridization can be made by labeling synthetic oligonucleotides based on the known nucleotide sequences disclosed herein. Degenerate primers designed on the basis of conserved nucleotides or amino acid residues in a known nucleotide sequence or encoded amino acid sequence can additionally be used. The hybridization probe typically comprises a nucleotide sequence that hybridizes under stringent conditions to at least about 10, preferably about 20, more preferably about 50, 75, 100, 125, 150, 175, 200, 250, 300, 350, or 400 consecutive nucleotides of a nucleic acid of the invention or a fragment or variant thereof. To achieve specific hybridization under a variety of conditions, such probes can include sequences that are unique with respect to the encoded amino acid sequence. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

In one embodiment, the entire nucleotide sequence encoding a protein is used as a probe to identify novel nucleic acid sequences and messenger RNAs. In another embodiment, the probe is a fragment of a nucleotide sequence disclosed herein. In some embodiments, the nucleotide sequence that hybridizes under stringent conditions to the probe can be at least about 25, 50, 75, 100, 125, 150, 175, 200, 225, 250, 275, 300, 325, 350, 375, 400, 425, 450, 500, 550, 600, 650, 700, 800, 900, 1000, 2000, 3000, 4000, 5000, or more nucleotides in length.

Substantially identical sequences will hybridize to each other under stringent conditions. By "stringent conditions" is meant conditions under which a probe will hybridize to its target sequence to a detectably greater degree than to other sequences (e.g., at least 2-fold over background). Generally, stringent conditions encompasses those conditions for hybridization and washing under which nucleotide sequences having at least about 60%, 65%, 70%, preferably 75% sequence identity typically remain hybridized to each other. Stringent conditions are known in the art and can be found in *Current Protocols in Molecular Biology* (John Wiley & Sons, New York (1989)), 6.3.1-6.3.6.

Stringent conditions are sequence-dependent and will differ in different circumstances. Full-length or partial nucleic acid sequences can be used to obtain homologues and orthologs encompassed by the present invention. By "orthologs" are meant genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

When using probes, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

The post-hybridization washes are instrumental in controlling specificity. The two critical factors are ionic strength and temperature of the final wash solution. For the detection of sequences that hybridize to a full-length or approximately full-length target sequence, the temperature under stringent conditions is selected to be about 5° C. lower than the thermal melting point ($T_m$) for the specific sequence at a defined ionic strength and pH. However, stringent conditions would encompass temperatures in the range of 1° C. to 20° C. lower than the $T_m$, depending on the desired degree of stringency as otherwise qualified herein. For DNA-DNA hybrids, the $T_m$ can be determined using the equation of Meinkoth and Wahl (1984) *Anal. Biochem.* 138:267-284: $T_m=81.5°$ C.+16.6 (logM)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

The ability to detect sequences with varying degrees of homology can be obtained by varying the stringency of the hybridization and/or washing conditions. To target sequences that are 100% identical (homologous probing), stringency conditions must be obtained that do not allow mismatching. By allowing mismatching of nucleotide residues to occur, sequences with a lower degree of similarity can be detected (heterologous probing). For every 1% of mismatching, the $T_m$ is reduced about 1° C.; therefore, hybridization and/or wash conditions can be manipulated to allow hybridization of sequences of a target percentage identity. For example, if sequences with ≧90% sequence identity are preferred, the $T_m$ can be decreased by 10° C. Two nucleotide sequences could be substantially identical, but fail to hybridize to each other under stringent conditions, if the polypeptides they encode are substantially identical. This situation could arise, for example, if the maximum codon degeneracy of the genetic code is used to create a copy of a nucleic acid.

Exemplary low stringency conditions include hybridization with a buffer solution of 30-35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers can comprise about 0.1% to about 1% SDS. Duration of hybridization is generally less than about 24 hours, usually about 4 to about 12 hours. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning. A Laboratory Manual* (2d ed., Cold Spring Harbor Laboratory Press, Plainview, N.Y.). All of these references are incorporated herein in their entireties.

In amplification protocols, such as a PCR approach, oligonucleotide primers can be designed for use in PCR reactions to amplify corresponding DNA sequences from cDNA or genomic DNA extracted from any organism of interest. PCR primers are preferably at least about 10 or 15 nucleotides in length, and most preferably at least about 20, 25 or 30 nucleotides in length. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

Assays

Assays to detect expression of the disclosed polypeptides and/or nucleic acid molecules as well as their disclosed activity in a sample are provided herein. An exemplary method for detecting the presence or absence of a disclosed nucleic acid or protein comprising the disclosed polypeptide in a sample involves obtaining a sample from a food/dairy/feed product, starter culture (mother, seed, bulk/set, concentrated, dried, lyophilized, frozen), cultured food/dairy/feed product, dietary supplement, bioprocessing fermentate, or a subject that has ingested a probiotic material, and contacting the sample with a compound or an agent capable of interacting with the disclosed polypeptides or nucleic acids (e.g., an mRNA or genomic DNA comprising the disclosed nucleic acid or fragment thereof) in a manner such that the presence of the disclosed nucleic acid or protein is detected in the sample. Results obtained with a sample from the food, supplement, culture, product or subject can be compared to results obtained with a sample from a control, food, supplement culture, product or subject.

In some embodiments, one agent for detecting an mRNA or genomic DNA comprising a disclosed nucleotide sequence is a labeled nucleic acid probe capable of hybridizing to the disclosed nucleotide sequence of the mRNA or genomic DNA. The nucleic acid probe can be, for example, a disclosed nucleic acid molecule, such as a nucleic acid comprising a nucleotide sequence as set forth in SEQ ID NOS:1 or 3 or a fragment or variant thereof or odd numbered SEQ ID NO:5-36 or a variant or fragment thereof, such as a nucleic acid molecule of at least 5, 10, 15, 20, 25, 30, 35, 40, 45, 50, 75, 100, 125, 150, 175, 200, 250, 300, 400, or 500 nucleotides in length, including any number between 5 and 500 not specifically recited herein (e.g., 16, 34, 172), and sufficient to specifically hybridize under stringent conditions to the mRNA or genomic DNA comprising the disclosed nucleotide sequence. Other suitable probes for use in the assays of the invention are described herein.

In other embodiments, one agent for detecting a protein comprising a disclosed amino acid sequence is an antibody capable of binding to the disclosed polypeptide, preferably an antibody with a detectable label or capable of being detected. Antibodies can be polyclonal, or more preferably, monoclonal. An intact antibody, or a fragment thereof (e.g., Fab or F(ab')$_2$) can be used. The term "labeled," with regard to a probe or antibody, is meant to encompass direct labeling of the probe or antibody by coupling (i.e., physically linking) a detectable substance to the probe or antibody, as well as indirect labeling of the probe or antibody by reactivity with another (i.e., secondary) reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "sample" is meant to include tissues, cells, and biological fluids present in or isolated from a subject, as well as cells from starter cultures or food products carrying such cultures, or derived from the use of such cultures. That is, the detection methods of the invention can be used to detect nucleic acid or protein of this invention in a sample both in vitro and in vivo. In vitro techniques for detection of mRNA comprising a disclosed sequence include Northern hybridizations and in situ hybridizations. In vitro techniques for detection of a protein comprising a disclosed amino acid sequence include enzyme linked immunosorbent assays (ELISAs), Western blots, immunoprecipitations, and immunofluorescence. In vitro techniques for detection of DNA comprising the disclosed nucleotide sequences include Southern hybridizations. Furthermore, in vivo techniques for detection of a protein comprising a disclosed amino acid sequence include introducing into a subject a labeled antibody against the disclosed polypeptide. For example, the antibody can be labeled with a radioactive marker whose presence and location in a subject can be detected by standard imaging techniques.

In one embodiment, the sample contains protein molecules from a test subject that has consumed a probiotic material. Alternatively, the sample can contain mRNA or genomic DNA from a starter culture.

The invention also encompasses kits for detecting the presence of disclosed nucleic acids or proteins in a sample. Such kits can be used to determine if a microbe expressing a specific polypeptide of the invention is present in a food product or starter culture, or in a subject that has consumed a probiotic material. For example, the kit can comprise a labeled compound or agent capable of detecting a disclosed polypeptide or nucleic acid in a sample and means for determining the amount of a the disclosed polypeptide or nucleic acid in the sample (e.g., an antibody that recognizes the disclosed polypeptide or an oligonucleotide probe that binds to DNA encoding a disclosed polypeptide, e.g., as set forth in SEQ ID NOS:2 or 4, or SEQ ID NOS:5-36). Kits can also include instructions detailing the use of such compounds.

For antibody-based kits, the kit can comprise, for example: (1) a first antibody (e.g., attached to a solid support) that binds to a disclosed polypeptide; and, optionally, (2) a second, different antibody that binds to the disclosed polypeptide or the first antibody and is conjugated to a detectable agent. For oligonucleotide-based kits, the kit can comprise, for example: (1) an oligonucleotide, e.g., a detectably labeled oligonucleotide, that hybridizes to a disclosed nucleic acid sequence or (2) a pair of primers useful for amplifying a disclosed nucleic acid molecule, and optionally a probe for detecting the amplification product.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

In one embodiment, the kit comprises multiple probes in an array format, such as those described, for example, in U.S. Pat. Nos. 5,412,087, 5,545,531, and PCT Publication No. WO 95/00530, herein incorporated by reference. Probes for use in the array can be synthesized either directly onto the surface of the array, as disclosed in PCT Publication No. WO 95/00530, or prior to immobilization onto the array surface (Gait, ed., *Oligonucleotide synthesis a practical approach*, IRL Press: Oxford, England, 1984). The probes can be immobilized onto the surface using techniques well known to one of skill in the art, such as those described in U.S. Pat. No. 5,412,087. Probes can be a nucleic acid or peptide sequence, preferably purified, or an antibody.

The arrays can be used to screen organisms, samples, or products for differences in their genomic, cDNA, polypeptide or antibody content, including the presence or absence of specific sequences or proteins, as well as the concentration of those materials. Binding to a capture probe is detected, for example, by signal generated from a label attached to the nucleic acid molecule comprising the disclosed nucleotide sequence, a polypeptide comprising the disclosed amino acid sequence, or an antibody. The method can include contacting the molecule comprising the disclosed nucleic acid, polypeptide, or antibody with a first array having a plurality of capture probes and a second array having a different plurality of capture probes. The results of each hybridization can be compared to analyze differences in expression between a first and second sample. The first plurality of capture probes can be from a control sample, e.g., a wild type lactic acid bacteria, or control subject, e.g., a food, dietary supplement, starter culture sample or a biological fluid. The second plurality of capture probes can be from an experimental sample, e.g., a mutant type lactic acid bacteria, or subject that has consumed a probiotic material, e.g., a starter culture sample or a biological fluid.

These assays can be especially useful in microbial selection and quality control procedures where the detection of unwanted materials is essential. The detection of particular nucleotide sequences or polypeptides can also be useful in determining the genetic composition of food, fermentation products, or industrial microbes, or microbes present in the digestive system of animals or humans that have consumed probiotics.

Antisense Nucleotide Sequences

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to a noncoding region of the coding strand of a nucleotide sequence encoding a protein. The noncoding regions are the 5' and 3' sequences that flank the coding region and are not translated into amino acids. Antisense nucleotide sequences are useful in disrupting the expression of the target gene. Antisense constructions having 70% or 75%, preferably 80%, and more preferably 85% or 90% sequence identity to the corresponding sequence can be used.

Given the coding-strand sequence encoding a polypeptide disclosed herein (e.g., SEQ ID NO:2 or 4 or even numbered SEQ ID NOS:5-36), antisense nucleic acids of the invention can be designed according to the rules of Watson and Crick base pairing. The antisense nucleic acid molecule can be complementary to the entire coding region of a mRNA, but more preferably is an oligonucleotide that is antisense to only a portion of the coding or noncoding region of a mRNA. For example, the antisense oligonucleotide can be complementary to the region surrounding the translation start site of an mRNA. An antisense oligonucleotide can be, for example, about 5, 10, 15, 20, 25, 30, 35, 40, 45, 50, 75, 100, 150, 200, 250, 300, 350, 400, 450 or 500 nucleotides in length, or it can be 100, 200 nucleotides, or greater in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave mRNA transcripts to thereby inhibit translation of mRNA. A ribozyme having specificity for an encoding nucleic acid can be designed based upon the nucleotide sequence of a nucleotide disclosed herein (e.g., odd numbered SEQ ID NOS:1-2556). See, e.g., Cech et al., U.S. Pat. No. 4,987,071; and Cech et al., U.S. Pat. No. 5,116,742. Alternatively, mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, gene expression can be inhibited by targeting nucleotide sequences complementary to the regulatory region of the protein (e.g., the promoter and/or enhancers) to form triple helical structures that prevent transcription of the gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In some embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996), supra; Perry-O'Keefe et al. (1996) *Proc. Natl. Acad. Sci. USA* 93:14670.

PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra); or as probes or primers for DNA sequence and hybridization (Hyrup (1996), supra; Perry-O'Keefe et al. (1996), supra).

In another embodiment, PNAs of a molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996)

Nucleic Acids Res. 24(17):3357-63; Mag et al. (1989) Nucleic Acids Res. 17:5973; and Peterson et al. (1975) Bioorganic Med. Chem. Lett. 5:1119.

Fusion Proteins

The invention also includes chimeric or fusion proteins. A "chimeric protein" or "fusion protein" comprises a first polypeptide operably linked (e.g., fused in-frame) to a second polypeptide. A "first polypeptide" refers to a polypeptide having an amino acid sequence corresponding to a first protein, whereas a "second polypeptide" refers to a polypeptide having an amino acid sequence corresponding to a protein that is not substantially identical to the first protein, and which is derived from the same or a different organism. Within a fusion protein, the polypeptide can correspond to all or a portion of a protein, preferably including at least one biologically active portion of a protein. Within the fusion protein, the term "operably linked" is meant to indicate that the first polypeptide and the second polypeptide are fused in-frame to each other. The second polypeptide can be fused to the N-terminus or C-terminus of the first polypeptide.

Expression of the linked coding sequences results in two linked heterologous amino acid sequences which form the fusion protein. The carrier sequence (the second polypeptide) encodes a carrier polypeptide that, for example, potentiates or increases expression of the fusion protein in the bacterial host. The portion of the fusion protein encoded by the carrier sequence, i.e., the carrier polypeptide, can be a protein fragment, an entire functional moiety, or an entire protein sequence. The carrier region or polypeptide can additionally be designed to be used in purifying the fusion protein, either with antibodies or with affinity purification specific for that carrier polypeptide. Likewise, physical properties of the carrier polypeptide can be exploited to allow selective purification of the fusion protein.

Particular carrier polypeptides of interest include superoxide dismutase (SOD), maltose-binding protein (MBP), glutathione-S-transferase (GST), an N-terminal histidine (His) tag, and the like. This list is not intended to be limiting, as any carrier polypeptide that potentiates expression of the protein as a fusion protein can be used in the methods of the invention.

In one embodiment, the fusion protein is a GST-fusion protein in which the sequences are fused to the C-terminus of the GST sequences. In another embodiment, the fusion protein is an immunoglobulin fusion protein in which all or part of a protein is fused to sequences derived from a member of the immunoglobulin protein family. The immunoglobulin fusion proteins of the invention can be used as immunogens to produce antibodies in a subject, to purify ligands, and in screening assays to identify molecules that inhibit the interaction of a protein with a ligand.

In one embodiment of the invention, the fusion protein has the ability to modify the functional properties of a bacterial cell. By "functional properties" is meant a bacterium's ability to perform certain non-native functions, such as those, for example, related to adhesion, immune stimulation, or lysis. The protein can include, but is not limited to, an antibody, an enzyme, an antigen, a protein with bactericidal activity, or a protein with receptor-binding activity. By "bactericidal activity" is meant the ability to kill one or more bacteria. By "receptor-binding activity" is meant the ability to bind to a receptor on a cell membrane, cell surface, or in solution. Methods to assess the ability of a fusion protein expressed on the surface of gram-positive bacteria to be used as a vaccine are known in the art (see, for example, Fischetti et al. (1996) Curr. Opin. Biotechnol. 7:659-666; Pouwels et al. (1998) Int. J. Food Microbiol. 41:155-167).

One of skill in the art will recognize that the particular carrier polypeptide can be chosen with the purification scheme in mind. For example, His tags, GST, and maltose-binding protein represent carrier polypeptides that have readily available affinity columns to which they can be bound and eluted. Thus, where the carrier polypeptide is an N-terminal His tag such as hexahistidine ($His_6$ tag), the fusion protein can be purified using a matrix comprising a metal-chelating resin, for example, nickel nitrilotriacetic acid (Ni-NTA), nickel iminodiacetic acid (Ni-IDA), and cobalt-containing resin (Co-resin). See, for example, Steinert et al. (1997) QIAGEN News 4:11-15, herein incorporated by reference in its entirety. Where the carrier polypeptide is GST, the fusion protein can be purified using a matrix comprising glutathione-agarose beads (Sigma or Pharmacia Biotech); where the carrier polypeptide is a maltose-binding protein (MBP), the fusion protein can be purified using a matrix comprising an agarose resin derivatized with amylose.

Preferably, a chimeric or fusion protein of the invention is produced by standard recombinant DNA techniques. For example, DNA fragments coding for the different polypeptide sequences can be ligated together in-frame, or the fusion nucleotide sequence can be synthesized, such as with automated DNA synthesizers. Alternatively, PCR amplification of nucleic acid fragments can be carried out using anchor primers that give rise to complementary overhangs between two consecutive nucleic acid fragments, which can subsequently be annealed and re-amplified to generate a chimeric nucleotide sequence (see, e.g., Ausubel et al., eds. (1995) Current Protocols in Molecular Biology) (Greene Publishing and Wiley-Interscience, NY). Moreover, a FOS-related-protein-encoding nucleic acid can be cloned into a commercially available expression vector such that it is linked in-frame to an existing fusion moiety.

The fusion protein expression vector is typically designed for ease of removing the carrier polypeptide to allow the protein to retain the native biological activity associated with it. Methods for cleavage of fusion proteins are known in the art. See, for example, Ausubel et al., eds. (1998) Current Protocols in Molecular Biology (John Wiley & Sons, Inc.). Chemical cleavage of the fusion protein can be accomplished with reagents such as cyanogen bromide, 2-(2-nitrophenyl-sulphenyl)-3-methyl-3'-bromoindolenine, hydroxylamine, or low pH. Chemical cleavage is often accomplished under denaturing conditions to cleave otherwise insoluble fusion proteins.

Where separation of the polypeptide from the carrier polypeptide is desired and a cleavage site at the junction between these fused polypeptides is not naturally occurring, the fusion construct can be designed to contain a specific protease cleavage site to facilitate enzymatic cleavage and removal of the carrier polypeptide. In this manner, a linker sequence comprising a coding sequence for a peptide that has a cleavage site. specific for an enzyme of interest can be fused in-frame between the coding sequence for the carrier polypeptide (for example, MBP, GST, SOD, or an N-terminal His tag) and the coding sequence for the polypeptide. Suitable enzymes having specificity for cleavage sites include, but are not limited to, factor Xa, thrombin, enterokinase, remin, collagenase, and tobacco etch virus (TEV) protease. Cleavage sites for these enzymes are well known in the art. Thus, for example, where factor Xa is to be used to cleave the carrier polypeptide from the polypeptide, the fusion construct can be designed to comprise a linker sequence encoding a factor Xa-sensitive cleavage site, for example, the sequence IEGR (see, for example, Nagai and Thøgersen (1984) Nature 309:810-812, Nagai and Thøgersen (1987) Meth. Enzymol. 153:

461-481, and Pryor and Leiting (1997) *Protein Expr. Purif.* 10(3):309-319, herein incorporated by reference). Where thrombin is to be used to cleave the carrier polypeptide from the polypeptide, the fusion construct can be designed to comprise a linker sequence encoding a thrombin-sensitive cleavage site, for example the sequence LVPRGS or VIAGR (see, for example, Pryor and Leiting (1997) *Protein Expr. Purif.* 10(3):309-319, and Hong et al. (1997) *Chin. Med. Sci. J.* 12(3): 143-147, respectively, herein incorporated by reference). Cleavage sites for TEV protease are known in the art. See, for example, the cleavage sites described in U.S. Pat. No. 5,532,142, herein incorporated by reference in its entirety. See also the discussion in Ausubel et al., eds. (1998) *Current Protocols in Molecular Biology* (John Wiley & Sons, Inc.), Chapter 16.

Antibodies

An isolated polypeptide of the present invention can be used as an immunogen to generate antibodies that specifically bind proteins, or stimulate production of antibodies in vivo. The full-length protein can be used as an immunogen or, alternatively, antigenic peptide fragments of proteins as described herein can be used. The antigenic peptide of a protein can comprise at least 5, 10, 15, 20, 25, 30, 35, 40, 45, or 50 amino acid residues, or any number in between 5 and 50 not specifically recited herein (e.g., 12, 27, 43) of the amino acid sequences as set forth in SEQ ID NOS:2 or 4 or even numbered SEQ ID NO:5-36 or variants and fragments thereof and encompasses an epitope of an protein such that an antibody raised against the peptide forms a specific immune complex with the protein. Preferred epitopes encompassed by the antigenic peptide are regions of a protein that are located on the surface of the protein, e.g., hydrophilic regions.

Recombinant Expression Vectors

The nucleic acid molecules of the present invention can be included in vectors, preferably expression vectors. "Vector" refers to a nucleic acid molecule capable of transporting another nucleic acid to which it has been linked. Expression vectors include one or more regulatory sequences and direct the expression of nucleic acids to which they are operably linked. By "operably linked" is meant that the nucleotide sequence of interest is linked to the regulatory sequence(s) such that expression of the nucleotide sequence is allowed (e.g., in an in vitro transcription/translation system or in a cell when the vector is introduced into the cell). As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. The term "regulatory sequence" is meant to include, for example, controllable transcriptional promoters, operators, enhancers, transcriptional terminators, and/or other expression control elements such as translational control sequences (e.g., Shine-Dalgarno consensus sequence, initiation and termination codons). These regulatory sequences will differ, for example, depending on the cell being used.

The vectors can be autonomously replicated in a cell (episomal vectors), or can be integrated into the genome of a cell, and replicated along with the cell's genome (non-episomal mammalian vectors). Integrating vectors typically contain at least one sequence homologous to the bacterial chromosome that allows for recombination to occur between homologous DNA in the vector and the bacterial chromosome. Integrating vectors can also comprise bacteriophage or transposon sequences. Episomal vectors, or plasmids are circular double-stranded DNA loops into which additional DNA segments can be ligated. Plasmids capable of stable maintenance in a host are generally the preferred form of expression vectors when using recombinant DNA techniques.

The expression constructs or vectors encompassed in the present invention comprise a nucleic acid construct of the invention in a form suitable for expression of the nucleic acid in a cell. Expression in prokaryotic cells is encompassed in the present invention. It will be appreciated by those skilled in the art that the design of the expression vector can depend on such factors as the choice of the cell to be transformed, the level of production of protein desired, etc. The expression vectors of the invention can be introduced into cells to thereby produce proteins or peptides, including fusion proteins or peptides, encoded by nucleic acids as described herein (e.g., proteins, mutant forms of proteins, fusion proteins, etc.).

Regulatory sequences include those that direct constitutive expression of a nucleotide sequence as well as those that direct inducible expression of the nucleotide sequence only under certain conditions. A bacterial promoter is any DNA sequence capable of binding bacterial RNA polymerase and initiating the downstream (3') transcription of a coding sequence (e.g., structural gene) into mRNA. A promoter will have a transcription initiation region, which is usually placed proximal to the 5' end of the coding sequence. This transcription initiation region typically includes an RNA polymerase binding site and a transcription initiation site. A bacterial promoter can also have a second domain called an operator, which can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence.

An example of a gene activator protein is the catabolite activator protein (CAP), which helps initiate transcription of the lac operon in *Escherichia coli* (Raibaud et al. (1984) *Annu. Rev. Genet.* 18:173). Regulated expression can therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter. Any suitable promoter can be used to carry out the present invention, including the native promoter or a heterologous promoter. Heterologous promoters can be constitutively active or inducible. A non-limiting example of a heterologous promoter is given in U.S. Pat. No. 6,242,194 to Kullen and Klaenhammer.

Sequences encoding metabolic pathway enzymes provide particularly useful promoter sequences. Examples include promoter sequences derived from sugar metabolizing enzymes, such as galactose, lactose (lac) (Chang et al. (1987) *Nature* 198:1056), and maltose. Additional examples include promoter sequences derived from biosynthetic enzymes such as tryptophan (trp) (Goeddel et al. (1980) *Nucleic Acids Res.* 8:4057; Yelverton et al. (1981) *Nucleic Acids Res.* 9:731; U.S. Pat. No. 4,738,921; EPO Publication Nos. 36,776 and 121, 775). The beta-lactamase (bla) promoter system (Weissmann (1981) "The Cloning of Interferon and Other Mistakes," in *Interferon* 3 (ed. I. Gresser); bacteriophage lambda PL (Shimatake et al. (1981) *Nature* 292:128); the arabinose-inducible araB promoter (U.S. Pat. No. 5,028,530); and T5 (U.S. Pat. No. 4,689,406) promoter systems also provide useful promoter sequences. See also Balbas (2001) *Mol. Biotech.* 19:251-267, where *E. coli* expression systems are discussed.

In addition, synthetic promoters that do not occur in nature also function as bacterial promoters. For example, transcription activation sequences of one bacterial or bacteriophage promoter can be joined with the operon sequences of another bacterial or bacteriophage promoter, creating a synthetic hybrid promoter (U.S. Pat. No. 4,551,433). For example, the tac (Amann et al. (1983) *Gene* 25:167; de Boer et al. (1983) *Proc. Natl. Acad. Sci.* 80:21) and trc (Brosius et al. (1985) *J. Biol. Chem.* 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter can also be comprised of a bacteriophage promoter and an *E. coli* operator region (EPO Publication No. 267,851).

The vector can additionally comprise a nucleic acid encoding the repressor (or inducer) for that promoter. For example, an inducible vector of the present invention can regulate transcription from the Lac operator (LacO) by expressing a nucleic acid encoding the LacI repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., λ.CI857, rendering λ.pL thermo-inducible, or λ.CI+, rendering λ.pL chemo-inducible) can be employed.

In addition to a functioning promoter sequence, an efficient ribosome-binding site is also useful for the expression of the fusion construct. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) *Nature* 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in *Biological Regulation and Development: Gene Expression* (ed. R. F. Goldberger, Plenum Press, NY).

Proteins can also be secreted from the cell by creating chimeric DNA molecules that encode a protein comprising a signal peptide sequence that provides for secretion of the polypeptide in bacteria (U.S. Pat. No. 4,336,336). The signal sequence fragment typically encodes a signal peptide comprised of hydrophobic amino acids that directs the secretion of the protein from the cell. The protein is either secreted into the growth medium (Gram-positive bacteria) or into the periplasmic space, located between the inner and outer membrane of the cell (gram-negative bacteria). Preferably there are processing sites, which can be cleaved either in vivo or in vitro, encoded between the signal peptide sequence and the protein.

DNA encoding suitable signal sequences can be derived from genes for secreted bacterial proteins, such as the *E. coli* outer membrane protein gene (ompA) (Masui et al. (1983) *FEBS Lett.* 151(1):159-164; Ghrayeb et al. (1984) *EMBO J.* 3:2437-2442) and the *E. coli* alkaline phosphatase signal sequence (phoA) (Oka et al. (1985) *Proc. Natl. Acad. Sci.* 82:7212). Other prokaryotic signals include, for example, the signal sequence from penicillinase, Ipp, or heat stable enterotoxin II leaders.

Typically, transcription termination sequences recognized by bacteria are regulatory regions located 3' to the translation stop codon and thus, together with the promoter, flank the coding sequence. These sequences direct the transcription of mRNA that can be translated into the polypeptide encoded by the DNA. Transcription termination sequences frequently include DNA sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

The expression vectors will have a plurality of restriction sites for insertion of the sequence so that it is under transcriptional regulation of the regulatory regions. Selectable marker genes that ensure maintenance of the vector in the cell can also be included in the expression vector. Examples of selectable markers include those that confer resistance to drugs such as ampicillin, chloramphenicol, erythromycin, kanamycin (neomycin), and tetracycline (Davies et al. (1978) *Annu. Rev. Microbiol.* 32:469). Selectable markers can also allow a cell to grow on minimal medium, or in the presence of toxic metabolites and can include biosynthetic genes, such as those in the histidine, tryptophan, and leucine biosynthetic pathways.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The regulatory regions can be native (homologous), or can be foreign (heterologous) to the cell and/or the nucleotide sequence of the invention. The regulatory regions can also be natural or synthetic. Where the region is "foreign" or "heterologous" to the nucleotide sequence of the invention, it is meant that the region is not the native or naturally occurring region for the operably linked nucleotide sequence of the invention. For example, the region can be derived from phage. While sequences can be expressed using heterologous regulatory regions, native regions can be used. Such constructs would be expected in some cases to alter expression levels of proteins in the cell. Thus, the phenotype of the cell can be altered.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to mRNA. Regulatory sequences operably linked to a nucleic acid cloned in the antisense orientation can be chosen to direct the continuous or inducible expression of the antisense RNA molecule. The antisense expression vector can be in the form of a recombinant plasmid or phagemid in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Alternatively, some of the above-described components can be put together in transformation vectors. Transformation vectors are typically comprised of a selectable market that is either maintained in a replicon or developed into an integrating vector, as described above.

Microbial or Bacterial Cells

The production of bacteria containing the nucleic acid sequences or proteins of this invention, the preparation of starter cultures of such bacteria, and methods of fermenting substrates, particularly food substrates such as milk, can be carried out in accordance with known techniques. (See, for example, Gilliland, S. E. (ed) *Bacterial Starter Cultures for Food*, CRC press, 1985, 205 pp.; Read, G. (Ed.) *Prescott and Dunn's Industrial Microbiology*, 4$^{th}$ Ed., AVI Publishing Company, Inc. 1982, 883 pp.; Peppler, J. J. and Perlman, D. (Eds.) *Microbial Technology: Volume II, Fermentation Technology*, Academic Press, 1979, 536 pp.)

By "fermenting" is meant the energy-yielding, metabolic breakdown of organic compounds by microorganisms that generally proceed under anaerobic conditions and with the evolution of gas.

By "introducing" as it pertains to nucleic acid molecules is meant introduction into cells (e.g., prokaryotic cells) via conventional transformation or transfection techniques, or by phage-mediated infection. As used herein, the terms "transformation," "transduction," "conjugation," and "protoplast fusion" are intended to refer to a variety of art-recognized techniques for introducing foreign nucleic acid (e.g., DNA) into a cell, including calcium phosphate or calcium chloride co-precipitation, DEAE-dextran-mediated transfection, lipofection, or electroporation. Suitable methods for transforming or transfecting cells can be found in Sambrook et al. (1989) *Molecular Cloning: A Laboratory Manual* (2d ed., Cold Spring Harbor Laboratory Press, Plainview, N.Y.) and other laboratory manuals. By "introducing" as it pertains to polypeptides or microorganisms of the invention, is meant introduction into a host by ingestion, topical application, nasal, urogenital, suppository, or oral application of the polypeptide or microorganism.

Bacterial cells used to produce the polypeptides of this invention are cultured in suitable medium, as described generally in Sambrook et al. (1989) *Molecular Cloning, A Laboratory Manual* (2d ed., Cold Spring Harbor Laboratory Press, Plainview, N.Y.).

Modulating Oxalate Degradation

Figure 2:
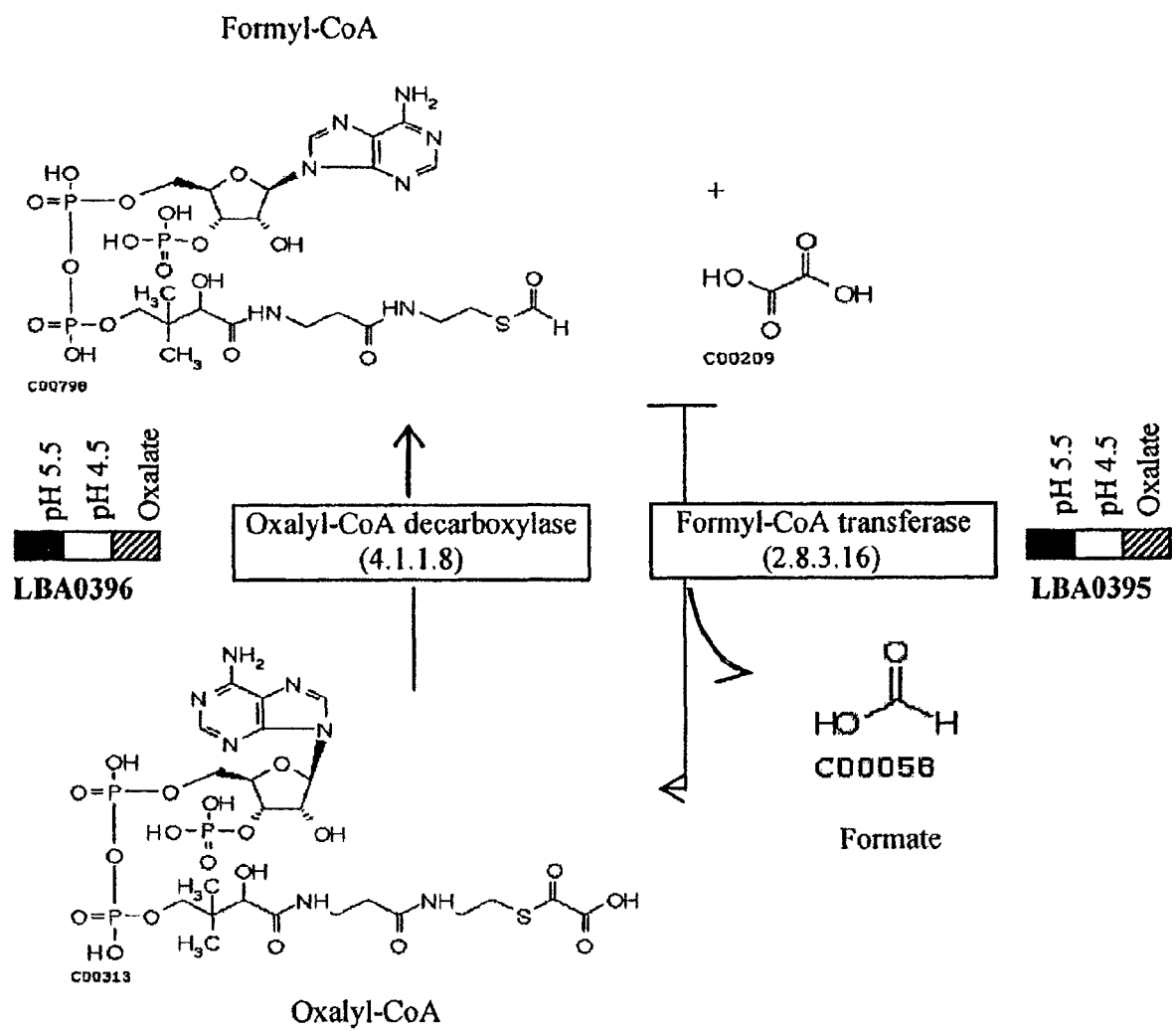
FIG. 2 shows the proposed metabolic pathway of oxalate decarboxylation by *L. acidophilus* is also shown.

Methods and compositions for degrading oxalate are provided. Oxalate is catabolized through a series of enzymatic reactions. Two general mechanisms for oxalate degradation include decarboxylation to yield formic acid and $CO_2$ and oxidation to yield hydrogen peroxide and $CO_2$. The decarboxylation process can be accomplished either aerobically or anaerobically, while the oxidation process is strictly aerobic. In the decarboxlation reaction, oxalate is reduced by a formyl coenzyme A transferase (formyl-CoA transferase; E.C. 2.8.3) which activates the oxalate molecule by cycling a CoA moiety from formyl-CoA. Next, the oxalyl-coenzyme A decarboxylase (oxalyl-CoA decarboxylase; E.C. 4.1.1.8) decarboxylates the activated oxalate molecule. As demonstrated herein, this pathway of oxalate degradation has now been identified in *Lactobacillus acidophilus*. FIG. 2 provides a schematic of this oxalate degradation pathway. Accordingly, the present invention provides methods and compositions related to modulating oxalate degradation.

Compositions comprising the oxalate degrading polynucleotides and polypeptides set forth in SEQ ID NOS:1 and 2 are provided. SEQ ID NOS:1 and 2 encode a member of the formyl-CoA transferase family. As used herein, "formyl-CoA transferase activity" catalyzes the transfer of CoA from formyl-CoA to either oxalate or succinate. Methods to assay for this activity are known. See, for example, Baetz et al. (1990) *Journal of Bacteriology* 172:3537-3540, herein incorporated by reference. These sequences, along with variant and fragments thereof, can be used to modulate the oxalate degrading activity of an organism of interest.

Further provided are compositions comprising the oxalate degrading polynucleotides and polypeptides set forth in SEQ ID NOS:3 and 4. SEQ ID NOS:3 and 4 encode an oxalyl-CoA decarboxylase. As used herein, polypeptides having "oxalyl-CoA decarboxylase activity" decarboxylates the activated oxalate molecule. Methods to assay for this activity are known. For example, the consumption of oxalyl-CoA and the production of formyl-CoA can be monitored by capillary electrophoresis. See, for example, Federici et al. (2004) *Applied and Environmental Microbiology* 70:5066-5073 and Lung et al. (1994) *Journal of Bacteriology* 176:2468-2472, each of which is herein incorporated by reference. These sequences, along with variants and fragments thereof, can be used to modulate the oxalate degrading activity of an organism of interest.

Compositions of the invention further include various polynucleotides and polypeptides that are differentially expressed in *Lactobacillus acidophilius* in response to 1% ammonium oxalate at pH 6.8. Such polypeptides and polynucleotides are set forth in SEQ ID NOS:5-36. In one embodiment, such sequences can find use in modulating oxalate degradation or any other method disclosed herein.

As used herein, the terms "oxalate degrading" and "oxalate reducing" activity are interchangeable and both refer to the reduction or degradation of oxalate. Oxalate degrading activity includes formyl-CoA transferase activity, oxalyl-CoA decarboxylase activity, or any activity employed in an enzymatic pathway that decreases the level of oxalate in a sample. As defined herein "modulating oxalate degradation" is intended any statistically significant increase or decrease in oxalate levels in a sample when compared to an appropriate control. Thus, an effective concentration of an oxalate degrading sequence or microbe is a concentration that is sufficient to modulate oxalate degradation. Assays to measure oxalate degradation include, but are not limited to, the assays discussed above for formyl-CoA transferase activity and oxalyl-CoA decarboxylase activity. In addition, assays for oxalate degradation include direct measurement of oxalate concentration. See, for example, Duncan et al. (2002) *Applied and Environmental Microbiology* 68:3841-3847, herein incorporated by reference.

In one embodiment, an appropriate host cell is transformed with at least one of the polynucleotides encoding the oxalate degrading sequences of the invention, or a biologically active variant or fragment thereof, and thereby confer upon the transformed host cell a modulated oxalate degradation activity (i.e., an increase or decrease in oxalate degradation activity) than that seen in an appropriate host control cell. The host can comprise, for example, a microbe which is particularly well adapted for oral administration and/or colonizing the intestines. Alternatively, the host may be a plant or plant cell which, once transformed, will produce the desired oxalate degrading polypeptides and thereby make these activities available in the intestine when the plant material is consumed. Alternatively, the transformed plant may have a lower amount of oxalate, due to the actions of the polypeptides provided by the transformation, and thus when consumed, the plant will not provide as much oxalate to the diet as would a nontransformed plant. The oxalate degrading polynucleotides may also be used in synthetic or ex vivo systems to provide proteins having oxalate degrading activity.

Compositions further comprise microorganisms that are capable of degrading oxalate. In one embodiment, the microorganism comprises a bacteria having a first nucleic acid comprising the nucleic acid set forth in SEQ ID NO:1 or a biologically active variant or fragment thereof; and, a second nucleic acid molecule comprising a nucleotide sequence as set forth in SEQ ID NO:3 or a biologically active variant or fragment thereof, where at least one of the first or the second nucleic acid molecules is heterologous to the bacteria, and the first and the second nucleic acid molecules are operably linked to a promoter active is the bacteria. In specific embodiments, both nucleic acids are heterologous to the microorganism.

The microorganism employed in the methods and compositions of the invention can comprise a probiotic bacteria, a lactic acid bacteria, *Lactobacillus*, or *Lactobacillus acidophilus*. Other microorganisms of interest include, but are not limited to, *Oxalobacter formigenes, Pseudomonas, Clostridia*, or *Bifidobacteria*. It is recognized that the native microorganism employed can be capable of degrading oxalate, but also includes microorganisms, such as bacteria or fungi, that are unable to degrade oxalate and thus when transformed with the heterologous oxalate degrading polynucleotides of the invention, the oxalate degrading ability is conferred. Methods of expressing and isolating the oxalate degrading polypeptide or various methods for introducing such sequences into a microbe are known in the art and disclosed in detail elsewhere herein.

Compositions of the present invention also include subjects (i.e., animals including, humans and non-human animals, such as, domesticated, agricultural, or exotic animals) that have a modulated oxalate degrading activity. In specific embodiments, such subjects have an enhanced ability to reduce oxalate. Such animals having enhanced oxalate degradation abilities can be used as in vivo models for studying oxalate-related conditions.

Methods are provided to modulate the oxalate degrading capability of a cell or an organism. In one method, oxalate degrading sequences of the invention are provided to a cell to enhance or repress the oxalate degrading ability of the cell. In other methods, compositions comprising the oxalate degrading sequences of the present invention and/or the oxalate degrading microbes expressing the oxalate degrading sequences of the invention are administered to plants or animals for altering the oxalate levels of the plant or animal. Methods also include dietary supplementation methods such that the compositions of the present invention are administered to animals in food or concurrent with food to alter the oxalate levels in the food or during the digestion of the food.

Further provided is a method for reducing oxalate levels in order to treat or prevent oxalate-related conditions. By "oxalate-related condition" is intended any condition which results in an elevated level of oxalate in a subject. Subjects which could benefit from preventative treatment include, but are not limited to, individuals or animals whose oxalate degrading bacteria have been depleted due to, for example, antibiotic treatment or in post-operative situations. The methods of the invention can also be used to treat individuals or animals who have colonies of oxalate degrading bacteria, but who still have unhealthy levels of oxalate due to, for example, oxalate susceptibility and/or excessive production of endogenous oxalate. Non-limiting oxalate-related conditions include hyperoxaluria, primary hyperoxaluria, idiopathic calcium oxalate kidney stone disease (urolithiasis), enteric hyperoxaluria, vulvodynia, oxalosis associated with end-stage renal disease, cardiac conductance disorders, inflammatory bowel disease, Crohn's disease, and ulcerative colitis.

By "treatment" is intended any improvement in the subject having the oxalate-related condition. The improvement can be characterized as any statistically significant reduction in the level of oxalate in the subject. Accordingly, a "positive therapeutic response" includes both a complete response (i.e., a reduction to normal oxalate levels) and a partial response (i.e., any statistically significant reduction in oxalate levels). Various assays can be used to measure the level of oxalate present in the gut, kidney, feces, or in various cellular or body fluids, such as, blood or urine. See, for example, Duncan et al. (2002) *Applied and Environmental Microbiology* 68:3841-3847.

A method for treating an oxalate-related condition comprises administering a composition comprising one or more oxalate degrading microbes and/or oxalate-degrading polypeptides of the invention. The oxalate degrading polypeptide which is administered in the methods of the invention may be isolated or they may be administered as a cell lysate. The cell lysate can be made from any host cell that is expressing the oxalate degrading sequence of the invention, or a biologically active variant or fragment thereof. In one embodiment, the cell lysate is from *Lactobacillus acidophilus*. In a specific embodiment, the oxalate degrading sequences which are administered comprise one or more of the oxalate degrading sequences of the present invention such as, but not limited to, SEQ ID NO:1, 2, 3, or 4 or a biologically active variant or fragment thereof. In other embodiments, the sequences administered comprise one or more of the sequences as set forth in SEQ ID NOS:5-36, or a biologically active variant or fragment thereof. Additional factors which improve the oxalate degrading activity can also be administered.

Further provided is a composition comprising one or more oxalate degrading microbes and/or oxalate-degrading polypeptides and/or cell lysate of the invention for use as a medicament. Also provided is the use of a composition comprising one or more oxalate degrading microbes and/or oxalate-degrading polypeptides of the invention in the manufacture of a medicament for use in the treatment of an oxalate-related condition.

The present invention yet further provides the use of a composition comprising one or more oxalate degrading microbes and/or oxalate-degrading polypeptides and/or cell lysate of the invention in the manufacture of a medicament for use in the treatment of a non-limiting oxalate-related condition including one or more of hyperoxaluria, primary hyperoxaluria, idiopathic calcium oxalate kidney stone disease (urolithiasis), enteric hyperoxaluria, vulvodynla, oxalosis associated with end-stage renal disease, cardiac conductance disorders, inflammatory bowel disease, Crohn's disease, and ulcerative colitis.

When an oxalate degrading microbe expressing at least one of the oxalate degrading polynucleotides of the invention is employed, the microbe and its progeny replicate in the intestine of the subject and remove oxalate from the intestinal tract, thereby reducing the amount of oxalate available for absorption which leads to increased oxalate excretion from the blood into the intestine.

Such compositions may be administered one or more times a day for one or more days depending on the severity of the oxalate-related condition or the amount of oxalate in the gut or body fluids of the human or animal. The treatments may continue as long as unwanted levels or oxalate are present in the human or animal. In still another embodiment, the composition is administered to reduce the risk for developing oxalate-related disorders by reducing the amount of oxalate in the intestinal tract. This reduction in the intestinal tract leads to a reduction in systemic oxalate levels thereby promoting good health.

To treat or prevent an oxalate-related condition, a therapeutically effective amount of the oxalate degrading polypeptide, an oxalate degrading a microorganism comprising the oxalate-reducing polypeptide, a cell having lysate from an oxalate degrading polypeptide is administered. By "therapeutically effective amount" is meant the concentration of an oxalate degrading microbe and/or polypeptide of the invention that is sufficient to elicit a therapeutic effect. Thus, the concentration of an oxalate degrading microbe and/or polypeptide of the invention in an administered dose unit is effective in the treatment or prevention of an oxalate-related disorder. The therapeutically effective amount will depend on many factors including, for example, the severity of the oxalate-related disorder, the responsiveness of the patient, the weight of the patient, along with other intrapersonal variability, the method of administration, and the oxalate degrading microbe and/or polypeptide formulation used. The oxalate degrading compositions are therefore administered at intervals determined by the needs of the individual. A single, periodic, or regular administration may be needed. Methods also include administering such compositions more than one time per day, more than two times per day, more than three times per day and in a range from 1 to 15 times per day. Such administrations may be continuously, as in every day for a period of days, weeks, months or years, or may occur at specific times to treat or prevent oxalate-related conditions.

The compositions of the present invention comprise pharmaceutically acceptable formulations. For example, the methods and compositions of the present invention comprise a dose delivery system that provides the compositions (i.e., the oxalate degrading enzymes or the oxalate degrading microbe) to the desired locations, such as delivery of the compositions to the intestines/mucosal regions of the subject. Pharmaceutical compositions include oxalate degrading bacteria or one or more oxalate degrading polypeptides, alone or in combinations include bacteria or polypeptides that have been lyophilized or frozen in liquid or paste form and encapsulated in a gel capsule, microcapsules, or other enteric protection. An enteric protective coating can be used to protect the composition from adverse effects of stomach acid. Such enteric coatings include the use of cellulose acetate phthalate (CAP). Additional descriptions of encapsulation technology include U.S. Pat. No. 5,286,495, which is incorporated herein by reference. The released composition then converts oxalate present in the intestine to harmless products. Carriers also can be combined with the bacteria or polypeptides. These would include, for example, saline-phosphate buffer.

In other embodiments, different food products can be supplemented with the oxalate degrading compositions of the invention. Such food products can subsequently be administered to the subject. Various methods can be employed for making such foods products including, for example, admixing a food material with an oxalate reducing composition of the invention. For example, yogurt cultures, the end yogurt food product, milk, cheese, or meat products can be mixed with the oxalate degrading microbes of the invention. In addition, plants expressing the oxalate reducing enzymes of the invention can be generated using known transformation technologies. Upon ingestion, when the food products are being digested and absorbed by the intestines, the oxalate degrading compositions, including one or more microbes, one or more polypeptides or combinations thereof, degrade oxalate present in the intestines thus reducing absorption of oxalate into the bloodstream.

It is recognized that the oxalate degrading sequences of the invention can be employed in combination with other sequences known to modulated oxalate degradation. Various oxalate degrading enzymes and the genes encoding these enzymes are known and include, for example, those set forth in U.S. Pat. Nos. 5,912,125; 6,090,628; and 6,214,980. These patents are incorporated herein by reference in their entirety. The term oxalate degrading enzyme includes but is not limited to oxalate oxidase, oxalate decarboxylase, oxalyl-CoA decarboxylase, and formyl-CoA transferase, and includes enzymes that are capable of interacting with oxalate or oxalic acid. These enzymes may be derived from natural sources or synthesized using recombinant means known in the art, and include all fragments, such as binding sites, active sites, or fragments capable of interacting with oxalate or oxalic acid. This term also includes but is not limited to all necessary cofactors, coenzymes, metals, or binding or substrate materials that are needed by the enzyme in interacting with oxalate or oxalic acid. The present invention also contemplates any binding partners of these enzymes and includes antibodies and antibody fragments that bind to or interact with the enzymes.

Additional Methods of Use

Methods are provided wherein properties of microbes used in fermentation are modified to provide strains which permit more efficient and/or more economic bioprocesses, or strains better able to survive, grow and/or colonize or inhabit the gastrointestinal tract of a host animal to which the strain is administered as a probiotic bacterium.

In one embodiment, expression or overexpression of a polynucleotide or polypeptide of the invention can modulate the growth rate of a bacterium. By "growth rate" is meant a measure of the rate of growth of an organism or culture. When the microorganism is grown in continuous liquid culture at an exponential growth rate, the increase in cell mass can be expressed in terms of the specific growth rate constant ($\mu$): $dP/dt=\mu \times P$, where P is the cell mass and t is the time. By "overexpressing" is meant that the protein of interest is produced in an increased amount in the modified bacterium compared to its production in a wild-type bacterium. Assays to measure the growth rate of bacteria are known in the art (see, for example, Bruinenberg et al. (1992) *Appl. Environ. Microbiol.* 58:78-84).

Methods for increasing oxalate degradation in a subject are provided, comprising introducing a lipase or esterase protein in a subject. In one embodiment, the protein is expressed in an organism that is used to ferment a dairy product, and the subject ingests the product. In another embodiment, the polypeptide itself is added to a food product. Expression of oxalyl CoA decarboxylase in the intestinal tract of a subject may help lower concentrations of oxalate in the blood or urine (see, for example, Troxel et al. (2003) *J. Endourol.* 17:173-176; Lung et al. (1991) *Am. J. Kidney Dis.* 17:381-385; Sidhu et al. (1999) *J. Am. Soc. Nephrol.* Suppl 14:S334-S340).

TABLE 1

Nucleic acids and proteins of the present invention

| ORF# | SEQ ID NO | Gene |
|---|---|---|
| 395 | 1 | Dehydratase |
| 396 | 3 | Oxalyl CoA decarboxlase |
| 38 | 5 | |
| 39 | 7 | |
| 40 | 9 | |
| 144 | 11 | |
| 149 | 13 | |
| 600 | 31 | Xylulose-5-phosphate/fructose phosphoketolase |
| 877 | 33 | Cellobiose phosphotransferase enzyme IIA |
| 1119 | 15 | Inner membrane protein |
| 1234 | 17 | Cadmium/manganese transport ATPase or $H^+$-transporting ATPase |
| 1339 | 19 | |
| 1462 | 21 | β-galactosidase |
| 1690 | 23 | Membrane protein |
| 1869 | 25 | |
| 1870 | 35 | Maltose phosphorylase |
| 1877 | 27 | |
| 1948 | 29 | |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

The following examples are offered by way of illustration and not by way of limitation.

EXPERIMENTAL

Example 1

Analysis of the Chromosomal Region Containing frc and oxc

Oxalic acid can be found in dietary sources (such as coffee, tea, chocolate) or produced from some metabolic precursors (such as ascorbic acid) by the intestinal microflora or by non enzymatic degradation. In the human intestine it may combine with calcium, sodium, magnesium, or potassium to form less soluble salts causing pathological disorders (hyperoxaluria, pyridoxine deficiency, urolithiasis and renal failure in humans). An operon containing genes homologous to a formyl coenzyme A transferase (frc) and oxalyl coenzyme A decarboxylase (oxc) was identified in the genome of the probiotic bacteria *Lactobacillus acidophilus*. These genes, not previously described in lactobacilli, are putatively responsible for oxalate degradation in this organism. Transcriptional analysis using cDNA microarrays and reverse-transcription quantitative PCR revealed that mildly acidic conditions were a prerequisite for frc and oxc transcription. As a consequence, oxalate-dependent induction of those genes *L. acidophilus* was only accomplished in cells exposed to pH 5.5 previously adapted to sub inhibitory concentrations of oxalate. Physiological analysis using a mutant harboring a deleted version of the frc gene (frc⁻) confirmed that frc expression specifically affects the survival under oxalic acid at pH 3.5 as compared with the wild type strain. A whole genome microarray containing 97.5% of the genes of *Lactobacillus acidophilus* NCFM was used to identify a candidate gene for the incorporation of the dissociated oxalate into the cell. Where genome information was available, other members of the lactic acid bacteria were screened for frc and oxc genes. With the exception of *Lactobacillus gasseri* NCK334 and *Bifidobacterium animalis*, none of the other strains harbored genes for oxalate utilization.

The genome sequence of *L. acidophilus* NCFM (Altermann et al. (2005) *Proc. Natl. Acad. Sci. U.S.A.* 102: 3906-3912) revealed the presence of an operon putatively involved in oxalate catabolism (FIG. 1). The predicted operon consisted of two genes: the formyl-CoA transferase (LBA0395, frc) and oxalyl-CoA decarboxylase (LBA0396, oxc), encoded on the complementary chain (FIG. 1). High-energy rho-independent terminators can be predicted downstream LBA0397 (Δ −11.4 Kcal/mol) and LBA0395 (Δ −14.6 Kcal/mol). Additionally, a typical RBS sequence (agaagg), 7 nt from the start, and a putative promoter were positioned upstream of oxc.

The gene downstream of frc (LBA0394) is also encoded on the complementary chain and its putative product is a protein of 395 amino acids (aa) which is virtually identical (90% identity, E value of 0.0) to a predicted acyl-CoA transferase/carnitin dehydratase from *Lactobacillus gasseri* NCK334 (Accession number ZP_00046082). It also shows 44% identity with a putative formyl-CoA transferase from *Escherichia coli* K12 (Accession number NP_416872) and 44% identity with a putative protein F (Accession number BAA 16242) of a bile acid-inducible operon from *E. coli*. A conserved domain (pfam02515) belonging to a new family of CoA-transferases is present in this protein. Most of CoA-transferases belong to two well-known enzyme families, but recently a third family of CoA-transferases was described (Heider (2001) *FEBS Lett.* 509: 345-349). Members of this enzyme family are oxalyl-CoA-transferase, succinyl-CoA:(R)-benzylsuccinate CoA-transferase, (E)-cinnamoyl-CoA:(R)-phenyllactate CoA-transferase, and butyrobetainyl-CoA:(R)-carnitine CoA-transferase.

LBA0395 encodes a protein of 445 aa length and shares an identity of 30% (48% similarity) with LBA0394. Additionally, LBA0395 is highly similar to the predicted acyl-CoA transferase from *L. gasseri* and the formyl-CoA transferase from *E. coli* K12. However, contrary to LBA0394, LBA0395 also showed a 44% identity (61% similarity) with the protein encoded by frc, the formyl-CoA transferase gene from *Oxalobacter formigenes* (Sidhu et al. (1997) *J. Bacteriol.* 179:3378-3381), which was the first member of the family III of Co-A transferases to be characterized.

LBA0396 encodes a 569-aa protein similar to the oxalyl-CoA decarboxylase (EC 4.1.1.8) from *O. formigenes* (53% identical and 71% similar; Lung et al. (1994) *J. Bacteriol.* 176:2468-2472) and *Bifidobacterium lactis* (46% identical and 63% similar, Federici et al. (2004) *Appl. Environ. Microbiol.* 70:5066-5073). The protein encoded by LBA0396 exhibits a conserved domain present in thiamine pyrophosphate (TPP)-requiring enzymes (COG0028). This domain is also present in several enzymes including acetolactate synthase, pyruvate dehydrogenase (cytochrome), glyoxylate carboligase, and phosphonopyruvate decarboxylase. Additionally, in LBA0396 the N-terminal TPP-binding domain (pfam02776) starts at residue 7 aa and spans for 171 aa, and the central TPP domain (pfam00205) starts at residue 197 aa and spans for 154 aa.

LBA0397, upstream to oxc, encodes a 639-aa protein showing the conserved domain COG0488, Uup, that corresponds to ATPase components of ABC transporters with duplicated ATPase domains (Holland and light (1999) *J. Mol. Biol.* 293:381-399). A high degree of identity to equivalent proteins (over 75%) encoded by *L. gasseri* and *L. johnsonii* was observed.

Other lactic acid bacteria were screened for frc and oxc related genes. With the exception of *Lactobacillus gasseri* NCK334 (Accession number ZP_0004699.1) and *Bifidobacterium animalis* (Accession number AB163432.1), none of the other strains harbored genes for oxalate utilization, including *Lactobacillus plantarum* WCFS1 (Kleerbezem et al. (2003) *Proc. Natl. Acad. Sci. U.S.A.* 100:1990-1995) and *Lactobacillus johnsonii*, a reputed probiotic culture (Pridmore et al. (2004) *Proc. Natl. Acad. Sci. U.S.A.* 101:2512-2517).

Example 2

Transcriptional Analysis of the oxc Operon Using Microarrays

Antiport of oxalate/formate in *O. formigenes* is coupled to oxalate decarboxylation and generates a proton-motive gradient (Abe et al. (1996) *J. Biol. Chem.* 271:6789-6793). In view of the fact that we were not able to identify a putative oxalate permease/antiporter by in silico analysis of *L. acidophilus* genome, we conducted microarray experiments in an attempt to identify a candidate that might be responsible for the specific transport of oxalate into the cell.

During growth of *L. acidophilus* in glucose-supplemented MRS medium, the pH of a culture starting at 6.5 typically decreases due to fermentation and lactic acid production. NCFM can comfortably tolerate mildly acidic conditions (pH≈5.5). A whole-genome array (WGA) containing 97.4% of NCFM annotated genes was used to identify genes that are differentially expressed under mildly acidic conditions (GEO accession numbers GPL1401 [platform] and GSE1976 [series]; 4). After exposure to pH 5.5 for 30 min, we observed the consistent induction of ORFs LBA0395 (3.2-fold) and LBA0396 (4.5 fold) encoding a putative formyl-CoA transferase (frc) and oxalyl-CoA decarboxylase (oxc), respectively (FIG. 2). In this study, the WGA of *L. acidophilus* was used to analyze the global gene expression after cells were exposed to 70 mM ammonium oxalate for 30 min at pH 6.8. Sixteen genes were significantly up regulated (P≦0.05 and a fold change>2.0, Table 2) and 315 genes were down regulated (P≦0.05 and a fold change<0.5). Both the frc or oxc genes were down regulated under this condition. The most up regulated genes were a cadmium/manganese transport ATPase (LBA1234) and two uncharacterized membrane proteins (LBA1119 and LBA1690). ORFs LBA0038, LBA0039, LBA0040, and LBA0041 were up regulated (between 1.43 and 2.45-fold). These four genes, encoded on the lagging strand, appear to form an operon. LBA0041 encodes a putative adenosylcobalamin (AdoCbl)-dependent ribonucleoside triphosphate reductase. ORFs LBA0038, LBA0039 and LBA0040 are poorly characterized, however LBA0040 is similar to a putative ATP:cob(I) alamin adenosyltransferase (Johnson et al. (2001) *J. Bacteriol* 183:1577-84, the enzyme responsible for the last step in the activation of vitamin B12 (cyanocobalamin, CNCbl) to coenzyme B12 (AdoCbl), the enzyme responsible for the last step in the activation of vitamin B12 (cyanocobalamin, CNCbl) to coenzyme B12 (AdoCbl). The reason why these genes are up regulated in the presence of ammonium oxalate requires further investigation.

TABLE 2

Differentially expressed genes in *Lactobacillus. acidophilus* NCFM in response to 1% ammonium oxalate at pH 6.8.

| Gene | Description | Expression Ratio | P-value |
| --- | --- | --- | --- |
| La38 | Hypothetical protein | 2.3779 | 3.05E−05 |
| La39 | Hypothetical protein | 2.45397 | 0.00715 |
| La40 | Hypothetical protein | 1.98763 | 0.01751 |
| La144 | N-acetylglucosamine-6-P deacetylase | 3.20624 | 0.000577 |
| La149 | Hypothetical protein | 2.35141 | 0.00148 |
| La600 | Xylulose-5-phosphate/fructose phosphoketolase | 3.07795 | 0.00465 |
| La877 | PTS system IIa | 2.11961 | 0.01174 |
| La1119 | Putative inner membrane protein | 5.9474 | 1.53E−05 |
| La1234 | Cadmium/manganese transport ATPase | 9.64192 | 0.000479 |
| La1339 | Hypothetical protein | 2.33961 | 0.01897 |
| La1462 | Beta-galactosidase | 1.98621 | 3.70E−02 |
| La1690 | Putative membrane protein | 4.76365 | 0.00306 |
| La1869 | Beta-phosphoglucomutase | 2.9235 | 5.99E−05 |
| La1870 | Maltose phosphorylase | 3.13107 | 0.00337 |
| La1877 | Hypothetical protein | 2.59773 | 0.00538 |
| La1948 | Glucosamine-6-phosphate isomerase | 2.3297 | 0.01976 |

Example 3

Transcriptional Analysis of the oxc Operon by RTQ-PCR

Acid-induction of frc and oxc was evaluated in the presence and absence of ammonium oxalate as inducer of the expression of the operon. Primers meeting RTQ-PCR criteria were designed for genes LBA0394, LBA0395 (frc), LBA0396 (oxc), and LBA0397. Additionally, since LBA0394 showed some homology to a bile-inducible protein (see above) we also designed RTQ-PCR primers for two ORFs in the NCFM genome encoding bile salt hydrolases LBA0872 (bsh1) and LBA1078 (bsh2).

Figure 3:
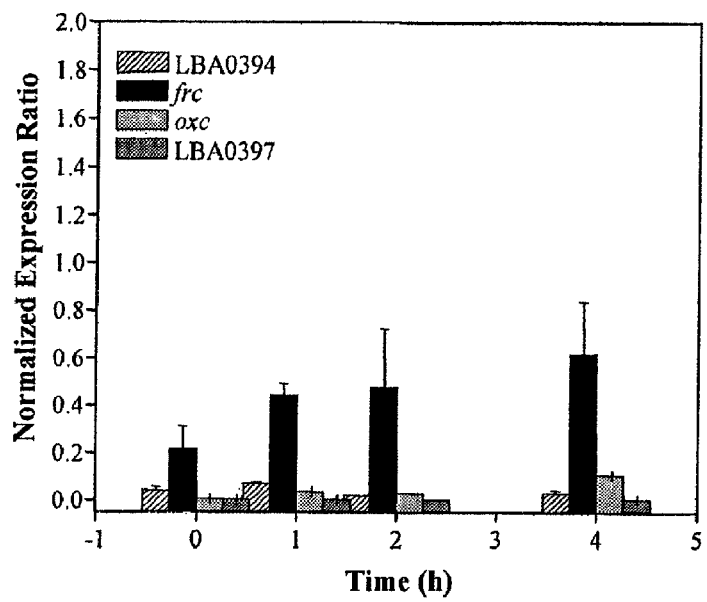
FIG. 3A shows the transcriptional analysis of the oxc operon in *L. acidophilus* cells at pH 5.5. Cells were first transferred in MRS broth pH 6.8 (non-adapted). Gene induction was followed over time after cells were placed in MRS broth, pH 5.5. ORF numbers in NCFM are denoted.
FIG. 3B shows the transcriptional analysis of the oxc operon in *L. acidophilus* cells at pH 5.5. Cells were first transferred in MRS broth pH 6.8 containing non-inhibitory concentrations of ammonium oxalate (pre-adapted). Gene induction was followed over time after cells were placed in MRS broth, pH 5.5. ORF numbers in NCFM are denoted.
Figure 3:
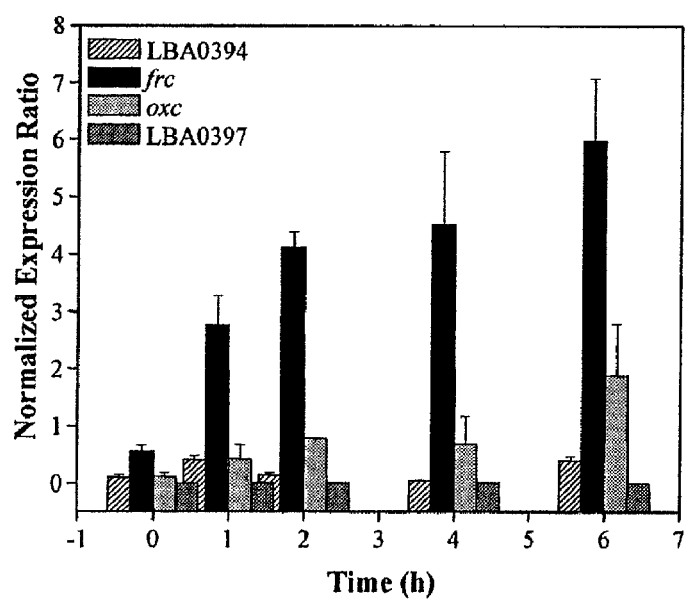

*L. acidophilus* was adapted to oxalate by three consecutive transfers in MRS broth containing 0.05% ammonium oxalate, a non-inhibiting concentration. Cells pre-exposed or not-exposed to this compound were then transferred to MRS broth at pH 5.5 (adjusted with lactic acid), and samples were taken over time. ORFs LBA0397, bsh1 and bsh2 (not shown) were not expressed under any of the conditions assayed. Expression of LBA0394 was basal and constant. In contrast, the frc and oxc genes were highly expressed in cells exposed to pH 5.5 (FIG. 3A). When *L. acidophilus* cells were propagated in the presence of ammonium oxalate and then exposed to pH 5.5 plus 0.5% ammonium oxalate, frc and oxc expression increased dramatically (FIG. 3B). Subsequently, cells were pre-exposed to oxalate or not, and then resuspended in MRS containing 0.5% ammonium oxalate (pH>6.0). However, at the higher pH, no induction of any of the genes studied was observed (data not shown).

Example 4

Inactivation of frc and Mutant Phenotype Analysis

The integrative plasmid pOR128, a pWV01-derived vector (Law et al. (1995) *J. Bacteriol.* 177:7011-7018) was used to replace frc with the deleted version of the same gene. A 1.42-kb fragment containing frc was amplified using *L. acidophilus* NCFM chromosomal DNA as template and cloned in pOR128. Subsequently, a 72-bp fragment of the cloned gene was removed by inverted PCR amplification and posterior self-ligation. The resulting 3.04-kb plasmid pTRK837 was then introduced by electroporation in *L. acidophilus* NCFM containing the helper plasmid pTRK669. Subsequent steps to facilitate the integration event and gene replacement were carried out according to the protocols previously described (Russell and Klaenhammer (2001) *Appl. Environ. Microbiol.* 67:4361-4364 and Bruno-Barcena et al. (2005) *FEMS Microbiol. Lett.* 246:91-101). PCR and Southern hybridization experiments using an internal fragment of frc as probe confirmed the occurrence of the gene replacement.

The survival of log cells ($OD_{600}$=0.3) of the wild-type (*L. acidophilus* NCFM; wt) and frc$^-$ strains at pH 4.0, 3.5 and 3.0 was compared, using hydrochloric acid (HCl), lactic acid and oxalic acid to acidify MRS broth. No differences were observed between the wt and the mutant when HCl or lactic acid was used to acidify the culture medium. Additionally, no differences were observed between strains, in the presence of 5% oxalic acid, at pH 4.0 (>50% survival) or 3.0 (<0.01% survival). However, frc$^-$ was more sensitive to 5% (w/v) oxalic acid after 2 h at pH 3.5 (FIG. 4).

Figure 4:
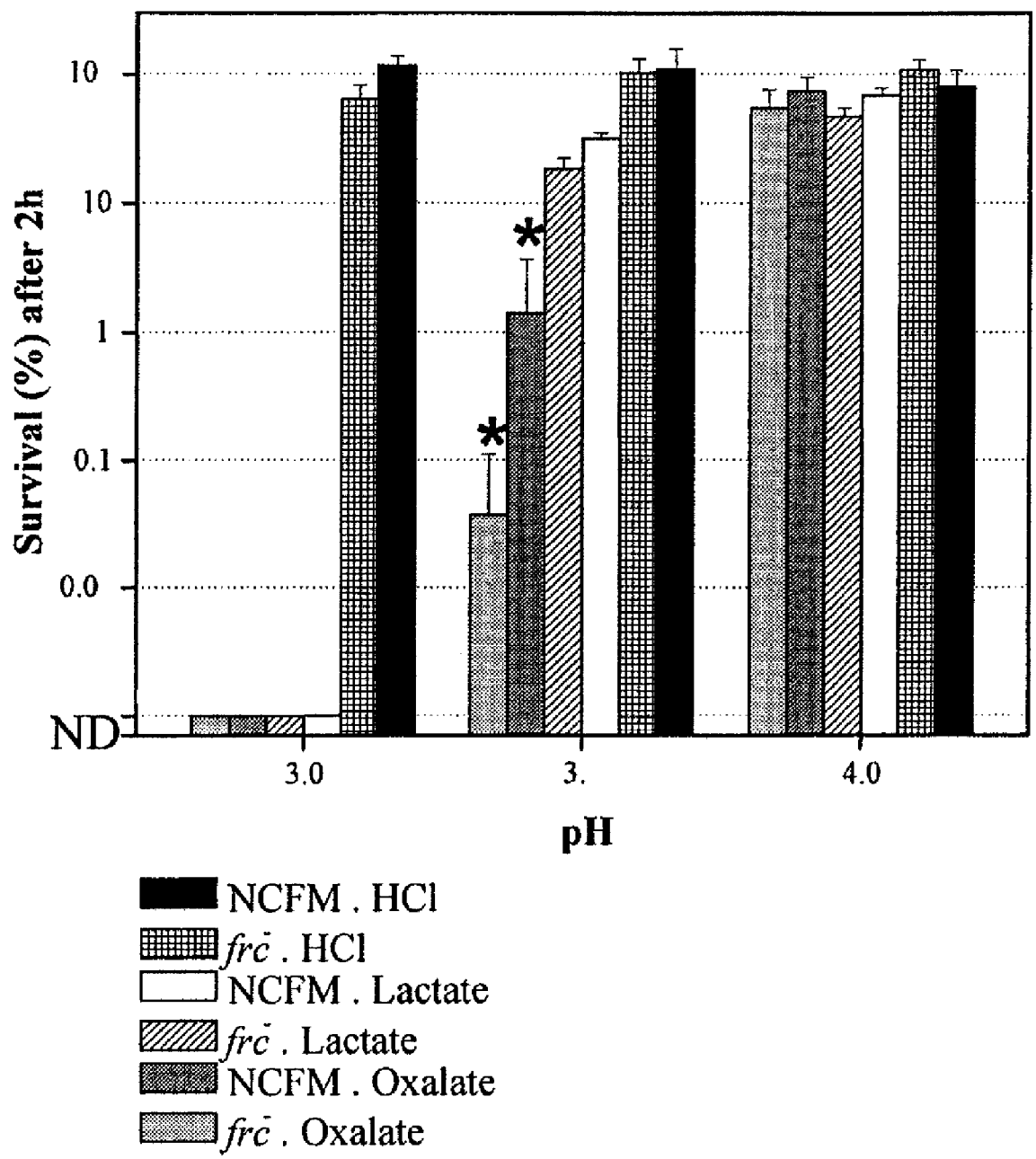
FIG. 4 shows survival of log-phase cells of *L. acidophilus* NCFM and the frc⁻ mutant after challenge with HCl, lactic acid or oxalic acid for 2 hours in MRS broth adjusted to pH 4.0, 3.5, and 3.0.
Figure 5:
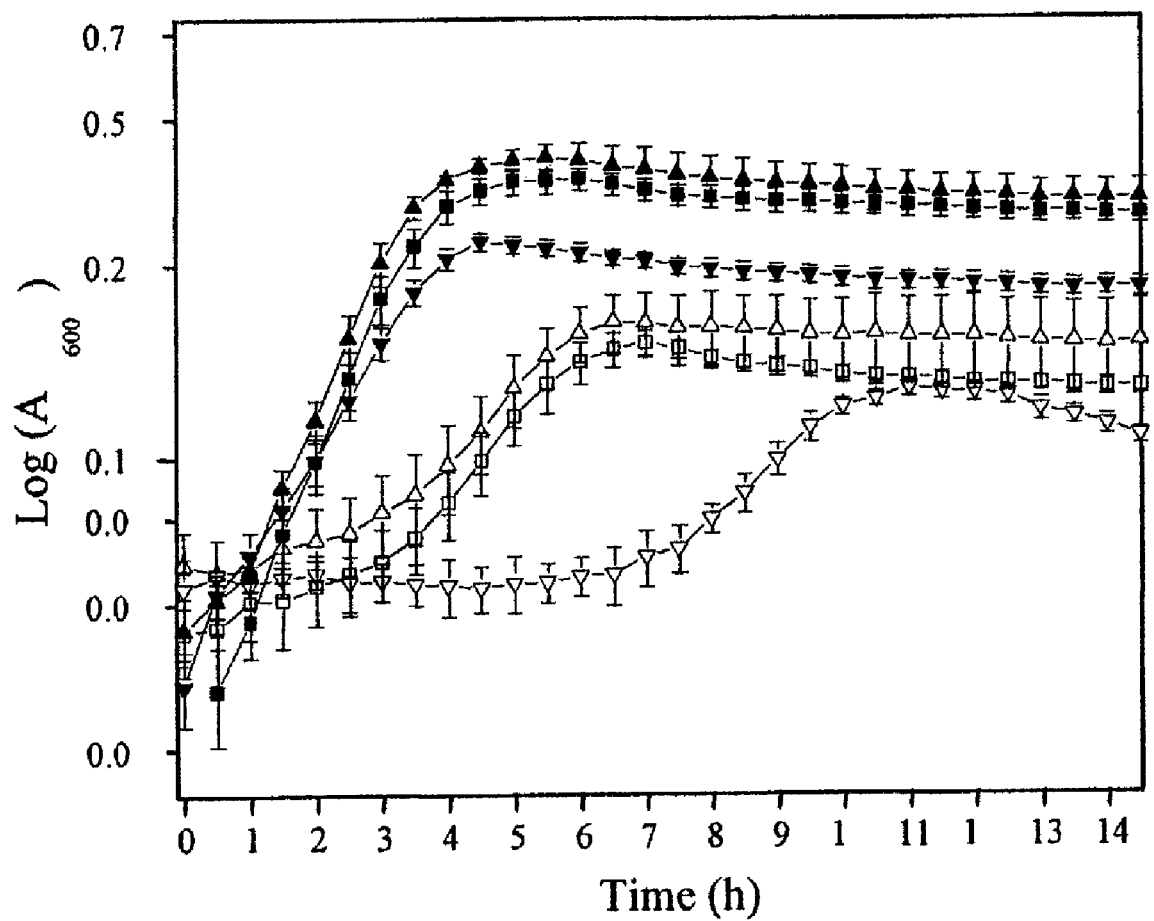
FIG. 5 shows growth curves of *L. acidophillus* NCFM in semi-defined BM media containing different concentrations of ammonium oxalate. Growth was evaluated in BM in the presence of 0.1% glucose (■) and glucose plus 0.1% (▲) or 0.5% (▼) ammonium oxalate, or in the absence of glucose (□) or in the absence of glucose plus 0.1% (Δ) or 0.5% (∇) ammonium oxalate.

The ability of the control and the mutant strains to tolerate and/or grow in the presence of oxalate in a semi-defined medium (BM) since the addition of the salt caused precipitation of MRS broth was examined (FIG. 4). The growth rate in BM was similar for both *L. acidophilus* strains (0.7 h$^{-1}$ in BM containing 0.1% glucose). No differences were observed between strains when 0.1% or 0.5% ammonium oxalate ($C_2H_8N_2O_4$) was added to the cultures in the presence of glucose, since growth rates decreased in both strains in the presence of 0.5% $C_2H_8N_2O_4$ (0.48 h$^{-1}$ for the control and 0.52 h$^{-1}$ for the mutant). Interestingly, a lag-phase of 7 hours was observed when 0.5% $C_2H_8N_2O_4$ was added to the media without glucose indicating that strains require detoxifying this compound to grow.

Finally, oxalate content was measured in both NCFM and the frc mutant (FIG. 6). *Lactobacillus* strains were consecutively transferred for 3 days in BM broth without citrate (BM$^{cit-}$), containing 1% glucose plus 3.5 mM ammonium oxalate. After 3 days, 100 µl of cells were inoculated in the same medium and grown to an $A_{600}$ of 0.6, centrifuged and resuspended in BM$^{cit-}$ containing 0.1% glucose plus 35 mM ammonium oxalate (32 mM oxalate). Samples were taken over time, centrifuged, neutralized to a pH between 5 and 7 (according to the manufacturer's instructions) with 1N sodium hydroxide and stored at −20° C. Oxalate concentration in the supernatants was measured in triplicate using the diagnostic oxalate kit (Trinity Biotech, Co Wicklow, Ireland) based on the oxidation of oxalate by oxalate oxidase.

Figure 6:
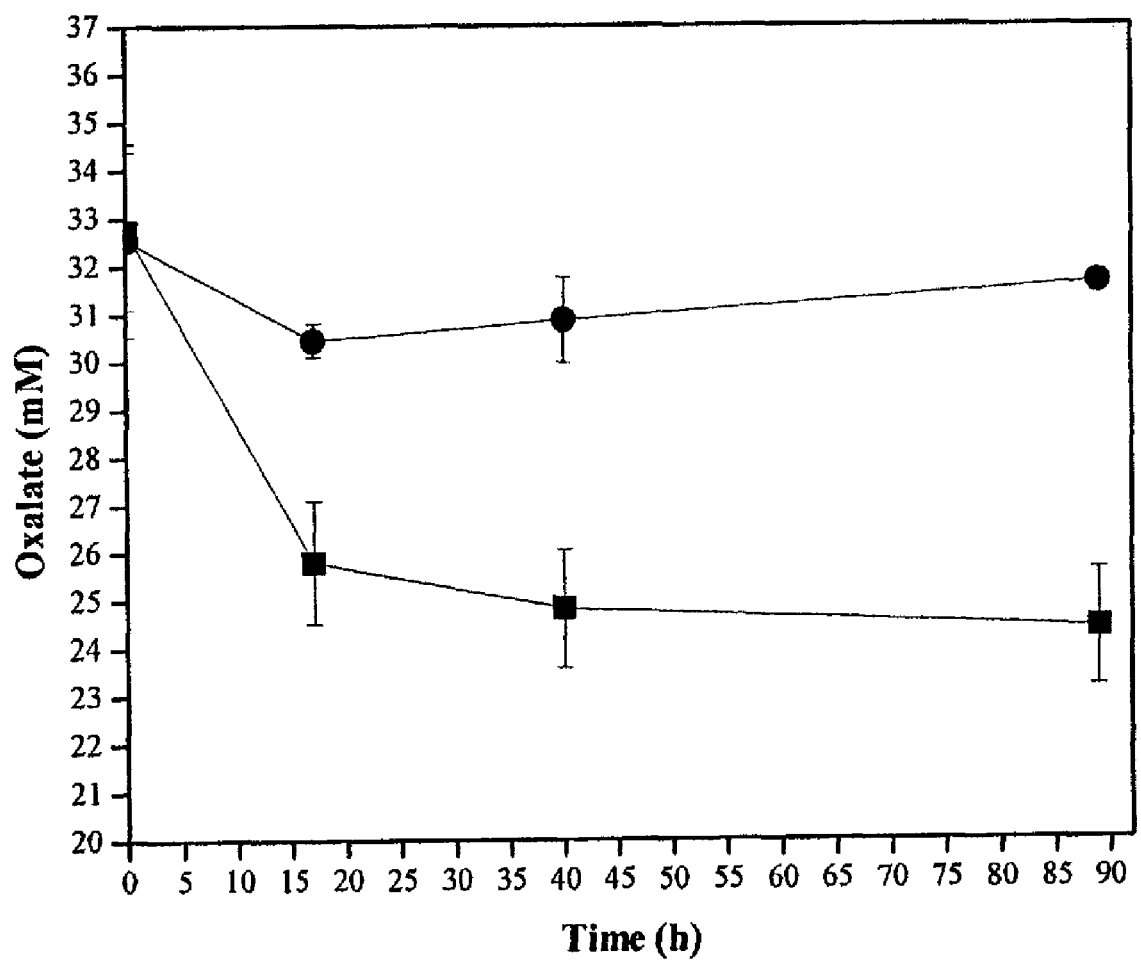
FIG. 6 shows oxalate-degrading activity of *Lactobacillus acidophilus*. Strains NCFM (■) and frc⁻ (●) were consecutively transferred in broth containing a non-inhibitory concentration of oxalate (3.5 mM), and then transferred to broth containing 32 mM oxalate. Samples were taken over time and oxalate concentration in the supernatants was measured.

As shown in FIG. 6, the content of oxalate in the culture supernatant decreased significantly in the control (up to 23.6%) but not in the mutant strain where oxalate content decreased 5.8%. Most of the oxalate degradation occurred during the first 16 hours of culture growth. The results indicated that *L. acidophilus* was able to degrade oxalate, and Frc participates in this process.

Example 5

Summary of Transcriptional and Functional Analysis of Oxalyl-CoA Decarboxylase and Formyl-CoA Transferase from *Lactobacillus acidophilus*

Studies using a whole-genome microarray of *Lactobacillus acidophilus* NCFM (Azcarate-Peril et al. *Appl. Environ. Microbiol.* (in press)) showed the consistent induction of ORFs LBA0395 and LBA0396 at mildly acidic pH. A comparative analysis of these and the adjacent genes with the available sequences at the Genbank, identified a formyl-CoA transferase (frc) and oxalyl-CoA decarboxylase (oxc), highly similar to frc and oxc from *Oxalobacter formigenes*. In *L. acidophilus*, frc and oxc appear to form an operon and are encoded on the complementary strand. RTQ-PCR and microarray experiments confirmed that oxalate (pH>5.8) did not directly induce the expression of frc and oxc, which were induced under acidic conditions. However, when *L. acidophilus* was repeatedly transferred in broth containing non-inhibitory concentrations of ammonium oxalate and subsequently exposed to pH 5.5, the expression of those genes, especially frc, was dramatically increased. Moreover, when frc was inactivated and the mutant strain was exposed to acidic pH it proved to be more susceptible specifically to oxalic acid at pH 3.5, indicating that frc is involved in the detoxification of oxalate by *L. acidophilus*. Additionally, the frc$^-$ mutant was unable to degrade oxalate and was significantly below the wild-type strain, which exhibited an oxalate-degrading activity of 23.56%.

The concept of autochthonous microorganisms of the gastrointestinal tract has been discussed by several authors (for a review see 33). In fact, Tannock proposed a concise definition based on three important characteristics: a long-term association with the host, a stable population in a particular region of the gut, and a demonstrated ecological function. Oxalate occurs widely in nature and oxalate-rich foods are important sources of oxalate in the diet. The presence of bacteria that specifically degrade oxalate may regulate the oxalate homeostasis of the host by preventing absorption, catabolizing free oxalate and enhancing oxalate removal from the circulation. Consequently, the capability to detoxify this compound potentially suggests a new ecological function for *L. acidophilus*.

Other oxalate-degrading bacteria isolated from the human gastro intestinal tract include *Eubacterium lentum* (Ito et al. (1996) *Int. J. Urol.* 3:31-34) and *Enterococcus faecalis* (Hokama et al. (2000) *Microbiol. Immunol.* 44:235-240). The authors isolated an oxalate-degrading *E. faecalis* from human stools under anaerobic conditions, and they identified the formyl-CoA transferase and oxalyl-CoA decarboxylase enzymes by Western blottings using antibodies against Frc and Oxc from *O. formigenes*. Campieri et al. (Campieri et al. (2001) *Kidney Internat.* 60:1097-1105) measured oxalate degradation in patients with idiopatic calcium-oxalate urolithiasis treated with 8×10$^{11}$ LAB (including *L. acidophilus, L. plantarum, L. brevis, Streptococcus thermophilus*, and *Bifidobacterium infantis*). They observed a reduction in the excreted oxalate, and in vitro reduction, especially by *L. acidophilus* and *S. thermophilus* (even when their growth was partially inhibited by this compound). However, the genes responsible for oxalate degradation by these microorganisms were not identified. More recently, the oxalyl-CoA decarboxylase gene was identified in *B. lactis*, and oxalate-degrading activity of the enzyme was confirmed by a capillary eletrophoresis-based method (Federici et al. (2004) *Appl. Environ. Microbiol.* 70: 5066-5073). Therefore, oxalate catabolism in the grastrointestinal tract may be an important property of some comensal and probiotic bacteria.

In other oxalate-degrading organisms as *O. formigenes*, the utilization of oxalate is coupled to energy production, produced by the antiport of oxalate and formate. We were not able to identify a putative permease/antiporter that incorporates dissociated oxalate into the cell by in silico analysis. It is commonly known that the non-dissociated forms of organic acids, such as oxalic acid can freely diffuse through the cytoplasmic membrane. This might explain the apparent absence of a specific transporter for oxalic acid in the genome of NCFM. The concentration of oxalate entering the cell will increase under acidic conditions, which may also occur during the passage of the cells through the variable pH conditions of the gastrointestinal tract. As an alternative hypothesis, one of the three genes encoding membrane proteins may participate in the active transport of this compound into the cell, particularly as they were strongly up regulated in the presence of ammonium oxalate. The first, a cadmium/manganese transport ATPase (LBA1234) was up regulated 9.64 fold. The predicted protein encoded by LBA1234 shows two conserved domains: pfam00122 (E1-E2 ATPase) and COG0474 (MgtA, cation transport ATPase). E1E2-ATPases are primary active transporters that form phospho-intermediates during their catalytic cycle. They are classified into P1 to P4 based on the primary structure and potential transmembrane segments (Axelsen and Palmgren (1998) *J Mol Evol.* 46:84-101). E1E2-ATPases transport divalent cations (as oxalate is) hence LBA1234 might be the transporter responsible for the translocation of oxalate into the cell. Two other uncharacterized membrane proteins (LBA1119 and LBA1690) were also up regulated, but they did not harbor any features for putative identification. Additionally, we did not observe over expression of LBA0397, the gene immediately downstream oxc, encoding the ATPase subunit of a putative ABC transporter, under any of the studied conditions.

The gene upstream LBA0394 is similar to a transcriptional regulator and the gene downstream LBA0397 is a putative AT-rich DNA binding protein. These observations, combined with expression data suggest that the oxc operon in *L. acidophilus* is regulated. Moreover, we can speculate that the ability to decarboxylate oxalyl-CoA was acquired by *L. acidophilus* by horizontal gene transfer. The operon is encoded on the complementary strand and the GC content of frc (38.4%) and oxc (40.2%) is notably higher than the average for the NCFM genome (34.71%).

The efficacy of probiotics as means to prevent and/or treat urogenital infections and recurrent bladder cancer has been scientifically accepted in the past two decades (Hoesl and Altwein (2005) *Eur. Urol.* 47: 288-296). More recently, encouraging results were obtained in a clinical trial of *O fomigenes* for patients suffering from hyperoxaluria Type I (an inherited, life-threatening disease characterized by recurrent oxalate stone formation, nephrocalcinosis and eventual liver and kidney failure). Additional clinical studies and the delivery of probiotic bacteria capable of oxalate detoxification may lead to a complementary method to prevent renal stone formation and reduce the incidence of other pathological disorders (like pyridoxine deficiency, urolithiasis, and renal failure) enhancing acceptance of probiotics by physicians and consumers.

Example 6

Sequence Characterization

SEQ ID NO: 14 shares homology to PFAM family PF00582. PF00582 comprises a family of universal stress proteins. A representative member of this family is UspA USPA_ECOLI (Sousa et al. (2001) *Structure* 9:1135-1141) which is a small cytoplasmic bacterial protein whose expression is enhanced when the cell is exposed to stress agents. UspA enhances the rate of cell survival during prolonged exposure to such conditions, and may provide a general "stress endurance" activity. The crystal structure of *Haemophilus influenzae* UspA (Nystrom et al. (1994) *Mol Microbiol* 11:537-544) reveals an alpha/beta fold similar to that of the *Methanococcus jannaschii* MJ0577 protein, which binds ATP Zarembinski et al. (1998) *Proc Natl Acad Sci USA* 95:15189-15193, though UspA lacks ATP-binding activity.

SEQ ID NO: 6 shares homology to PFAM family PF01923. PF01923 comprises a family of proteins that share homology to cobalamin adenosyltransferase. This family contains the gene products of PduO and EutT which are both cobalamin adenosyltransferases. PduO is a protein with ATP:cob(I) alamin adenosyltransferase activity. The main role of this protein is the conversion of inactive cobalamins to AdoCbl for 1,2-propanediol degradation (Kofoid et al. (1999) *J Bacteriol* 181:5317-5329). The EutT enzyme appears to be an adenosyl transferase, converting CNB12 to AdoB12 (Johnson (2001) *J Bacteriol* 183:1577-1584).

SEQ ID NO: 18 shares homology to PFAM family PF00122. PF00122 comprises a family of proteins having homology to p-type (or E1-E2-type) aTPases which constitute a superfamily of cation transport enzymes, present both in prokaryotes and eukaryotes, whose members mediate membrane flux of all common biologically relevant cations. The enzymes, that form an aspartyl phosphate intermediate in the course of ATP hydrolysis, can be divided into 4 major groups: (1) $Ca^{2+}$-transporting ATPases; (2) $Na^+/K^+$- and gastric $H^+/K^+$-transporting ATPases; (3) plasma membrane $H^+$-transporting ATPases (proton pumps) of plants, fungi and lower eukaryotes; and (4) all bacterial P-type ATPases, except the $Mg^{2+}$-ATPase of *Salmonella typhimurium*, which is more similar to the eukaryotic sequences. However, great variety of sequence analysis methods results in diversity of classification.

SEQ ID NO:22 shares homology to PFAM family PF02449. PF02449 comprises a family of proteins having homology to Beta-galactosidase. This group of beta-galactosidase enzymes belong to the glycosyl hydrolase 42 family. The enzyme catalyses the hydrolysis of terminal, non-reducing terminal beta-D-galactosidase residues.

SEQ ID NOS: 26 and 18 share homology to PFAM family PF00702. PF00702 comprises a family of proteins having a haloacid dehalogenase-like hydrolase domain. This family are structurally different from the alpha/beta hydrolase family (Abhydrolase_1). This family includes L-2-haloacid dehalogenase, epoxide hydrolases and phosphatases. The structure of the family consists of two domains. One is an inserted four helix bundle, which is the least well conserved region of the alignment, between residues 16 and 96 of HAD1_PSEUC. The rest of the fold is composed of the core alpha/beta domain.

SEQ ID NO: 30 shares homology to PFAM family PF01182. PF01182 comprises a family of proteins having a Glucosamine-6-phosphate isomerases/6-phosphogluconolactonase domain. This entry contains 6-phosphogluconolactonase (EC:3.1.1.31), Glucosamine-6-phosphate isomerase (EC:3.5.99.6), and Galactosamine-6-phosphate isomerase. 6-phosphogluconolactonase is the enzyme responsible for the hydrolysis of 6-phosphogluconolactone to 6-phosphogluconate, the second step in the pentose phosphate pathway. Glucosamine-6-phosphate isomerase (or Glucosamine 6-phosphate deaminase) is the enzyme responsible for the conversion of D-glucosamine 6-phosphate into D-fructose 6-phosphate. It is the last specific step in the pathway for N-acetylglucosamine (GlcNAC) utilization in bacteria such as *Escherichia coli* (gene nagB) or in fungi such as *Candida albicans* (gene NAG1). A region located in the central part of Glucosamine-6-phosphate isomerase contains a conserved histidine which has been shown, in nagB, to be important for the pyranose ring-opening step of the catalytic mechanism.

SEQ ID NO: 34 shares homology to PFAM family PF02302. PF02302 comprises a family of proteins having a PTS system, Lactose/Cellobiose specific IIB subunit. The bacterial phosphoenolpyruvate: sugar phosphotransferase system (PTS) is a multi-protein system involved in the regulation of a variety of metabolic and transcriptional processes. The lactose/cellobiose-specific family is one of four structurally and functionally distinct group IIB PTS system cytoplasmic enzymes. The fold of IIB cellobiose shows similar structure to mammalian tyrosine phosphatases.

SEQ ID NO: 36 shares homology to PFAM family PF03632. PF03632 comprises a family of proteins having a glycosyl hydrolase family 65 central catalytic domain. This family of glycosyl hydrolases contains vacuolar acid trehalase and maltose phosphorylase. Maltose phosphorylase (MP) is a dimeric enzyme that catalyses the conversion of maltose and inorganic phosphate into beta-D-glucose-1-phosphate and glucose. The central domain is the catalytic domain, which binds a phosphate ion that is proximal the highly conserved Glu. The arrangement of the phosphate and the glutamate is thought to cause nucleophilic attack on the anomeric carbon atom Egloff et al. (2001) *Structure* (Camb) 9:689-697). The catalytic domain also forms the majority of the dimerisation interface.

SEQ ID NO: 36 shares homology to PFAM family PF03636. PF03636 comprises a family of proteins having a glycosyl hydrolase family 65, N-terminal domain. This family of glycosyl hydrolases contains vacuolar acid trehalase and maltose phosphorylase. Maltose phosphorylase (MP) is a dimeric enzyme that catalyses the conversion of maltose and inorganic phosphate into beta-D-glucose-1-phosphate and glucose. This domain is believed to be essential for catalytic activity (Egloff et al. (2001) *Structure* (Camb) 9:689-697).

All publications, patents and patent applications mentioned in the specification are indicative of the level of those skilled in the art to which this invention pertains. All publications, patents and patent applications are herein incorporated by reference to the same extent as if each individual publication, patent, or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

TABLE 3

Top Blast result for each protein sequence

| SEQ ID NO: | ORF | Percent Identity | Amino Acid Range | Organism | Description | Accession No. |
|---|---|---|---|---|---|---|
| 2 | 395 | 84 | 4 to 442 | *Lactobacillus gasseri* | COG1804: Predicted acyl-CoA transferases/carnitine dehydratase | ref|ZP_00047386.1 |
| 4 | 396 | 71 | 1 to 569 | *Lactobacillus gasseri* | COG0028: Thiamine pyrophosphate-requiring enzymes (acetolactate synthase, pyruvate dehydrogenase (cytochrome), glyoxylate carboligase, phosphonopyruvate decarboxylase) | ref|ZP_00047384.1 |
| 6 | 38 | 68 | 1 to 178 | *Lactobacillus gasseri* | COG2096: Uncharacterized conserved protein | ref|ZP_00046768.1 |
| 8 | 39 | 65 | 1 to 169 | *Lactobacillus gasseri* | hypothetical protein | ref|NP_442412.1 |
| 10 | 40 | 58 | 1 to 85 | *Lactobacillus gasseri* | hypothetical protein | ref|ZP_00046754.1 |
| 12 | 144 | 69 | 1 to 384 | *Lactobacillus gasseri* | COG1820: N-acetylglucosamine-6-phosphate deacetylase | ref|ZP_00045970.1 |
| 14 | 149 | 81 | 1 to 151 | *Lactobacillus gasseri* | COG0589: Universal stress protein UspA and related | ref|ZP_00047032.1 |
| 16 | 1119 | 79 | 1 to 328 | *Lactobacillus gasseri* | COG2855: Predicted membrane protein | ref|ZP_00062705.1 |
| 18 | 1234 | 79 | 2 to 625 | *Lactobacillus gasseri* | COG0474: Cation transport ATPase | ref|XP_356827.1 |
| 20 | 1339 | 81 | 2 to 249 | *Lactobacillus gasseri* | COG1284: Uncharacterized conserved protein | ref|ZP_00047447.1 |
| 22 | 1462 | 47 | 2 to 665 | *Bacillus circulans* | Beta-D-galactosidase | ref|ZP_00046986.1 |
| 24 | 1690 | 25 | 44 to 279 | *Streptococcus pyogenes* | putative surface exclusion protein | ref|NP_830287.1 |
| 26 | 1869 | 86 | 1 to 220 | *Lactobacillus gasseri* | COG0637: Predicted phosphatase/phosphohexomutase | ref|ZP_00060522.1 |
| 28 | 1877 | 34 | 9 to 130 | *Lactobacillus gasseri* | COG1396: Predicted transcriptional regulators | ref|ZP_00045911.1 |
| 30 | 1948 | 68 | 1 to 238 | *Lactobacillus gasseri* | COG0363: 6-phosphogluconolactonase/Glucosamine-6-phosphate | ref|ZP_00046833.1 |
| 32 | 600 | 65 | 1 to 799 | *Lactobacillus pentosus* | phosphoketolase | emb|CAC84393.1 |
| 34 | 877 | 55 | 2 to 159 | *Lactobacillus gasseri* | COG0778: Nitroreductase | ref|ZP_00045913.1| |
| 36 | 1870 | 85 | 1 to 755 | *Lactobacillus johnsonii* NCC 533 | maltose phosphorylase | ref|NP_964229.1| |

TABLE 4

PFAM results for each protein sequence

| SEQ ID NO: | ORF | Domain | Amino Acid Range (Start, Stop) | Family | PFAM Accession No. | E-value |
|---|---|---|---|---|---|---|
| 2 | 395 | CoA_transf_3 | 76, 291 | CoA-transferase family III | PF02515 | 2.90E−69 |
| 4 | 396 | TPP_enzyme_M | 197, 351 | Thiamine pyrophosphate enzyme, central domain | PF00205 | 1.50E−47 |

TABLE 4-continued

PFAM results for each protein sequence

| SEQ ID NO: | ORF | Domain | Amino Acid Range (Start, Stop) | Family | PFAM Accession No. | E-value |
|---|---|---|---|---|---|---|
| 4 | 396 | TPP_enzyme_N | 7, 178 | Thiamine pyrophosphate enzyme, N-terminal TPP binding domain | PF02776 | 1.60E−45 |
| 6 | 38 | Cob_adeno_trans | 5, 168 | Cobalamin adenosyltransferase | PF01923 | 1.00E−46 |
| 14 | 149 | Usp | 3, 146 | Universal stress protein family | PF00582 | 6.90E−18 |
| 16 | 1119 | Cons_hypoth698 | 1, 309 | Conserved hypothetical protein 698 | PF03601 | 6.00E−62 |
| 18 | 1234 | E1-E2_ATPase | 66, 288 | E1-E2 ATPase | PF00122 | 1.00E−36 |
| 18 | 1234 | Hydrolase | 292, 536 | haloacid dehalogenase-like hydrolase | PF00702 | 1.00E−23 |
| 20 | 1339 | DUF161 | 105, 186 | Uncharacterized BCR, YitT family COG1284 | PF02588 | 4.20E−24 |
| 22 | 1462 | Glyco_hydro_42 | 192, 605 | Beta-galactosidase | PF02449 | 1.90E−150 |
| 26 | 1869 | Hydrolase | 2, 192 | haloacid dehalogenase-like hydrolase | PF00702 | 4.00E−29 |
| 30 | 1948 | Glucosamine_iso | 16, 236 | Glucosamine-6-phosphate isomerases/ 6-phosphogluconolactonase | PF01182 | 1.80E−45 |
| 34 | 877 | PTS_IIA | 16, 111 | PTS system, Lactose/Cellobiose specific IIB subunit | PF02302 | 8.70E−40 |
| 36 | 1870 | Glyco_hydro_65m | 320, 692 | Glycosyl hydrolase family 65 central catalytic domain | PF03632 | 4.30E−203 |
| 36 | 1870 | Glyco_hydro_65N | 11, 266 | Glycosyl hydrolase family 65, N-terminal domain | PF03636 | 2.00E−86 |

That which is claimed is:

1. An isolated nucleic acid molecule comprising a nucleotide sequence having at least 95% sequence identity to SEQ ID NO: 3, wherein said nucleic acid molecule encodes a polypeptide having oxalate degrading activity.

2. A plasmid comprising the nucleic acid molecule of claim 1.

3. A microbial cell comprising a heterologous nucleic acid molecule comprising a nucleotide sequence having at least 95% sequence identity to SEQ ID NO: 3, wherein said nucleic acid molecule encodes a polypeptide having oxalate degrading activity.

4. The microbial cell of claim 3, wherein said microbial cell is a bacterial cell.

5. The microbial cell of claim 4, wherein said bacterial cell is a probiotic bacterium.

6. The microbial cell of claim 4, wherein said bacterial cell is a lactic acid bacterium.

7. The microbial cell of claim 6, wherein said lactic acid bacterium is selected from the group consisting of *Lactobacillus acidophilus, L. gasseri, L. johnsonni*, and *L. plantarum*.

8. The microbial cell of claim 4 further comprising a second nucleic acid molecule having at least 95% sequence identity to SEQ ID NO:1, wherein said second nucleic acid molecule encodes a polypeptide having oxalate degrading activity.

9. The microbial cell of claim 8, wherein said second nucleic acid molecule is heterologous to said bacterial cell.

10. The microbial cell of claim 6 further comprising a second nucleic acid molecule having at least 95% sequence identity to SEQ ID NO:1, wherein said second nucleic acid molecule encodes a polypeptide having oxalate degrading activity.

11. The microbial cell of claim 10, wherein said second nucleic acid molecule is heterologous to said bacterial cell.

12. A bacterium comprising
(a) a first nucleic acid molecule comprising a nucleotide sequence having at least 95% sequence identity to SEQ ID NO:3, wherein said nucleotide sequence encodes a polypeptide having oxalate degrading activity; and,
(b) a second nucleic acid molecule comprising a nucleotide sequence having at least 95% sequence identity to SEQ ID NO:1, wherein said nucleotide sequence encodes a polypeptide having oxalate degrading activity; and,
where at least one of said first or said second nucleic acid molecule is heterologous to the bacterium and said first and said nucleic acid molecules are operably linked to a promoter active in said bacterium.

13. The bacterium of claim 12, wherein said bacterium is a probiotic bacterium.

14. The bacterium of claim 13, wherein said bacterium is a lactic acid bacterium.

15. The bacterium of claim 14, wherein said lactic acid bacterium is selected from the group consisting of *Lactobacillus acidophilus, L. gasseri, L. johnsonni*, and *L. plantarum*.

16. A method for modulating the oxalate degrading activity of a cell, comprising:
a) introducing into said cell at least one heterologous nucleic acid molecule comprising a nucleotide sequence having at least 95% sequence identity to SEQ ID NO: 3, wherein said nucleic acid molecule encodes a polypeptide having oxalate degrading activity; and
b) culturing said cell under conditions that allow for expression of the nucleic acid molecule,
wherein the expression of said nucleic acid molecule modulates the oxalate degrading activity of the cell.

17. The method of claim 16, wherein said cell is a bacterial cell.

18. The method of claim 17, wherein said cell further comprises a nucleic acid molecule comprising a nucleotide sequence having at least 95% sequence identity to SEQ ID NO:1, wherein said nucleotide sequence encodes a polypeptide having oxalate degrading activity.

19. A method for producing a polypeptide comprising culturing a microbial cell under conditions in which a heterologous nucleic acid molecule encoding the polypeptide is expressed wherein said polypeptide comprises an amino acid sequence having at least 95% sequence identity to the amino acid sequence as set forth in SEQ ID NO: 4, wherein said polypeptide has oxalate degrading activity.

20. A kit comprising the nucleic acid molecule of claim 1 and instructions for use.

21. The method of claim 17 further comprising:
  a) transforming said bacterial cell with a second nucleic acid molecule comprising a nucleotide sequence encoding a heterologous polypeptide, or fragment thereof; and
  b) culturing said bacterial cell under conditions that allow for expression of the second nucleic acid molecule,
  wherein said heterologous polypeptide or fragment thereof modifies the functional properties of said bacterial cell.

22. The isolated nucleic acid molecule of claim 1, wherein said nucleic acid molecule comprises the nucleotide sequence of SEQ ID NO: 3.

23. The isolated nucleic acid molecule of claim 1, wherein said nucleic acid molecule encodes a polypeptide comprising the amino acid set forth in SEQ ID NO: 4.

24. The plasmid of claim 2, wherein said nucleic acid molecule comprises the nucleotide sequence of SEQ ID NO:3.

25. The plasmid of claim 2, wherein said nucleic acid molecule encodes a polypeptide comprising the amino acid sequence set forth in SEQ ID NO:4.

26. The microbial cell of claim 3, wherein said nucleic acid molecule encodes a polypeptide comprising the amino acid sequence set forth in SEQ ID NO:4.

27. The method of claim 19, wherein said polypeptide comprises the amino acid sequence as set forth in SEQ ID NO:4.

28. The method of claim 19, wherein said microbial cell is a bacterial cell.

29. The method of claim 28, wherein said bacterial cell is a probiotic bacterium.

30. The method of claim 28, wherein said bacterial cell is a lactic acid bacterium.

31. The method of claim 30, wherein said lactic acid bacterium is selected from the group consisting of *Lactobacillus acidophilus*, *L. gasseri*, *L. johnsonni*, and *L. plantarum*.

32. The bacterium of claim 12, wherein said first nucleic acid molecule comprises the nucleotide sequence of SEQ ID NO: 3.

33. The bacterium of claim 12, wherein said second nucleic acid molecule comprises the nucleotide sequence of SEQ ID NO: 1.

34. The bacterium of claim 33, wherein said first nucleic acid molecule comprises the nucleotide sequence of SEQ ID NO: 3.

35. The method of claim 17, wherein said bacterial cell is a probiotic bacterium.

36. The method of claim 17, wherein said bacterial cell is a lactic acid bacterium.

37. The method of claim 36, wherein said lactic acid bacterium is selected from the group consisting of *Lactobacillus acidophilus*, *L. gasseri*, *L. johnsonni*, and *L. plantarum*.

* * * * *